US012808834B2

(12) United States Patent
Roy et al.

(10) Patent No.: US 12,808,834 B2
(45) Date of Patent: Nov. 24, 2026

(54) METHODS AND SYSTEMS FOR NUCLEIC ACID EXTRACTION

(71) Applicant: SEEK LABS, INC., Salt Lake City, UT (US)

(72) Inventors: Anindita Roy, Salt Lake City, UT (US); Madisen Pyper, Salt Lake City, UT (US); Jonathan Politis, Salt Lake City, UT (US); Dallin Ostler, Salt Lake City, UT (US); Eve F. Fabrizio, Salt Lake City, UT (US)

(73) Assignee: SEEK LABS, INC., Salt Lake City, UT (US)

( * ) Notice: Subject to any disclaimer, the term of this patent is extended or adjusted under 35 U.S.C. 154(b) by 1145 days.

(21) Appl. No.: 17/715,917

(22) Filed: Apr. 7, 2022

(65) Prior Publication Data

US 2022/0364077 A1 Nov. 17, 2022

Related U.S. Application Data

(60) Provisional application No. 63/240,227, filed on Sep. 2, 2021, provisional application No. 63/183,504, filed (Continued)

(51) Int. Cl.
*G01N 27/327* (2006.01)
*B01D 29/05* (2006.01)
(Continued)

(52) U.S. Cl.
CPC ......... *G01N 27/3276* (2013.01); *B01D 29/05* (2013.01); *B01D 29/58* (2013.01);
(Continued)

(58) Field of Classification Search
CPC ........ B01D 29/05; B01D 29/58; B01D 39/16; B01L 2300/0681; B01L 2400/0478;
(Continued)

(56) References Cited

U.S. PATENT DOCUMENTS

| | | | | |
|---|---|---|---|---|
| 5,234,809 A * | 8/1993 | Boom | .................. | C12Q 1/6806 536/25.4 |
| 5,673,822 A | 10/1997 | Chalmin et al. | | |

(Continued)

FOREIGN PATENT DOCUMENTS

| | | |
|---|---|---|
| CN | 102671487 A | 9/2012 |
| EP | 0585660 B1 | 9/1994 |

(Continued)

OTHER PUBLICATIONS

Su (Cellulose as a Matrix for Nucleic Acid Purification Analytical Biochemistry 267, 415-418 Article ID abio. 1998.2987 (Year: 1999).*

(Continued)

*Primary Examiner* — Jennifer Wecker
*Assistant Examiner* — Jonathan Bortoli
(74) *Attorney, Agent, or Firm* — Wilson Sonsini Goodrich & Rosati

(57) ABSTRACT

The present invention features a simplified sample processing method (e.g., VELOX) to collect high amounts of nucleic acids (e.g., genomic DNA (gDNA)) without equipment and without protein or other contaminants to interfere with sensor signals or similar nucleic acid detection test (sensors or per reagents). Specifically, the present invention provides systems, devices, and methods that allow for isolation and extraction of nucleic acids (e.g., gDNA) especially in a point of need setting.

19 Claims, 17 Drawing Sheets

Related U.S. Application Data on May 3, 2021, provisional application No. 63/171,761, filed on Apr. 7, 2021.

(51) Int. Cl.

| | |
|---|---|
| ***B01D 29/58*** | (2006.01) |
| ***B01D 39/16*** | (2006.01) |
| ***C12N 9/12*** | (2006.01) |
| ***C12N 15/10*** | (2006.01) |
| ***C12Q 1/6806*** | (2018.01) |
| ***C12Q 1/6853*** | (2018.01) |
| ***C12Q 1/70*** | (2006.01) |
| ***C25F 1/00*** | (2006.01) |

(52) U.S. Cl.

CPC ........... *B01D 39/16* (2013.01); *C12N 9/1252* (2013.01); *C12N 15/1017* (2013.01); *C12Q 1/6806* (2013.01); *C12Q 1/6853* (2013.01); *C12Q 1/701* (2013.01); *C25F 1/00* (2013.01); *C12Q 2600/166* (2013.01)

(58) Field of Classification Search

CPC ..... B01L 2400/0481; B01L 2400/0655; B01L 3/502; B01L 3/5635; C12M 25/14; C12M 29/14; C12N 15/1003; C12N 15/1017; C12N 9/1252; C12Q 1/6806; C12Q 1/6825; C12Q 1/6853; C12Q 1/701; C12Q 2565/519; C12Q 2600/166; C25F 1/00; G01N 27/3276

See application file for complete search history.

(56) References Cited

U.S. PATENT DOCUMENTS

| | | | | |
|---|---|---|---|---|
| 5,922,288 | A | 7/1999 | Herst | |
| 6,503,711 | B1 | 1/2003 | Krull et al. | |
| 6,609,618 | B2 | 8/2003 | Colpan | |
| 7,264,927 | B2 | 9/2007 | Nargessi et al. | |
| 8,367,334 | B2 | 2/2013 | Pugh et al. | |
| 8,598,338 | B2 | 12/2013 | Bair et al. | |
| 8,852,929 | B2 | 10/2014 | Jia | |
| 9,238,809 | B2 | 1/2016 | Khripin et al. | |
| 9,540,635 | B2 | 1/2017 | Ruegg et al. | |
| 9,637,777 | B2 | 5/2017 | Seul et al. | |
| 9,696,328 | B2 | 7/2017 | Hansen et al. | |
| 9,926,553 | B2 | 3/2018 | De John et al. | |
| 10,392,655 | B2 | 8/2019 | Boutell et al. | |
| 10,550,425 | B2 | 2/2020 | Sampas et al. | |
| 10,704,087 | B2 | 7/2020 | Satterfield | |
| 10,717,022 | B2 | 7/2020 | Menon et al. | |
| 10,934,541 | B2 | 3/2021 | Okajima et al. | |
| 11,180,787 | B2 | 11/2021 | Eboigbodin et al. | |
| 11,299,728 | B2 | 4/2022 | DeJohn et al. | |
| 2004/0191801 | A1 | 9/2004 | Heeger et al. | |
| 2005/0191619 | A1* | 9/2005 | Davis | C12N 15/1017 536/25.4 |
| 2006/0160064 | A1* | 7/2006 | Carbonell | B01J 20/3274 435/5 |
| 2007/0009925 | A1 | 1/2007 | Fang et al. | |
| 2007/0122809 | A1* | 5/2007 | Stevenson | C12N 15/1017 536/25.4 |
| 2007/0140915 | A1 | 6/2007 | Sakal et al. | |
| 2007/0154922 | A1 | 7/2007 | Collier et al. | |
| 2008/0026451 | A1 | 1/2008 | Braman et al. | |
| 2008/0113357 | A1* | 5/2008 | Baggio | C12N 15/1017 435/6.19 |
| 2008/0153078 | A1 | 6/2008 | Braman et al. | |
| 2008/0283741 | A1 | 11/2008 | Mukaibatake | |
| 2009/0111193 | A1* | 4/2009 | Cooney | G01N 1/405 436/178 |
| 2009/0148933 | A1 | 6/2009 | Battrell et al. | |
| 2009/0186357 | A1 | 7/2009 | Mauk et al. | |
| 2011/0166338 | A1 | 7/2011 | Jiang et al. | |
| 2012/0107799 | A1* | 5/2012 | Daum | C12Q 1/6806 422/534 |
| 2012/0288897 | A1 | 11/2012 | Ching et al. | |
| 2014/0134078 | A1 | 5/2014 | Njoroge et al. | |
| 2014/0134718 | A1* | 5/2014 | Hiesinger | C12N 15/1017 536/25.4 |
| 2016/0025763 | A1* | 1/2016 | Holmes | G01N 21/27 506/9 |
| 2016/0097049 | A1* | 4/2016 | Qian | C12N 15/1017 422/534 |
| 2016/0346781 | A1* | 12/2016 | Shen | C12N 15/1006 |
| 2017/0096694 | A1 | 4/2017 | Eboigbodin et al. | |
| 2017/0152549 | A1 | 6/2017 | Shih et al. | |
| 2017/0198279 | A1 | 7/2017 | Loper et al. | |
| 2017/0233791 | A1 | 8/2017 | Spier et al. | |
| 2017/0335313 | A1* | 11/2017 | Qian | C12Q 1/6806 |
| 2018/0280832 | A1* | 10/2018 | Menon | B01D 69/1216 |
| 2019/0231222 | A1* | 8/2019 | Ahmad | A61B 5/097 |
| 2019/0344269 | A1 | 11/2019 | Johnson et al. | |
| 2019/0376130 | A1 | 12/2019 | Nobile et al. | |
| 2020/0149030 | A1 | 5/2020 | Hillebrand et al. | |
| 2020/0200693 | A1 | 6/2020 | Boyanov et al. | |
| 2020/0391198 | A1 | 12/2020 | Yi | |
| 2021/0010065 | A1 | 1/2021 | Salk et al. | |
| 2021/0031199 | A1 | 2/2021 | Troiano | |
| 2024/0076649 | A1 | 3/2024 | Politis et al. | |
| 2025/0263689 | A1 | 8/2025 | Politis et al. | |

FOREIGN PATENT DOCUMENTS

| | | | |
|---|---|---|---|
| WO | 2003040687 | A2 | 5/2003 |
| WO | 2004094635 | A2 | 4/2004 |
| WO | 2005118847 | A1 | 12/2005 |
| WO | 2015022359 | A1 | 2/2015 |
| WO | 2015185655 | A1 | 12/2015 |
| WO | 2016041591 | A1 | 3/2016 |
| WO | 2016144192 | A1 | 9/2016 |
| WO | 2017218777 | A1 | 12/2017 |
| WO | 2018195594 | A1 | 11/2018 |
| WO | WO-2020243579 | A1 | 12/2020 |
| WO | WO-2024103063 | A1 | 5/2024 |

OTHER PUBLICATIONS

Wong, Ian Y., and Nicholas A. Melosh. "An electrostatic model for DNA surface hybridization." Biophysical journal 98.12 (2010): 2954-2963.

Xia, Xuhua. "The effect of probe length and GC% on microarray signal intensity: characterizing the functional relationship." Int J Syst Synthetic Biol 1.2 (2010): 171-183.

Binder et al. "Mismatch and G-stack modulated probe signals on SNP microarrays." PLoS One 4.11 (2009): e7862.

Gu et al. "Single molecule profiling of molecular recognition at a model electrochemical biosensor." Journal of the American Chemical Society 140.43 (2018): 14134-14143.

Kudlicki, Andrzej S. "G-quadruplexes involving both strands of genomic DNA are highly abundant and colocalize with functional sites in the human genome." PloS one 11.1 (2016): e0146174.

Yang et al. "Evidence for the direct interaction between methylene blue and guanine bases using DNA-modified carbon paste electrodes." Electroanalysis: An International Journal Devoted to Fundamental and Practical Aspects of Electroanalysis 14.18 (2002): 1299-1302.

Rohs et al. "Methylene blue binding to DNA with alternating GC base sequence: a modeling study." Journal of the American Chemical Society 122.12 (2000): 2860-2866.

Pereira et al. "An efficient method for genomic DNA extraction from different molluscs species." International journal of molecular sciences 12.11 (2011): 8086-8095.

Mason et al. "Rapid (30-second), equipment-free purification of nucleic acids using easy-to-make dipsticks." Nature protocols 15.11 (2020): 3663-3677.

Zou et al. "Nucleic acid purification from plants, animals and microbes in under 30 seconds." PLoS biology 15.11 (2017): e2003916.

(56) References Cited

OTHER PUBLICATIONS

Mason et al. "A simple, robust and equipment-free DNA amplification readout in less than 30 seconds." RSC advances 9.42 (2019): 24440-24450.
Satterfield, Brent C. "Cooperative Primers: 2.5 Million—Fold Improvement in the Reduction of Nonspecific Amplification." The Journal of Molecular Diagnostics 16.2 (2014): 163-173.
EP22785494.0 Extended European Search Report dated Feb. 17, 2025.
Ali, Nasir et al. Current Nucleic Acid Extraction Methods and Their Implications to Point-of-Care Diagnostics. BioMed research international 2017:9306564, 1-14 (2017).
Baldi, Paolo, and Nicola La Porta. Molecular Approaches for Low-Cost Point-of-Care Pathogen Detection in Agriculture and Forestry. Frontiers in plant science 11:570862, 1-16 (2020).
Chapter 2.2.8: Infection With white Spot Syndrome Virus. Manual of Diagnostic Tests for Aquatic Animals :1-16 (2019).
Hansen, Soren, and Ahmed Abd El Wahed. Point-Of-Care or Point-Of-Need Diagnostic Tests: Time to Change Outbreak Investigation and Pathogen Detection. Tropical medicine and infectious disease 5(4):151, 1-15 (2020).
Islam, Mohammed Shehadul et al. A Review on Macroscale and Microscale Cell Lysis Methods. Micromachines 8:83, 1-27 (2017).
Kim, Jungkyu et al. Microfluidic sample preparation: cell lysis and nucleic acid purification. Integration Biology 1(10):574-586 (2009).
Koetsier, Giron, and Eric Cantor. A practical guide to analyzing nucleic acid concentration and purity with microvolume spectrophotometers. New England Biolabs Inc :1-8 (2019).
Lightner, D V. Virus diseases of farmed shrimp in the Western Hemisphere (the Americas): a review. Journal of invertebrate pathology 106(1):110-130 (2011).
Paul, Rajesh et al. Advances in point-of-care nucleic acid extraction technologies for rapid diagnosis of human and plant diseases. Biosensors and bioelectronics 169:112592, 1-21 (2020).
Ripperger, Siegfried et al. Filtration, 1. Fundamentals. In Ullmann's Encyclopedia of Industrial Chemistry :1-38 (2013).
Sullivan, Timothy J. et al. Rapid, CRISPR-Based, Field-Deployable Detection Of White Spot Syndrome Virus In Shrimp. Scientific reports 9(1):19702, 1-7 (2019).
Tan, et al. DNA, RNA, and Protein Extraction: The Past and The Present. Journal of Biomedicine and Biotechnology, 2009, pp. 1-10.
Tang, Kathy F. J., and Donald V. Lightner. Quantification of white spot syndrome virus DNA through a competitive polymerase chain reaction. Aquaculture 189(1-2):11-21 (2000).
Tomaszewicz Brown, Ania et al. Development and validation of a portable, point-of-care canine distemper virus qPCR test. PloS one 15(4):e0232044, 1-22 (2020).
Tsai, Yun-Long et al. Validation of a commercial insulated isothermal PCR-based POCKIT test for rapid and easy detection of white spot syndrome virus infection in Litopenaeus vannamei. PloS one 9(3):e90545, 1-8 (2014).
Verbruggen, Bas et al. Molecular Mechanisms of White Spot Syndrome Virus Infection and Perspectives on Treatments. Viruses 8(1):23, 1-29 (2016).
Zou, Yiping et al. Nucleic acid purification from plants, animals and microbes in under 30 seconds. PLOS biology 15(11):e2003916, 1-22 (2017).

* cited by examiner

1. Add sample to the sample vial 2. (Optional) Grind sample within the sample vial

FIG. 15 (con't)
3. Remove plug and pull the plunger disposed within the sample tube to create a negative pressure.
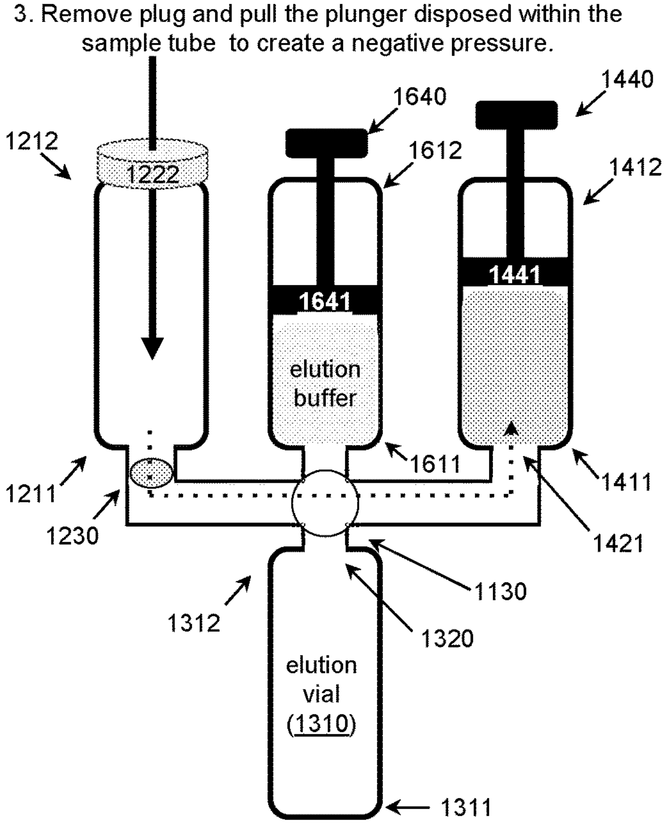
4. Push and pull the plunger disposed within the elution tube.
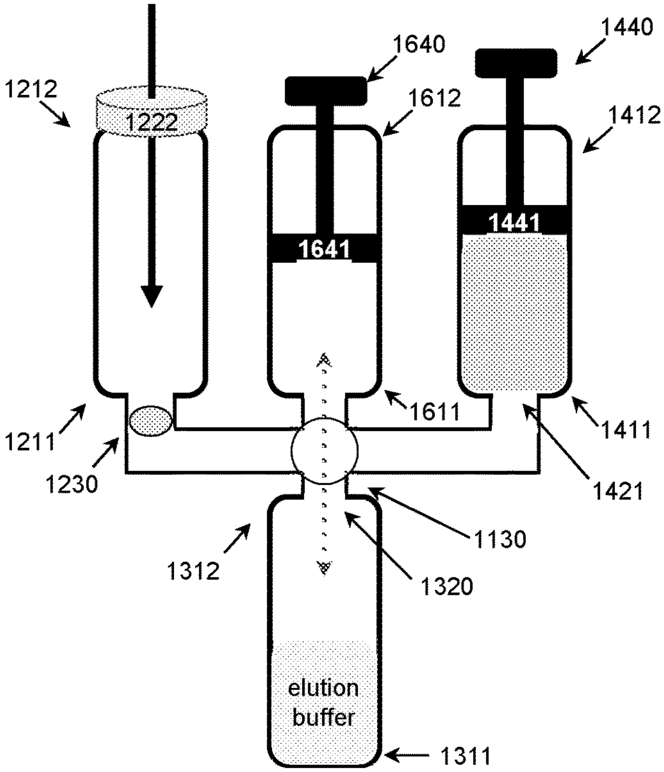

FIG. 17 (con't)
3. Attach a collection tube to the hub, remove plug and pull the plunger disposed within the collection tube to create a negative pressure.
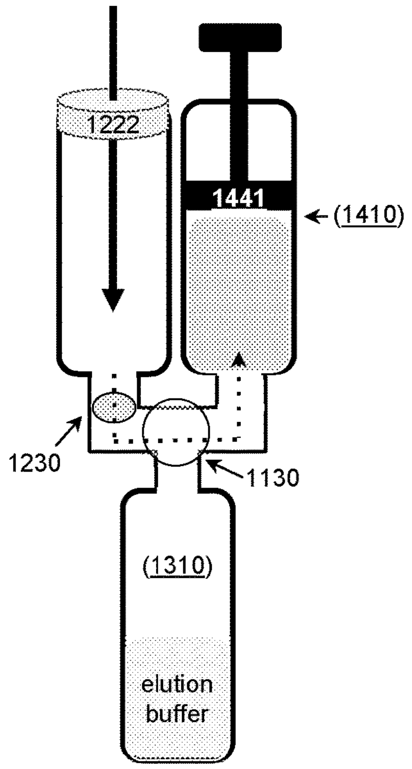
4. Remove the collection tube from the hub and attach an elution tube to the hub; pull the plunger disposed within the collection tube to create a negative pressure.
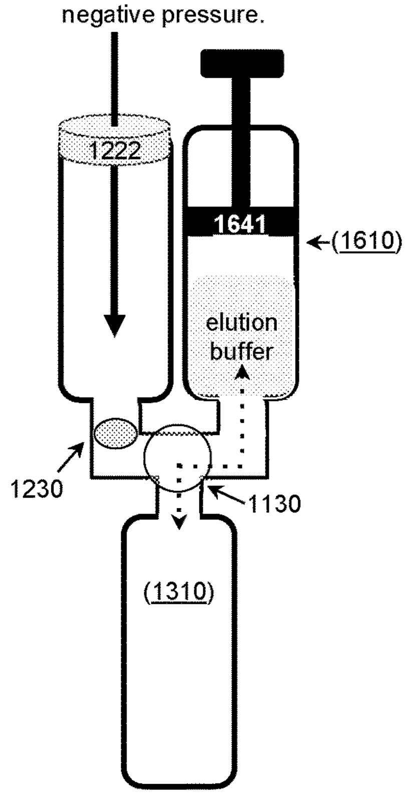

METHODS AND SYSTEMS FOR NUCLEIC ACID EXTRACTION

CROSS-REFERENCES TO RELATED APPLICATIONS

This application is a non-provisional and claims benefit of U.S. Provisional Application No. 63/171,761 filed Apr. 7, 2021, and U.S. Provisional Application No. 63/240,277 filed Sep. 2, 2021, the specification(s) of which is/are incorporated herein in their entirety by reference.

This application is a non-provisional and claims benefit of U.S. Provisional Application No. 63/183,504 filed May 3, 2021, the specification of which is incorporated herein in their entirety by reference.

FIELD OF THE INVENTION

The present invention features systems and methods for nucleic acid extraction where high amounts of genomic nucleic acid (e.g., genomic DNA) are collected from a sample.

BACKGROUND OF THE INVENTION

Nucleic acid detection at point-of-care is an extremely specific, sensitive, and accurate diagnostic technology that can help diagnose infectious diseases, cancer genetics, antibiotic-resistant bacteria, etc. Currently, sample collection and processing remain a roadblock in the current point of need for diagnostics. Specifically, methods of sample processing usually require laboratory-based procedures involving multiple steps and specific equipment (e.g., pipettors, centrifuge, incubator, vortex, magnetic beads) and skilled lab personnel. However, this limits the use of point of need sample processing, especially in resource-limited settings. Currently, the gold standard has been to collect samples and send them over to a testing facility where nucleic acid extraction, amplification, and detection can be carried out, and the results can take days. Most point-of-need rapid diagnostics rely on antigen-based detection methods. Nucleic acid based diagnostics are much more sensitive and accurate than antigen-based tests, with the added benefit of detection of low infection levels and differentiation of pathogen variants. Thus it is the need of the hour to develop a rapid, simple-to-use, equipment-free, cost-effective nucleic acid extraction method that gives high quality nucleic acid in high concentration in a short amount of time. The present invention features a rapid, equipment-free, and simplified sample processing method to collect samples with high amounts of nucleic acids (e.g., genomic DNA (gDNA)) and low levels of protein or samples with high amounts of nucleic acid that are essentially free of protein, since the protein may interfere with sensor signals and other contaminants which can interfere with amplification and detection methods.

BRIEF SUMMARY OF THE INVENTION

It is an objective of the present invention to provide systems, devices, methods, kits, and compositions that allow for the isolation and extraction of nucleic acids (e.g., genomic DNA) in a short amount of time, as specified in the independent claims. Embodiments of the invention are given in the dependent claims. Embodiments of the present invention can be freely combined with each other if they are not mutually exclusive.

The present invention features systems for isolating and extracting nucleic acids from a biological sample. In some embodiments, the system comprises a filter column. The filter may comprise a first column end and a second column end. In some embodiments, the first column end comprises a means for providing positive and negative pressure disposed therein, or operatively connected thereto, and the second column end comprises an opening. The system comprises a filter component disposed within the filtration column. In some embodiments, the filter component comprises a first filter, a second filter, and a solid support capable of reversibly binding nucleic acids sandwiched between the first filter and the second filter. In some embodiments, the system further comprises a plug, wherein the plug attaches to and/or effectively seals the opening of the filter column to create an enclosed system.

The present invention also features methods of isolating and extracting nucleic acids from a biological sample. In some embodiments, the method comprises attaching a sample vial comprising the biological sample to a filter column to create an enclosed system. In some embodiments, the method comprises creating negative pressure within the filter column to pull the lysed biological sample in the sample vial to pass through a prefilter and through the filter component, into the first column end of the filter column. In some embodiments, the method comprises creating a positive pressure with the filter column to push the lysed biological sample back into the collection tube. In some embodiments, the method comprises removing the sample vial and attaching an elution vial to a filter column to create an enclosed system. In some embodiments, the method comprises creating negative pressure within the filter column to pull the elution buffer through the filter component and into the first column end of the filter column. In some embodiments, the method comprises creating positive pressure within the filter column to push the elution buffer back into the elution vial. In some embodiments, the method comprises pulling and pushing the elution buffer through the filter component 2-10 times.

In further embodiments, the present invention features a sample processing method for isolating and extracting genomic DNA from a biological sample. In some embodiments, the method can collect genomic DNA from the sample at a minimum concentration of 100 ng/μL.

One of the unique and inventive technical features of the present invention is the use of an enclosed system. Without wishing to limit the invention to any theory or mechanism, it is believed that the technical feature of the present invention advantageously provides for a system that allows for the build-up of positive and negative pressure. None of the presently known prior references or work has the unique, inventive technical feature of the present invention.

Furthermore, the prior references teach away from the present invention. For example, prior arts do not teach of an enclosed system comprising a means for providing both positive and negative pressure within the enclosed system.

Additionally, the systems and devices of the present invention allow for the extraction of high quality genomic DNA (gDNA) in less than 15 minutes. The prior references teach away from this as many commercially available kits which give comparable gDNA quality take>1 hour and need multiple pieces of equipment and skilled lab technicians.

The methods and systems of the present invention have contributed to a surprising result. For example, the systems and devices of the present invention are able to isolate and extract high quality DNA with a 260/280 ratio (i.e., the ratio used to assess the purity of DNA) of 1.8 or above. Previous point of need systems appear only able to obtain DNA with a low 260/280 ratio (i.e., a ratio below 1.5).

As will be described herein, the present invention features systems for isolating and extracting nucleic acid from a biological sample. As an example, in some embodiments, the system comprises a filtration column having a first column end, a second column end, and an inner cavity, the filtration column comprising: a means for providing positive and negative pressure disposed at the first column end; an opening disposed in the second column end; a filter component immobilized in the inner cavity of the filtration column, the filter component divides the inner cavity into at least two subcavities wherein a first subcavity is between the filter component and the first column end and a second subcavity is between the filter component and the second column end, and configured such that fluid passing from the first subcavity to the second subcavity necessarily passes through the filter component, wherein the filter component comprises a solid support adapted to reversibly bind nucleic acid. In some embodiments, the filter component further comprises a first filter adjacent to or in contact with the solid support or a first filter and a second filter wherein the solid support is sandwiched between the first filter and second filter. In some embodiments, the system further comprises a sample vial having a first sample vial end, a second sample vial end, and an inner cavity, wherein a sample vial outlet is disposed in the second sample vial end, and a prefilter immobilized in the inner cavity of the of the sample vial dividing the inner cavity into at least two subcavities wherein a first subcavity is between the prefilter and the first sample vial end and a second subcavity is between the prefilter and the second sample vial end, and configured such that fluid passing from the first subcavity to the second subcavity necessarily passes through the prefilter for filtering cellular debris. In some embodiments, the opening in the second column end of the filtration column engages the sample vial outlet of the sample vial in a manner that fluidly connects the filtration column with the sample vial. In some embodiments, the system further comprises an elution vial having a first elution vial end, a second elution vial end, and an inner cavity, wherein an elution vial outlet is disposed in the second elution vial end, wherein the opening in the second column end of the filtration column engages the elution vial outlet of the elution vial in a manner that fluidly connects the filtration column with the elution vial.

As another example, in some embodiments, the system comprises a filtration column comprising a first column end and a second column end, wherein the first column end comprises a means for providing positive and negative pressure disposed therein, and the second column end comprises an opening; a filter component disposed within the filtration column, wherein the filter component comprises a first filter, a second filter, and a solid support capable of reversibly binding nucleic acid sandwiched between the first filter and the second filter; a sample vial comprising an outlet at a vial second end, wherein the opening of the filtration column attaches to the outlet of the sample vial to create an enclosed system. In some embodiments, the solid support comprises cellulose, nitrocellulose, a cotton pad, paper, or a combination thereof. In some embodiments, the system further comprises a prefilter disposed at the second sample vial end. In some embodiments, the prefilter comprises a polypropylene (PP) mesh filter.

In some embodiments, the system comprises a filter cartridge comprising a cartridge housing with a first end and a second end and a filter component sandwiched between said ends, wherein the first end comprises a first port and the second end comprises a second port, the ports are open to allow insertion and removal of fluid wherein the filter component reversibly binds nucleic acids; a sample tube comprising a sample tube housing for holding a fluid; a first cap removably attachable to a first end of the sample tube; wherein the first cap comprises a cap port adapted to snugly engage the first port or second port of the filter cartridge, the cap port is open to allow passage of fluid from the sample tube housing to the filter cartridge; a first means for providing positive and negative pressure for moving the fluid from the sample tube and through the filter cartridge from the first end to the second end or from the second end to the first end via the filter component; a second sample tube comprising a sample tube housing for holding a fluid; a second cap removably attachable to the first end of the second sample tube, wherein the second cap comprises a cap port adapted to sungly engage the first port or second port of the filter cartridge, the cap port is open to allow passage of fluid from the second sample tube housing to the filter cartridge; and a second means for providing positive and negative pressure for moving the fluid from the second sample tube and through to the filter cartridge from the first end to the second end or from the second end to the first end via the filter component. In some embodiments, the filter component comprises a solid support, the solid support comprises cellulose, nitrocellulose, a cotton pad, paper, or a combination thereof. In some embodiments, the first cap further comprises a prefilter positioned between the sample tube housing and cap port or within the cap port, wherein the prefilter is adapted to filter cellular debris. In some embodiments, the means for providing positive and negative pressure comprises a first syringe, and the means for providing positive and negative pressure comprises a second syringe. In some embodiments, the first syringe and second syringe each comprise a syringe housing, a plunger, and a syringe port, wherein the syringe port is disposed at a first end of the syringe and is open to allow passage of fluid, and the syringe port snugly engages the first port or second port of the filter cartridge, wherein the plunger is capable of moving between a first position and a second position to move fluid in and out of the syringe housing.

In some embodiments, the system comprises a sample vial comprising a sample vial opening is disposed at second sample vial end and a sample vial outlet disposed at a first sample vial end; a first collection tube comprising a inlet at a first collection tube end and a second collection tube end comprising a means for providing positive and negative pressure disposed therein; wherein the inlet of the first collection tube is fluidly connected to the sample vial outlet; an elution vial comprising an elution vial opening disposed at a second elution vial end and an first elution end; a elution tube comprising a inlet at a first elution tube end and a second elution tube end comprising a means for providing positive and negative pressure disposed therein; wherein the inlet of the elution tube is fluidly connected to the elution vial opening; and a filter component positioned between all of: the sample vial, the sample tube, the elution vial, and the elution tube such that fluid moving between the sample vial and sample tube or between the sample tube and elution tube or between the elution tube and elution vial necessarily passes through the filter component, the filter component comprises a solid support that is capable of temporarily binding nucleic acid.

In some embodiments, the sample vial further comprises a prefilter disposed at the second sample vial end positioned between the sample vial and the filter component, wherein the prefilter is capable of filtering cellular debris. In some embodiments, the solid support comprises cellulose, nitrocellulose, a cotton pad, paper, or a combination thereof. In some embodiments, the system further comprises a valve, wherein the filter component is disposed within the valve. In some embodiments, the valve comprises a first valve position and a second valve position, wherein when the valve is in the first valve position the valve fluidly connects the sample tube to the sample vial and the elution tube is not fluidly connected to the elution vial, and when the valve is in the second valve position the valve fluidly connects the elution tube to the elution vial and the first collection tube is not fluidly connected to the sample vial. In some embodiments, the system further comprises a lysis buffer for use in the sample vial, the lysis buffer comprising 20 mM PBS, 2.5 mM EDTA, and 0.05% SDS.

As will be described herein, the present invention features methods for isolating and extracting nucleic acid from a biological sample. As an example, in some embodiments, the method comprises using a system comprising: a sample vial comprising a sample vial opening disposed at a second sample vial end and a sample vial outlet disposed at a first sample vial end; a collection tube comprising an inlet at a first collection tube end and a second collection tube end comprising a means for providing positive and negative pressure disposed therein; wherein the inlet of the first collection tube is fluidly connected to the sample vial outlet; an elution vial comprising an elution vial opening disposed at a second elution vial end and a first elution end; an elution tube comprising a inlet at a first elution tube end and a second elution tube end comprising a means for providing positive and negative pressure disposed therein; wherein the inlet of the elution tube is fluidly connected to the elution vial opening; and a filter component positioned between all of: the sample vial, the sample tube, the elution vial, and the elution tube such that fluid moving between the sample vial and sample tube or between the sample tube and elution tube or between the elution tube and elution vial necessarily passes through the filter component, the filter component is capable of temporarily binding nucleic acid; the system further comprising a valve that can move between at least a first valve position and a second valve position, in the first valve position the valve allows a fluid connection between the sample tube and the sample vial but blocks a fluid connection between the elution tube and the elution vial, and in the second valve position the valve allows a fluid connection between the elution tube and the elution vial but blocks a fluid connection between the first collection tube and the sample vial. In some embodiments, the method comprises introducing the biological sample to the sample vial; with the valve to the first valve position, drawing the sample through the filter component and to the collection tube; and with the valve in the second valve position, pushing elution buffer from the elution tube to the elution vial via the filter component, thereby eluting DNA from the filter component and resulting in elution buffer with the DNA in the elution vial. In some embodiments, the method further comprises pulling the elution buffer from the elution vial back to the elution tube, and subsequently pushing the elution buffer from the elution tube back to the elution vial. In some embodiments, the pulling and pushing of the elution buffer is repeated 2-10 times. In some embodiments, the method is effective for collecting genomic DNA from the sample at a minimum concentration of 270 ng/μL.

In some embodiments, the method comprises using a system comprising: a filter cartridge comprising a cartridge housing with a first end and a second end and a filter component sandwiched between said ends, wherein the first end comprises a first port and the second end comprises a second port, the ports are open to allow insertion and removal of fluid wherein the filter component reversibly binds nucleic acids; a sample tube comprising a sample tube housing for holding a fluid; a first cap removably attachable to a first end of the sample tube; wherein the first cap comprises a cap port adapted to snugly engage the first port or second port of the filter cartridge, the cap port is open to allow passage of fluid from the sample tube housing to the filter cartridge; a first syringe for moving the fluid from the sample tube and through the filter cartridge from the first end to the second end or from the second end to the first end via the filter component, the first syringe comprises a syringe housing, a plunger, and a syringe port, wherein the syringe port is disposed at a first end of the syringe and is open to allow passage of fluid, the syringe port snugly engages the first port or the second port of the filter cartridge; a second sample tube comprising a sample tube housing for holding a fluid; a second cap removably attachable to the first end of the second sample tube, wherein the second cap comprises a cap port adapted to sungly engage the first port or second port of the filter cartridge, the cap port is open to allow passage of fluid from the second sample tube housing to the filter cartridge; and a second syringe for moving the fluid from the second sample tube and through to the filter cartridge from the first end to the second end or from the second end to the first end via the filter component, the second syringe comprises a syringe housing, a plunger, and a syringe port, wherein the syringe port is disposed at a first end of the syringe and is open to allow passage of fluid, the syringe port snugly engages the first port or the second port of the filter cartridge. In some embodiments, the method comprises introducing the biological sample to the sample tube and capping the sample tube with the first cap; inserting the port of the first cap into the first port of the cartridge and inserting the port of the first syringe into the second port of the cartridge, or inserting the port of the first cap into the second port of the cartridge and inserting the port of the first syringe into the first port of the cartridge; drawing the biological sample through the cartridge and into the syringe housing of the first syringe via the plunger, wherein nucleic acid in the biological sample temporarily binds to the filter component; removing the first syringe and sample tube from the cartridge, adding elution buffer to the second tube and capping the second tube with the second cap, and either inserting the port of a second syringe into the first port of the cartridge and the port of the second cap of the second sample tube into the second port of the cartridge or inserting the port of a second syringe into the second port of the cartridge and the port of the second cap of the second sample tube into the first port of the cartridge; and drawing the elution buffer through the filter cartridge to the syringe housing of the second syringe via the plunger, wherein the elution buffer elutes the DNA from the filter component.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

BRIEF DESCRIPTION OF THE SEVERAL VIEWS OF THE DRAWING(S)

The features and advantages of the present invention will become apparent from a consideration of the following detailed description presented in connection with the accompanying drawings in which.

Figure 3:
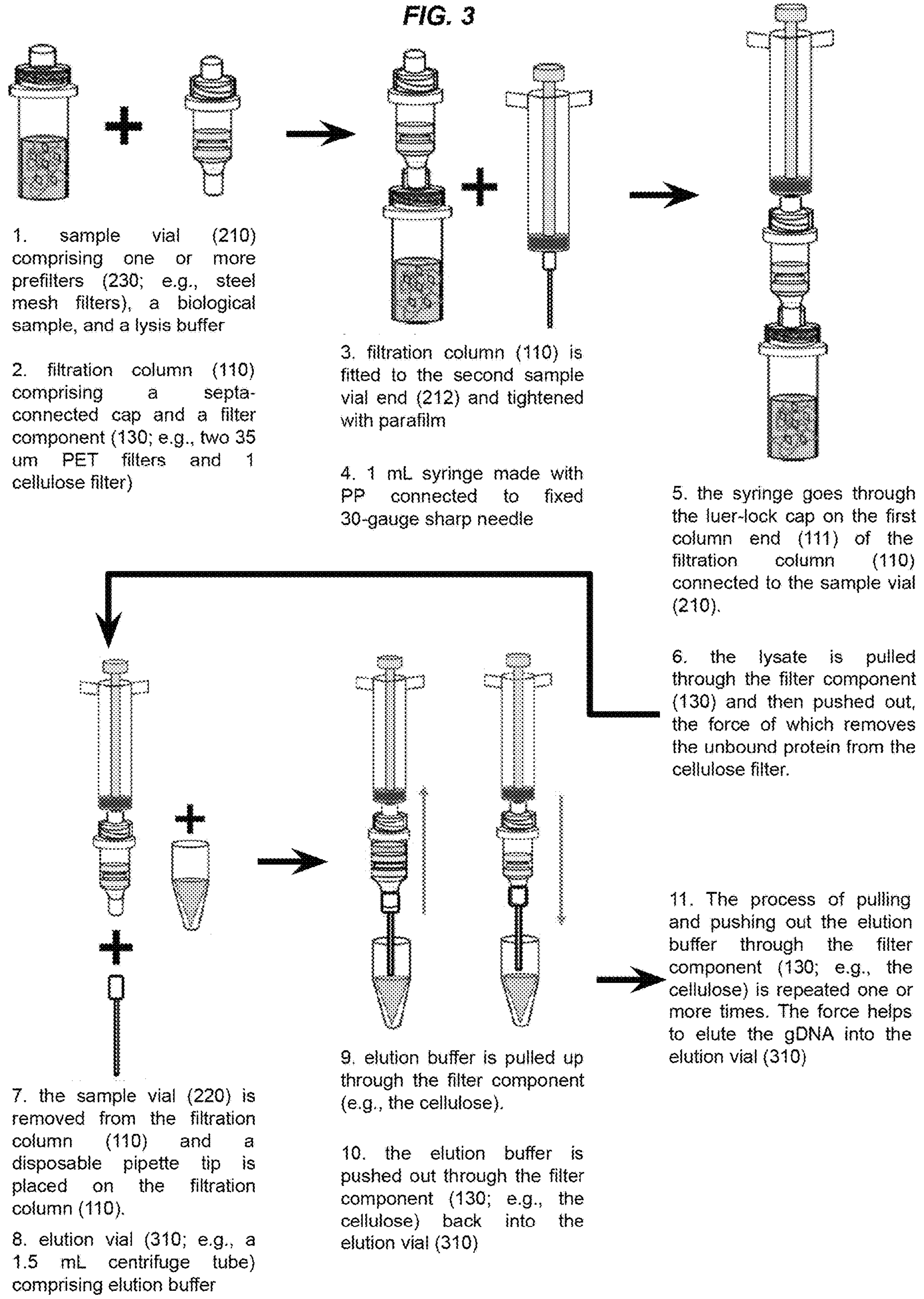

FIG. 3 shows a detailed illustration of a system and use of said system in a method to isolate and extract nucleic acids in accordance with some embodiments described herein. Specifically, FIG. 3 shows a filtration column (110; (2.)) comprising a septa-connected cap and a filter component (130; e.g., a filter component (130) comprising a first filter (131; e.g., 35 μm PET filter), a second filter (132; e.g., 35 μm PET filter), and a solid support (133; e.g., a cellulose filter punch) capable of reversibly binding nucleic acid sandwiched between the first filter (131) and the second filter (132)) fitted to a sample vial (210; (1.)) comprising one or more prefilters (230; e.g., steel mesh filters), a biological sample, and a lysis buffer. The filtration column (110) is fitted to the second sample vial end (212) and tightened with parafilm (3.). A 1 mL syringe made with polypropylene (PP) connected to a fixed 30-gauge sharp needle (4.) is inserted through the luer-lock cap on the filtration column (110). The lysate (i.e., the lysed biological sample) is pulled through the filter component (130; e.g., the first filter (131) and the second filter (132), which separates the cell debris; and the solid surface (133; e.g., the cellulose filter, which binds the nucleic acid (e.g., gDNA)) (5.). The lysate is then pushed out of the filtration column (130), the force of which removes the unbound protein from the cellulose punch (6.). The sample vial (220) is then removed from the filtration column (110), and a disposable pipette tip is placed on the second column end (112) of the filtration column (110) (7.). In this embodiment, the elution vial (310) is a 1.5 mL centrifuge tube containing the elution buffer (8.). The elution buffer is pulled (9.) and pushed (10.) through the filter component (130). This process of pulling and pushing the elution buffer through the filtration column (130) is repeated one or more times. The force may help to elute the nucleic acids (e.g., gDNA) into the elution vial (310) (11.).

Figure 4:
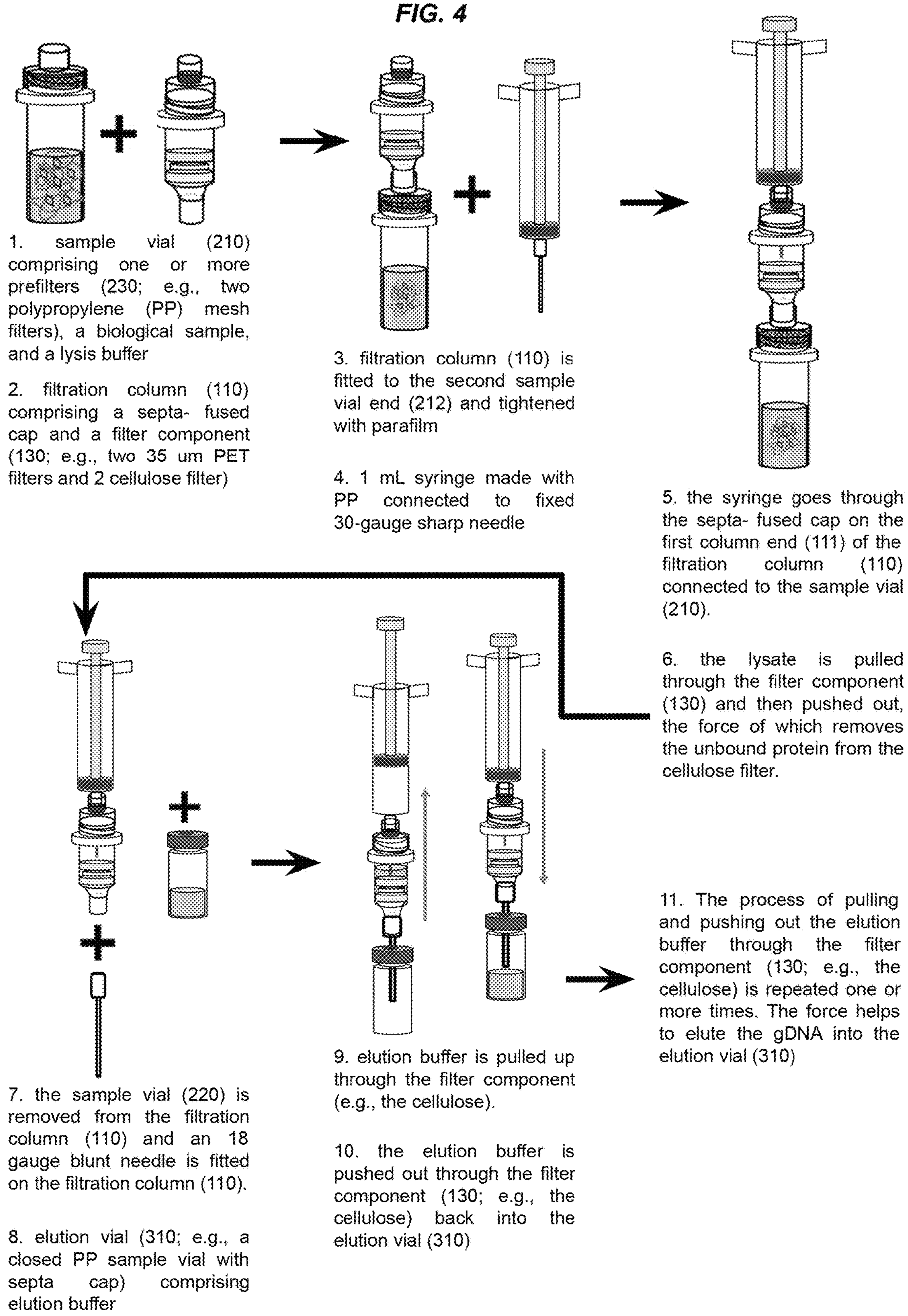

FIG. 4 shows a detailed illustration of a system and use of said system in a method to isolate and extract nucleic acids in accordance with some embodiments described herein. Specifically, FIG. 4 shows a filtration column (110; (2.)) comprising a septa-connected cap and a filter component (130; e.g., a filter component (130) comprising a first filter (131; e.g., 35 μm PET filter), a second filter (132; e.g., 35 μm PET filter), and two solid support (133; e.g., two cellulose filter punches) capable of reversibly binding nucleic acid sandwiched between the first filter (131) and the second filter (132)) fitted to a sample vial (210; (1.)) comprising one or more prefilters (230; e.g., two polypropylene mesh filters), a biological sample, and a lysis buffer. The filtration column (110) is fitted to the second sample vial end (212) and tightened with parafilm (3.). A 1 mL syringe made with polypropylene (PP) connected to a fixed 30-gauge sharp needle (4.) is inserted through the septa-connected cap on the filtration column (110)(5.). The system is then flipped, e.g., such that the syringe is positioned downward and the syringe is pulled to create a vacuum in the filtration column (110). The lysate (i.e., the lysed biological sample) is pulled from the sample vial (210) and through the filter component (130; e.g., the first filter (131) and the second filter (132), which separates the cell debris; and the solid surface (133; e.g., the cellulose filter, which binds the nucleic acid (e.g., gDNA)). The system is then flipped again and the lysate is pushed out of the filtration column (130), unclogging the debris if stuck on the first filter (131) or the second filter (132). As protein does not bind strongly to the solid support (133; e.g., cellulose), the force of the lysate moving through the filter component (130) removes the protein from the filter component (130), leaving the nucleic acids (e.g., gDNA) bound to the solid support (133; e.g., cellulose). This process may be repeated one or more times until the entire lysate is pulled through the filter component (130) and pushed back out (i.e., pushed back into the sample vial (210)) (6.). The sample vial (210) is then removed from the filtration column (110), and a blunt needle is placed on the second column end (112) of the filtration column (110) (7.). In this particular embodiment, the elution vial (310) is made with polypropylene (PP) with a septa cap and contains an elution buffer (8.). The elution buffer is pulled (9.) and pushed (10.) through the filter component (130). This process of pulling and pushing the elution buffer through the filtration column (130) one or more times. The force may help to elute the nucleic acids (e.g., gDNA) into the elution vial (310) (11.).

Figure 5:
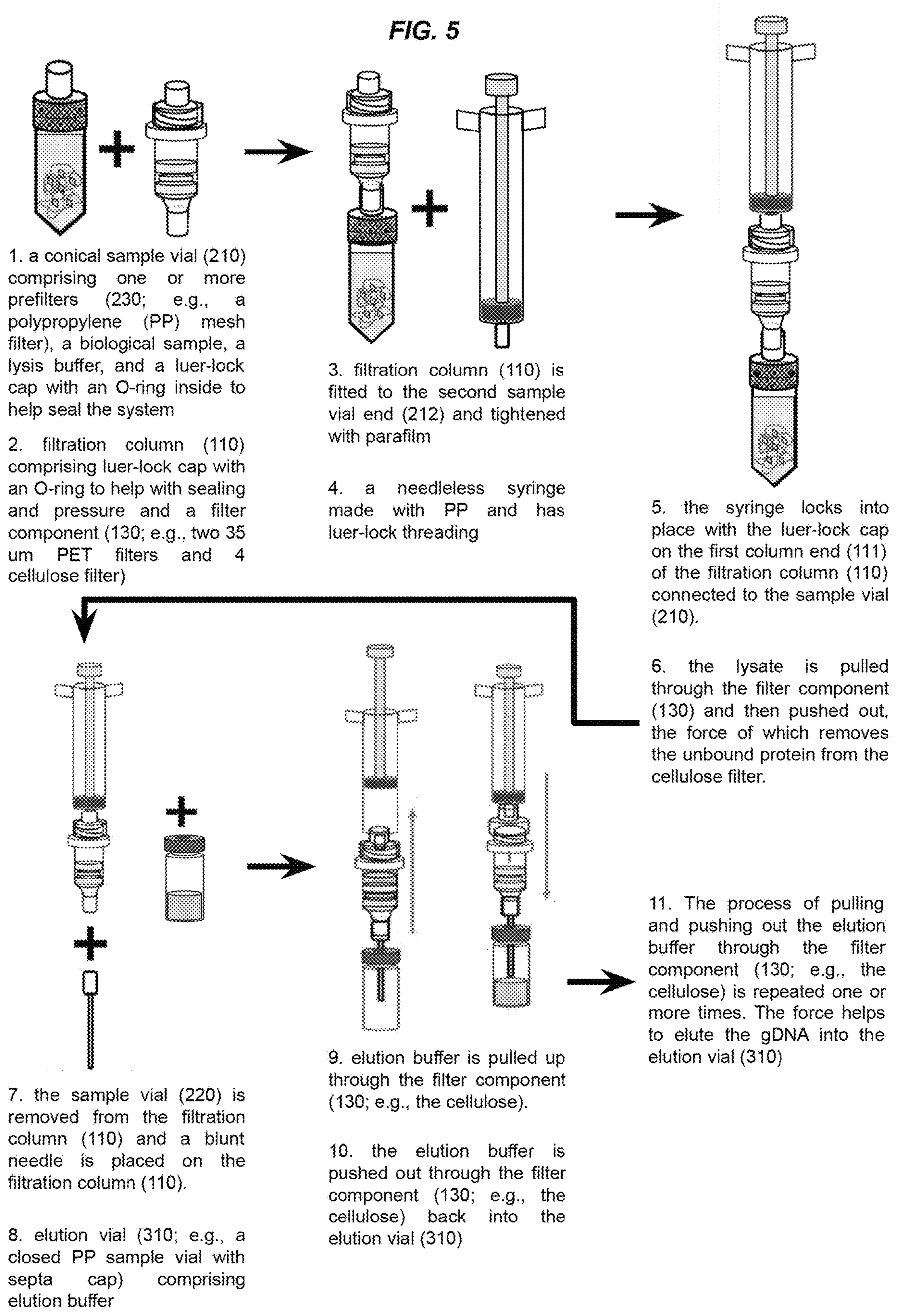

FIG. 5 shows a detailed illustration of a system and use of said system in a method to isolate and extract nucleic acids in accordance with some embodiments described herein. Specifically, FIG. 5 shows a filtration column (110; (2.)) comprising a luer-lock cap and a filter component (130; e.g., a filter component (130) comprising a first filter (131; e.g., 35 μm PET filter), a second filter (132; e.g., 35 μm PET filter), and four solid supports (133; e.g., four cellulose filter punches) capable of reversibly binding nucleic acid sandwiched between the first filter (131) and the second filter (132)) fitted to a conical sample vial (210; (1.)) comprising one or more prefilters (230; e.g., a polypropylene mesh filter), a luer-lock cap with an O-ring, a biological sample, and a lysis buffer. The filtration column (110) is fitted to the second sample vial end (212) and tightened with parafilm (3.). A needleless syringe (varying in size; e.g., 5 mL) made with polypropylene (PP) and comprising luer-lock threading (4.) is locked into place with the luer-lock cap on the first column end (111) of the filtration column (110) connected to the sample vial (210). The system is then flipped, e.g., such that the syringe plunger is positioned downward, and the syringe is pulled to create a vacuum in the filtration column (110). The lysate (i.e., the lysed biological sample) is pulled from the sample vial (210) and through the filter component (130; e.g., the first filter (131) and the second filter (132), which separates the cell debris; and the solid surface (133; e.g., the cellulose filter, which binds the nucleic acid (e.g., gDNA)) (5.). The system is then flipped again and the lysate is pushed out of the filtration column (130), unclogging the debris if stuck on the first filter (131) or the second filter (132) (6.). As protein does not bind strongly to the solid support (133; e.g., cellulose), the force of the lysate moving through the filter component (130) removes the protein from the filter component (130), leaving the nucleic acids (e.g., gDNA) bound to the solid support (133; e.g., cellulose). This process may be repeated one or more times until the entire lysate is pulled through the filter component (130) and pushed back out (i.e., pushed back into the sample vial (210)). The sample vial (210) is then removed from the filtration column (110), and a blunt needle is placed on the second column end (112) of the filtration column (110) (7.). In this particular embodiment, the elution vial (310) is made with polypropylene (PP) with a septa cap and contains an elution buffer (8.). The elution buffer is pulled (9.) and pushed (10.) through the filter component (130). This process of pulling and pushing the elution buffer through the filtration column (130) one or more times. The force may help to elute the nucleic acids (e.g., gDNA) into the elution vial (310) (11.).

Figure 6:
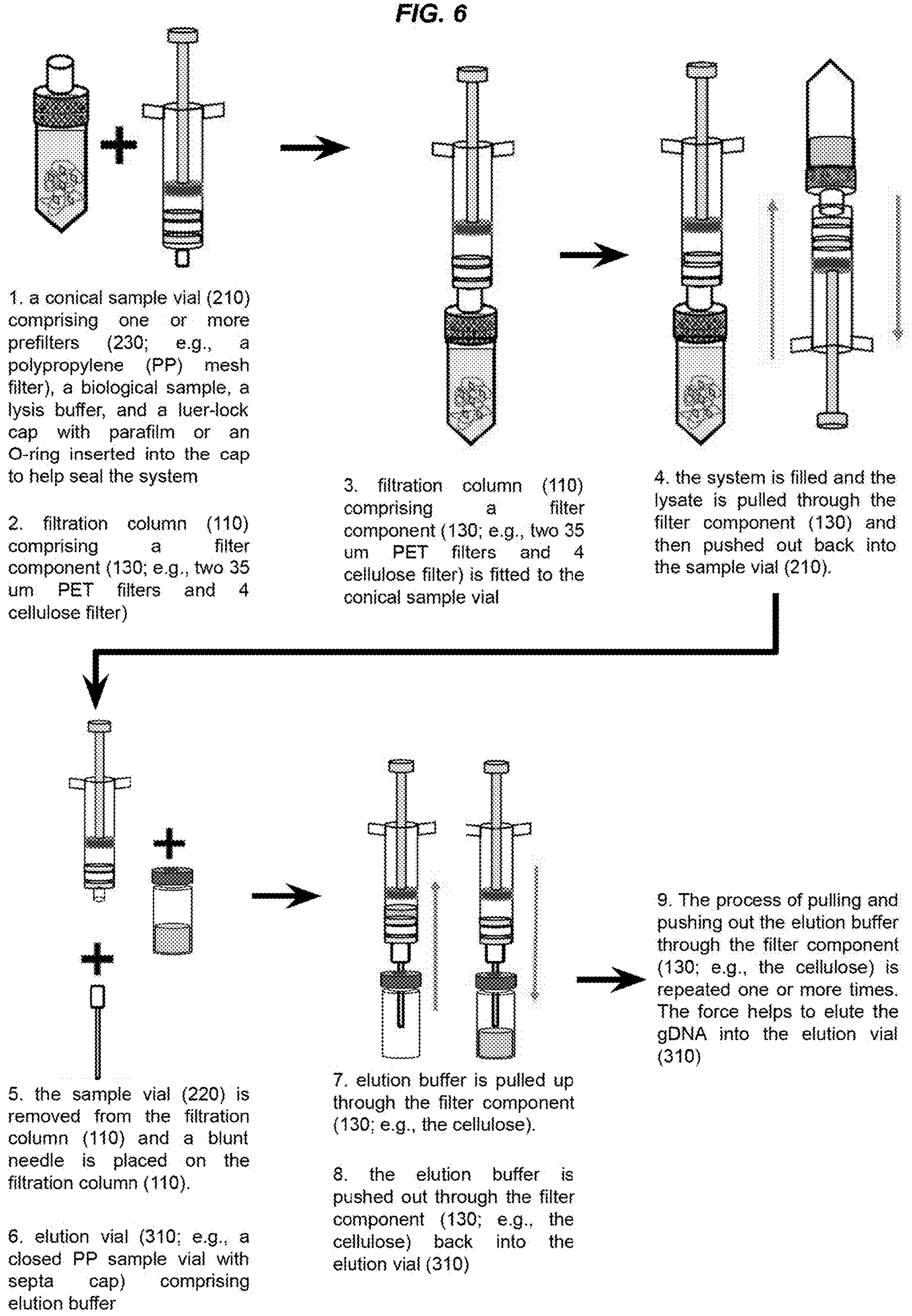

FIG. 6 shows a detailed illustration of a system and use of said system in a method to isolate and extract nucleic acids in accordance with some embodiments described herein. Specifically, FIG. 6 shows a needleless syringe which in this embodiment is also a filtration column (110; (2.)). The needleless syringe (i.e., the filtration column (110)) comprises a filter component (130) disposed therein. The filter component (130) comprises a first filter (131; e.g., 35 μm PET filter), a second filter (132; e.g., 35 μm PET filter), and four solid supports (133; e.g., four cellulose filter punches) capable of reversibly binding nucleic acid sandwiched between the first filter (131) and the second filter (132)). The needleless syringe is fitted to a conical sample vial (210; (1.)) comprising one or more prefilters (230; e.g., a polypropylene mesh filter), a luer-lock cap with either parafilm or an O-ring inserted into the cap, a biological sample, and a lysis buffer (3.). The system is then flipped, e.g., such that the syringe plunger is positioned downward, and the syringe is pulled to create a vacuum in the filtration column (110). The lysate (i.e., the lysed biological sample) is pulled from the sample vial (210) and through the filter component (130; e.g., the first filter (131) and the second filter (132), which separates the cell debris; and the solid surface (133; e.g., the cellulose filter, which binds the nucleic acid (e.g., gDNA)). The system is then flipped again, and the lysate is pushed out of the filtration column (130), unclogging the debris if stuck on the first filter (131) or the second filter (132). As protein does not bind strongly to the solid support (133; e.g., cellulose), the force of the lysate moving through the filter component (130) removes the protein from the filter component (130), leaving the nucleic acids (e.g., gDNA) bound to the solid support (133; e.g., cellulose). This process may be repeated one or more times until the entire lysate is pulled through the filter component (130) and pushed back out (i.e., pushed back into the sample vial (210)) (4.). The sample vial (210) is then removed from the needleless syringe (i.e., the filtration column (110)), and a blunt needle is placed on the second column end (112) of the filtration column (110) (5.). In this particular embodiment, the elution vial (310) is made with polypropylene (PP) with a septa cap and contains an elution buffer (6.). The elution buffer is pulled (7.) and pushed (8.) through the filter component (130). This process of pulling and pushing the elution buffer through the filtration column (130) one or more times. The force may help to elute the nucleic acids (e.g., gDNA) into the elution vial (310) (9.).

Figure 7:
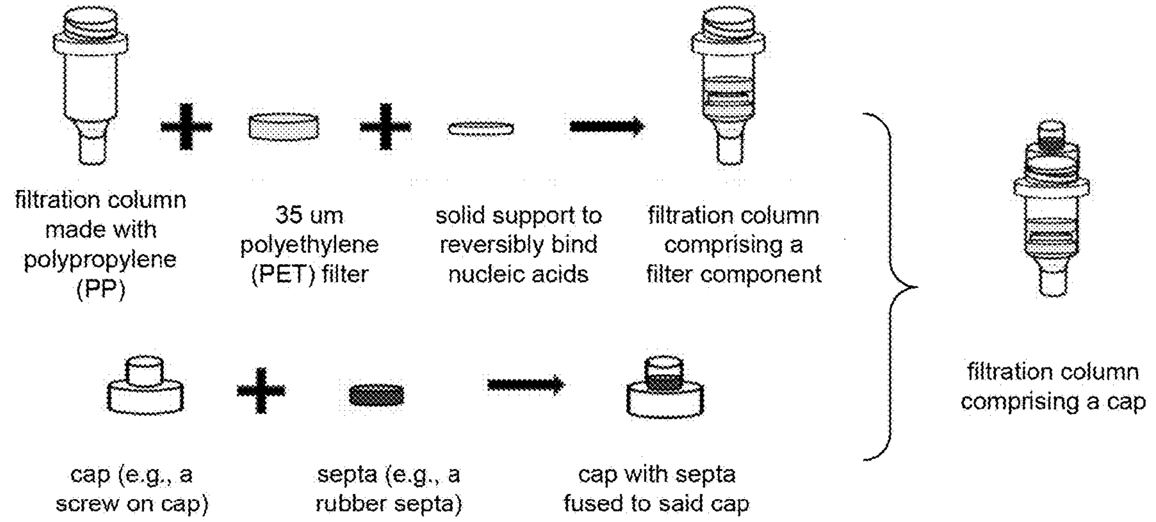

FIG. 7 shows a non-limiting example of how a filtration column is made. In some embodiments, the cap is attached (e.g., welded) to the filtration column to increase the pressure within the filtration column.

Figure 8:
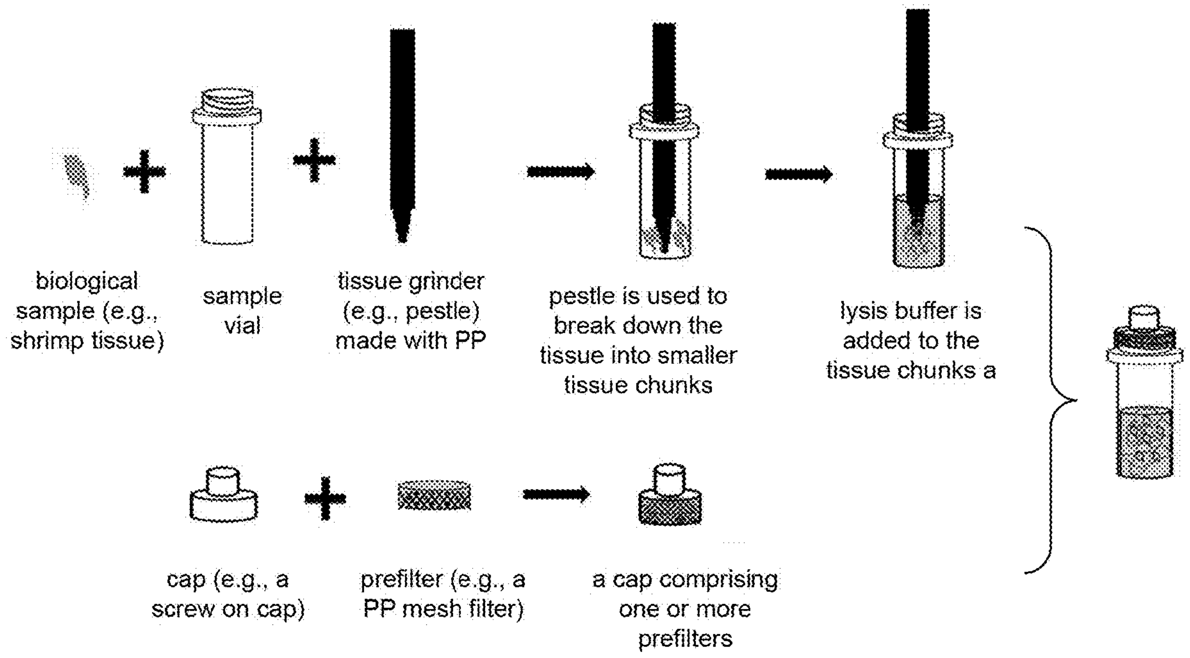

FIG. 8 shows a non-limiting example of lysing a biological sample. For example, a biological sample (e.g., a shrimp tissue sample (20-200 mg)) is added to a sample vial. A tissue grinder (e.g., a pestle) is used to break down the tissue sample into smaller tissue chunks. The tissue grinder may be a spiral pestle made with polypropylene (PP); in some embodiments, the tissue grinder may be attached to a motorized rotor for mechanical tissue lysis. Once the biological sample is lysed, a cap comprising one or more prefilters (e.g., two PP mesh filters) may be fused (e.g., welded) to the sample vial to prevent leakage.

Figure 9:
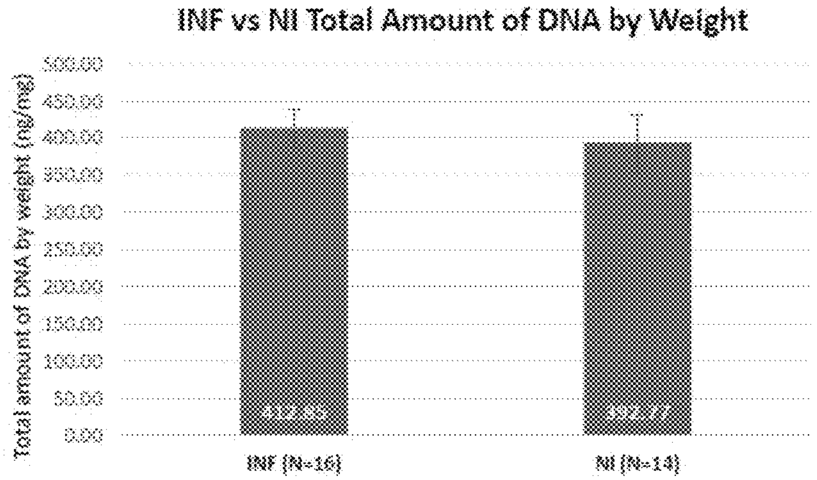

FIG. 9 shows total gDNA isolated from infected (INF) and non-infected (NI) animals using the systems as described herein. The total gDNA yield is not significantly different between infected animals (INF; e.g., animals infected with white spot syndrome virus (WSSV) and non-infected (NI) animals.

Figure 10A:
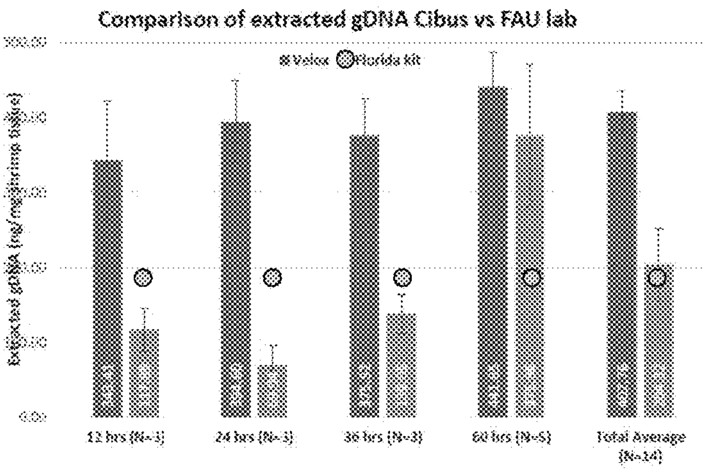
Figure 10B:
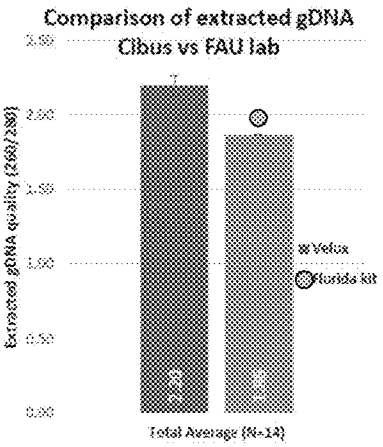

FIGS. 10A and 10B show methods described herein yield higher total gDNA with better quality (e.g., 260/280) compared to other methods (e.g., a commercial kit (e.g., Promega's Wizard genomic DNA extraction kit)). The commercial kit is denoted by the "florida kit" on the graph.

Figure 11:
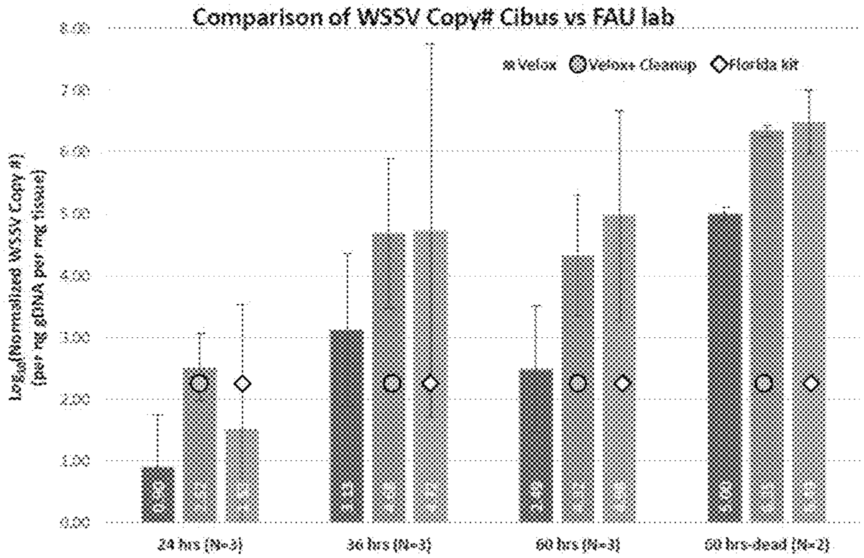

FIG. 11 shows that elution of gDNA using the methods described herein (e.g., the *Velox* method) has the same white spot syndrome virus (WSSV) copy number as the kit processed method used by the independent lab, thus showing there is no loss of WSSV nucleic acid despite the quick process achieved by *Velox* in comparison to 6 hours of the processing time by the independent lab.

Figure 12:
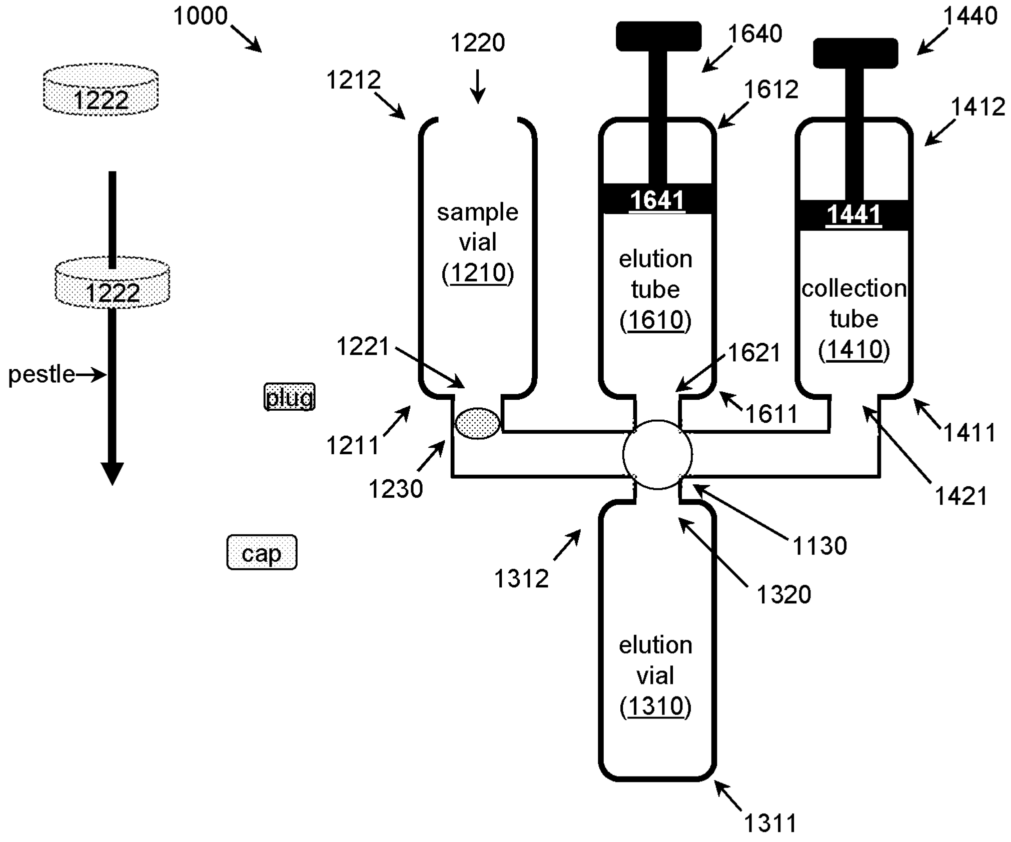

FIG. 12 shows, in accordance with some embodiments herein, a device for the nucleic acid isolation and extraction methods as described herein.

Figure 13:
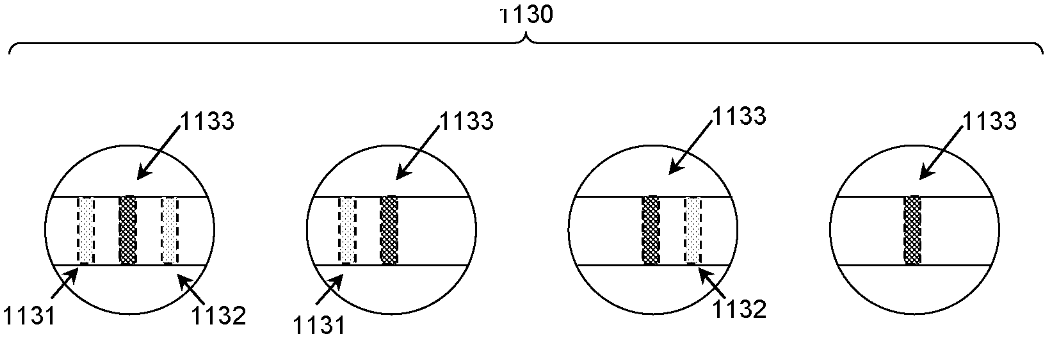

FIG. 13 shows in accordance with certain embodiments herein, the various configurations of the filter components of nucleic acid isolation and extraction device as described herein.

Figure 14A:
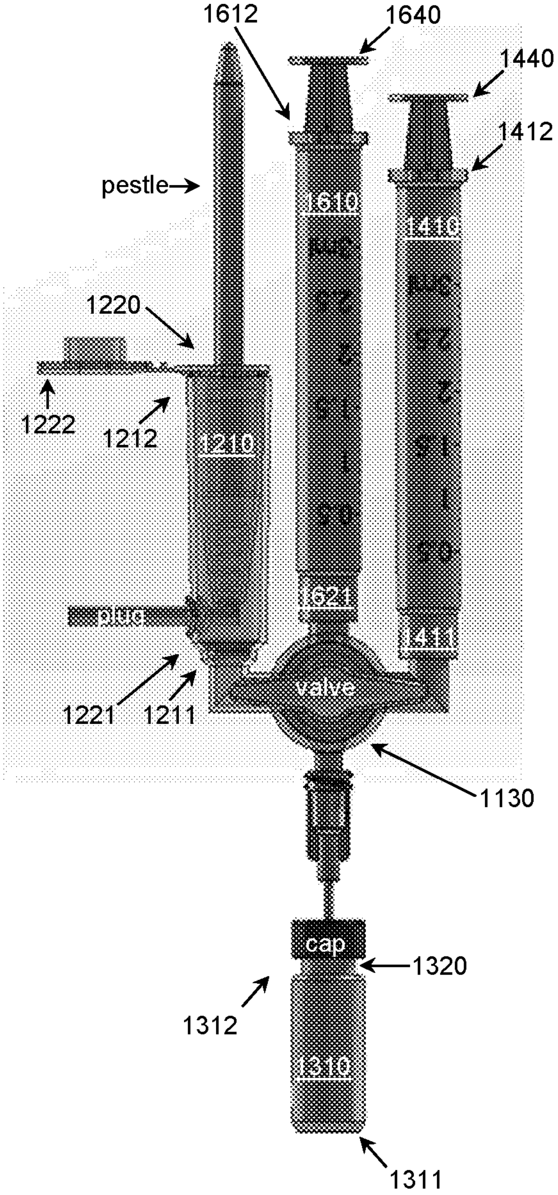
Figure 14B:
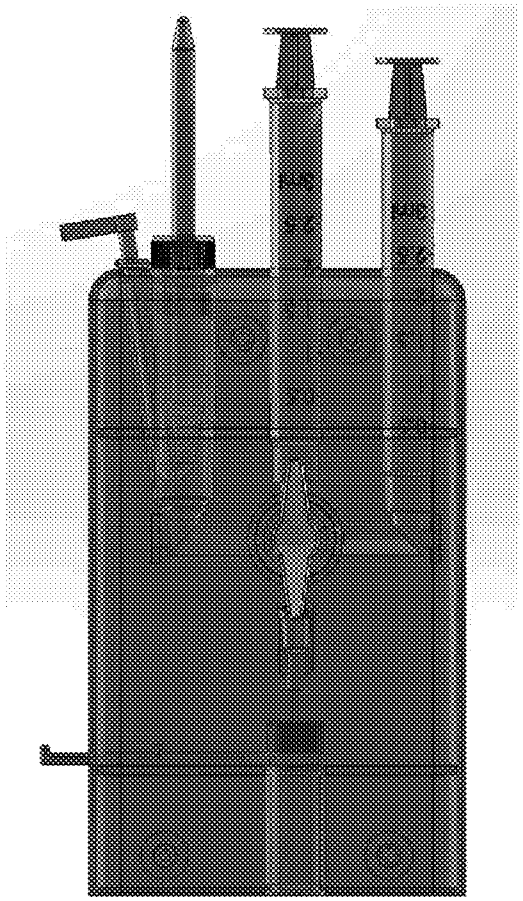

FIGS. 14A and 14B show a detailed illustration of the devices described herein. Specifically, FIG. 14A shows the device not enclosed in the casing, and FIG. 14B shows the enclosed device.

Figure 15:
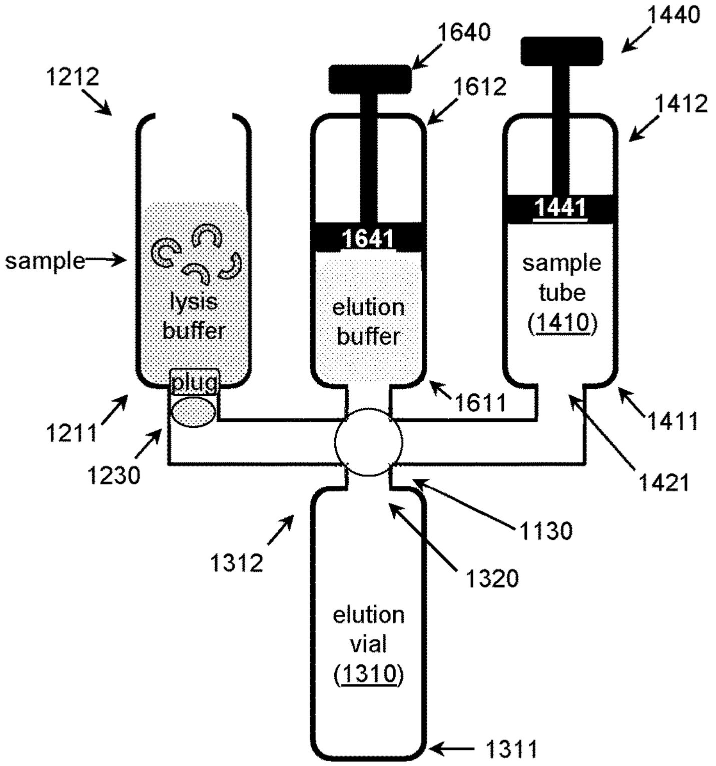
Figure 15:
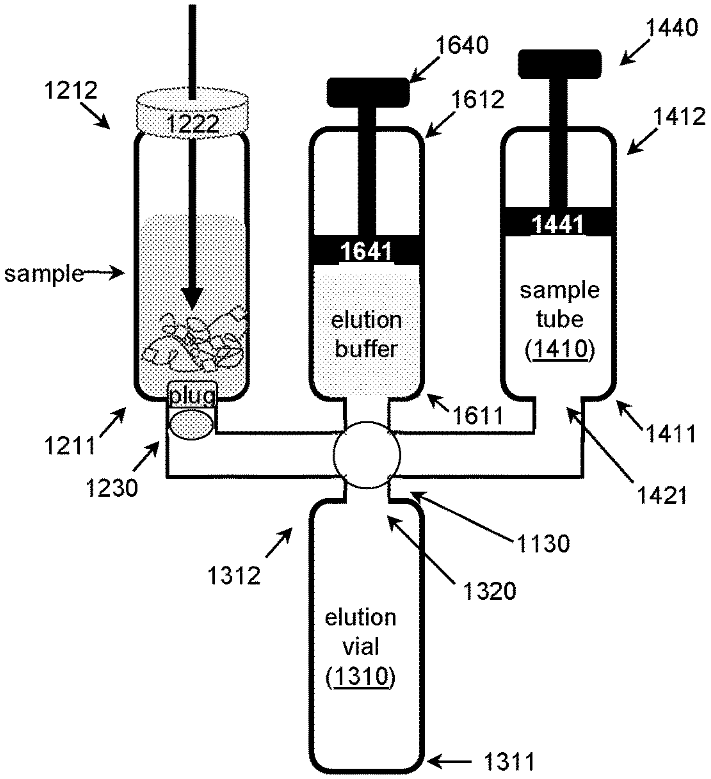

FIG. 15 shows an illustration of the method for isolating and extracting nucleic acids from a sample using a device as described herein. Dashed arrows indicate the flow of fluid within the device.

Figure 16:
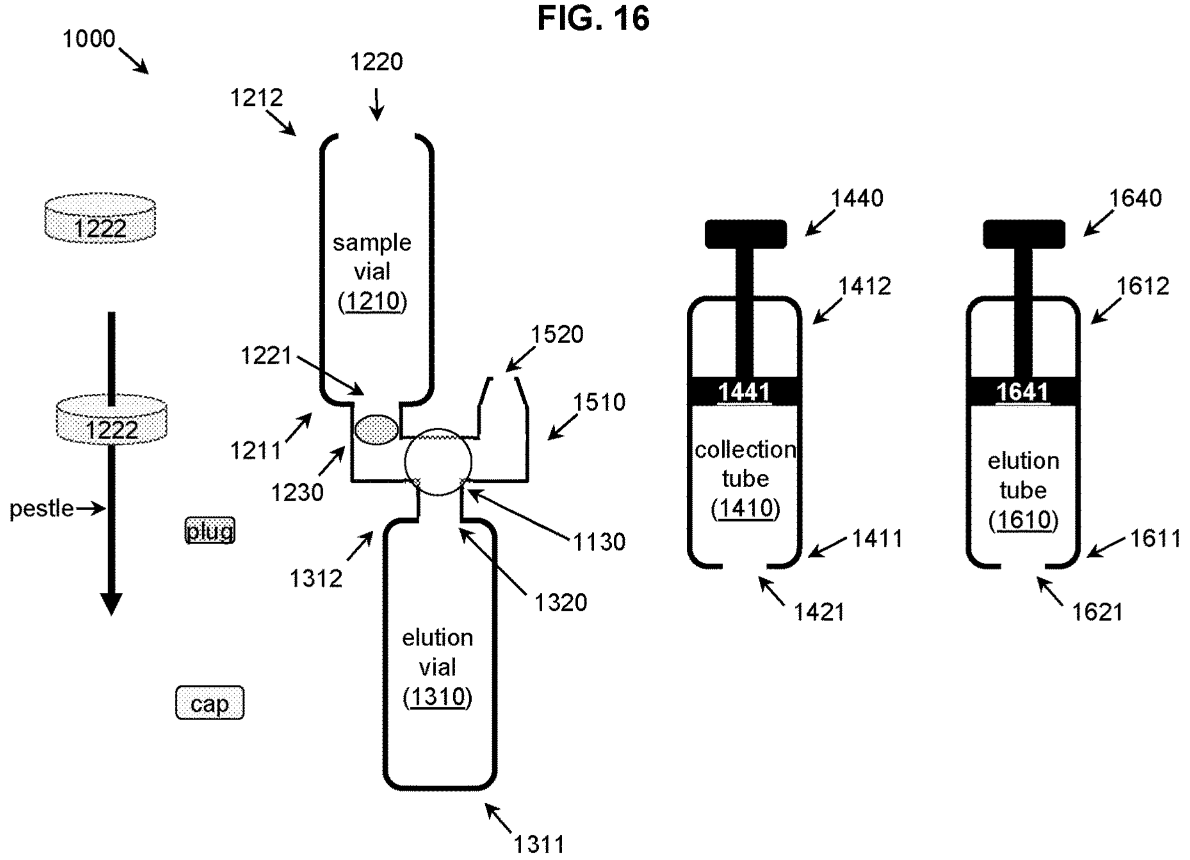

FIG. 16 shows in accordance with some embodiments herein, an example of a modular device for the nucleic acid isolation and extraction methods as described herein.

Figure 17:
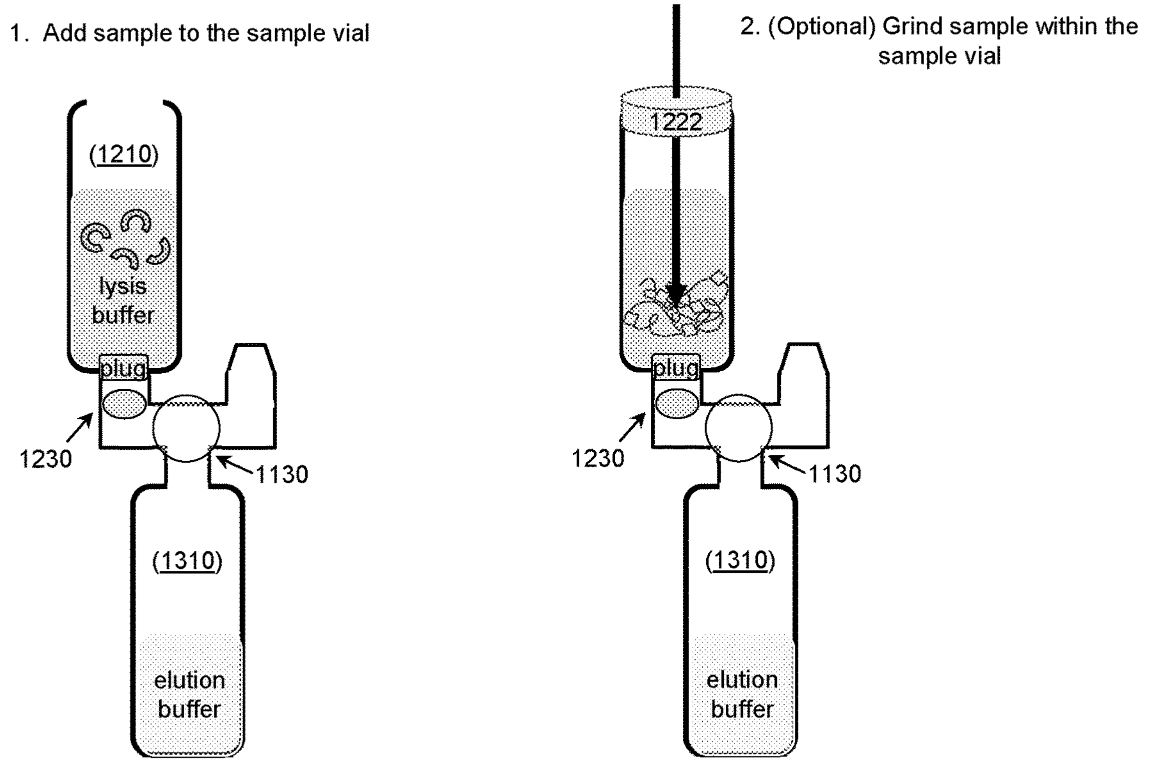

FIG. 17 shows an illustration of the method for isolating and extracting nucleic acids from a sample using a modular device as described herein. Dashed arrows indicate the flow of fluid within the device.

Figure 18:
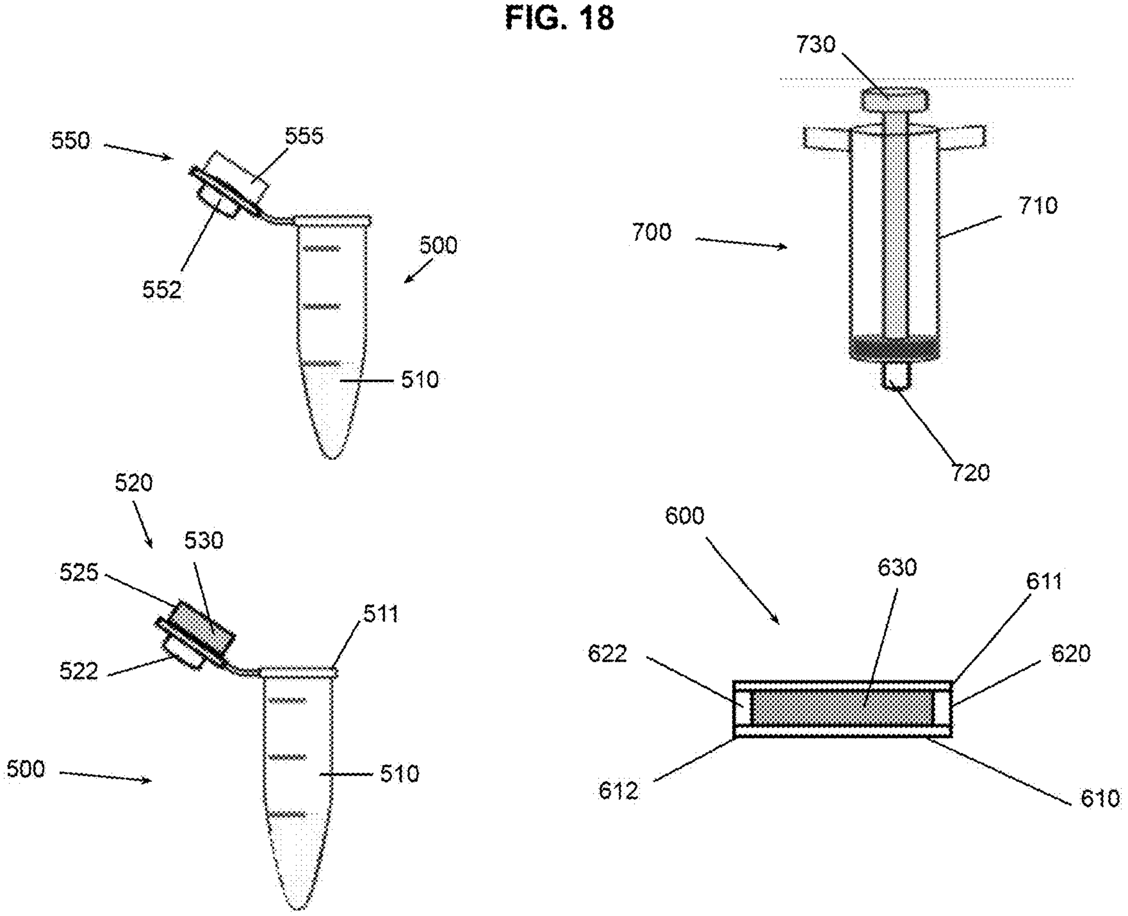

FIG. 18 shows a group of components that may be used in systems and methods for nucleic acid isolation and extraction as described herein. For example, the system or methods may feature one or more tubes, e.g., a sample vial for holding the sample, a buffer, etc., a filter cartridge, and a syringe.

Figure 19:
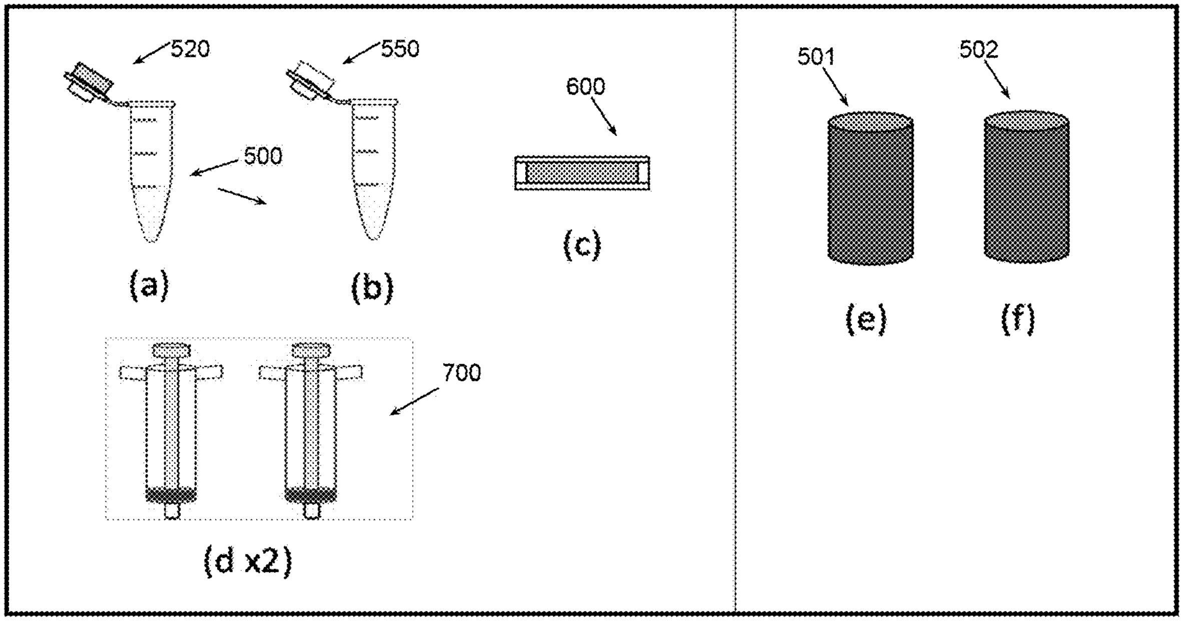

FIG. 19 shows components may be combined to create a kit. For example, the kit may comprise a cartridge, two syringes, two tubes, one first cap, and one second cap. In some embodiments, the kit further comprises one or more buffers, e.g., a lysis buffer, an elution buffer, etc.

Figure 20:
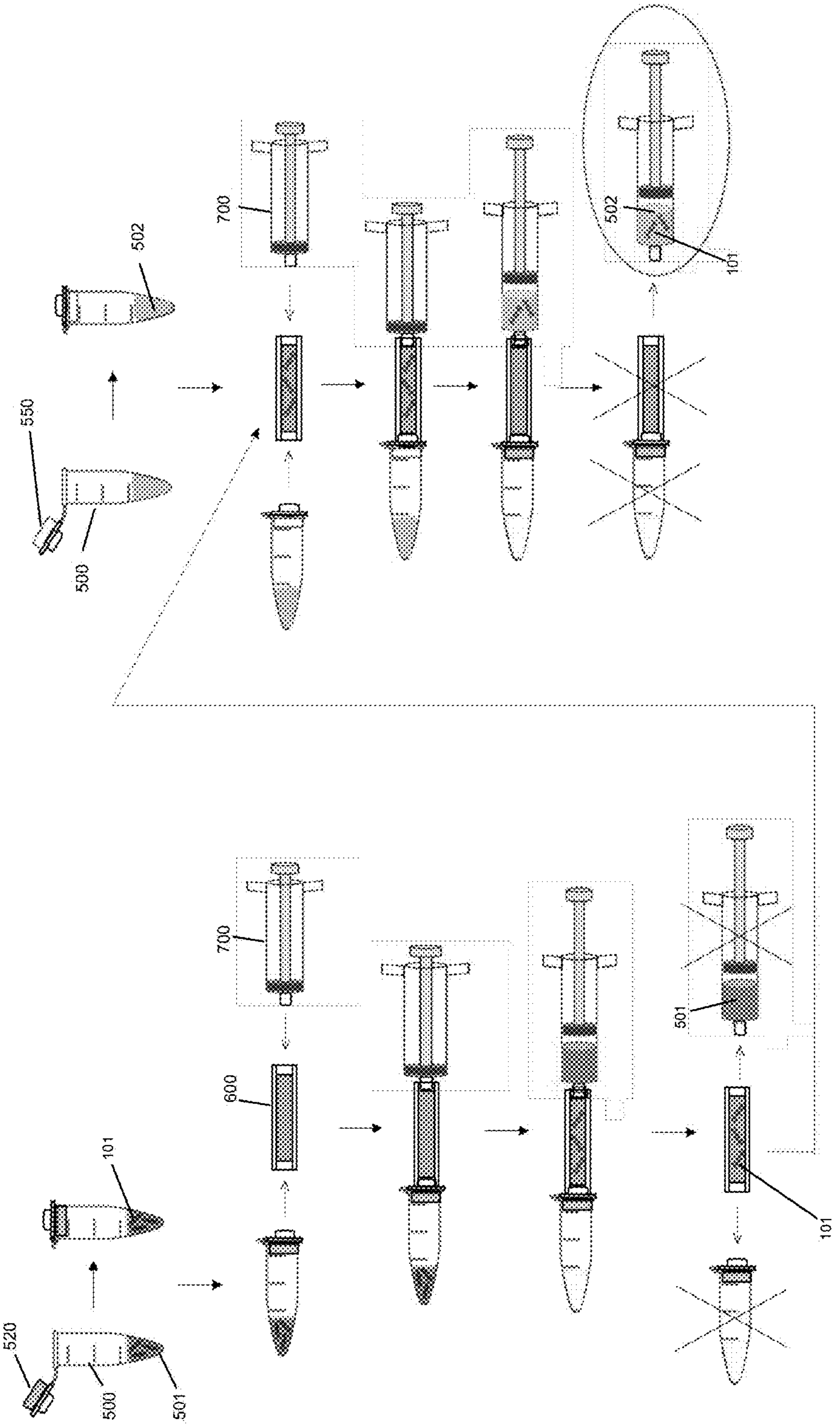

FIG. 20 shows methods of nucleic acid extraction and isolation using the components with a kit described herein.

DETAILED DESCRIPTION OF THE INVENTION

Following is a list of elements corresponding to a particular element referred to herein:

101 Nucleic acids
110 Filtration Column
111 First Column End

112 Second Column End
120 Opening
130 Filter Component
131 First Filter
132 Second Filter
133 Solid Support
140 Plunger
141 First Plunger End
210 Sample Vial
211 First Sample Vial End
212 Second Sample Vial End
220 Sample Vial Outlet
230 Prefilter
310 Elution Vial
311 First Elution Vial End
312 Second Elution Vial End
320 Elution Vial Outlet
500 Sample tube
501 Lysis buffer
502 Elution buffer
510 Sample tube housing
511 Top end of Sample tube
520 First tube cap
522 Open port of first tube cap
525 First tube cap seal
530 Pre-filter
550 Second tube cap
552 Open port of second tube cap
555 Second tube cap seal
600 Filter cartridge
610 Cartridge housing
611 First end of cartridge housing
612 Second end of cartridge housing
620 First open port of cartridge housing
622 Second open port of cartridge housing
630 Filter component
700 Syringe
710 Syringe housing
720 Open port of syringe
730 Syringe plunger
1000 Device
1130 Filter Component
1131 First Filter
1132 Second Filter
1133 Solid Support
1210 Sample Vial
1211 First Sample Vial End
1212 Second Sample Vial End
1220 Sample Vial Opening
1221 Sample Vial Outlet
1222 Cover
1230 Prefilter
1410 First Collection Tube
1411 First Collection Tube End
1412 Second Collection Tube End
1421 Inlet
1440 Plunger
1441 First Plunger End
1310 Elution Vial
1311 First Elution Vial End
1312 Second Elution Vial End
1320 Opening
1610 Elution Tube
1611 First Elution Tube End
1612 Second Elution Tube End
1621 Inlet
1640 Plunger
1641 First Plunger End
1510 Hub
1520 Opening For purposes of summarizing the disclosure, certain aspects, advantages, and novel features of the disclosure are described herein. It is to be understood that not necessarily all such advantages may be achieved in accordance with any particular embodiments of the disclosure. Thus, the disclosure may be embodied or carried out in a manner that achieves or optimizes one advantage or group of advantages as taught herein without necessarily achieving other advantages as may be taught or suggested herein.

Additionally, although embodiments of the disclosure have been described in detail, certain variations and modifications will be apparent to those skilled in the art, including embodiments that do not provide all the features and benefits described herein. It will be understood by those skilled in the art that the present disclosure extends beyond the specifically disclosed embodiments to other alternative or additional embodiments and/or uses and obvious modifications and equivalents thereof. Moreover, while a number of variations have been shown and described in varying detail, other modifications, which are within the scope of the present disclosure, will be readily apparent to those of skill in the art based upon this disclosure. It is also contemplated that various combinations or sub-combinations of the specific features and aspects of the embodiments may be made and still fall within the scope of the present disclosure. Accordingly, it should be understood that various features and aspects of the disclosed embodiments can be combined with or substituted for one another in order to form varying modes of the present disclosure. Thus, it is intended that the scope of the present disclosure herein disclosed should not be limited by the particular disclosed embodiments described herein.

As used herein, the singular forms "a," "an," and "the" are intended to include the plural forms as well, unless the context clearly indicates otherwise. Furthermore, to the extent that the terms "including," "includes," "having," "has," "with," or variants thereof are used in either the detailed description and/or the claims, such terms are intended to be inclusive in a manner similar to the term "comprising."

Referring now to the figures, the present invention features systems, devices and methods for nucleic acid extraction where high amounts of genomic nucleic acids (e.g., DNA or RNA) are collected from a sample.

Figure 1A:
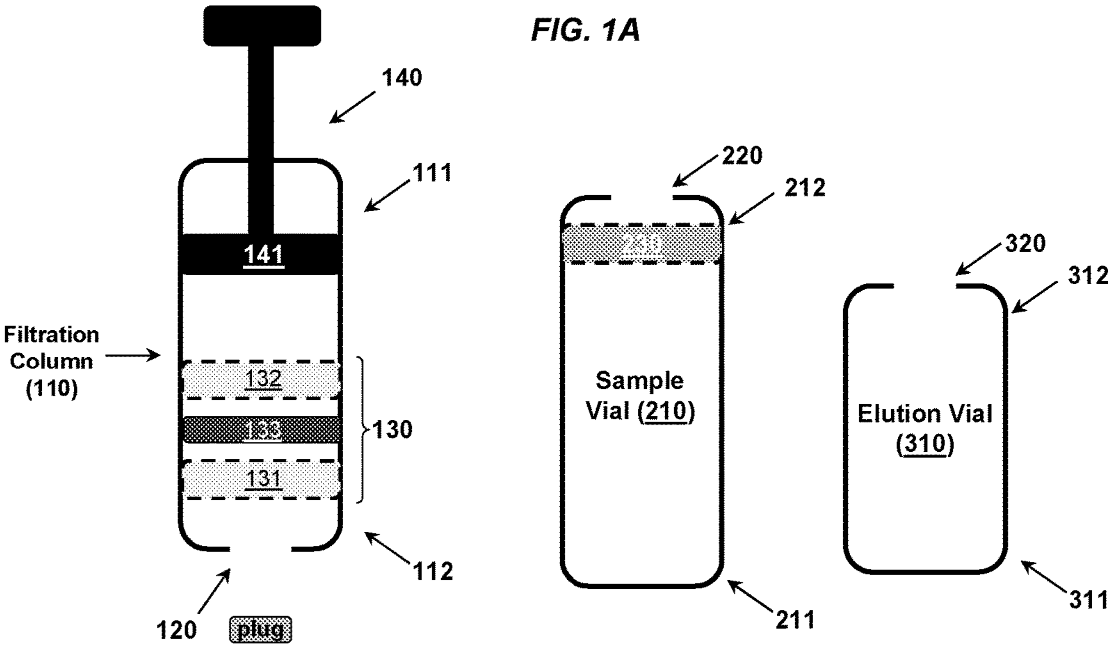
FIG. 1A shows, in accordance with some embodiments herein, the components (e.g., a filtration column, a sample vial, and an elution vial) for the nucleic acid isolation and extraction system as described herein.
Figure 1B:
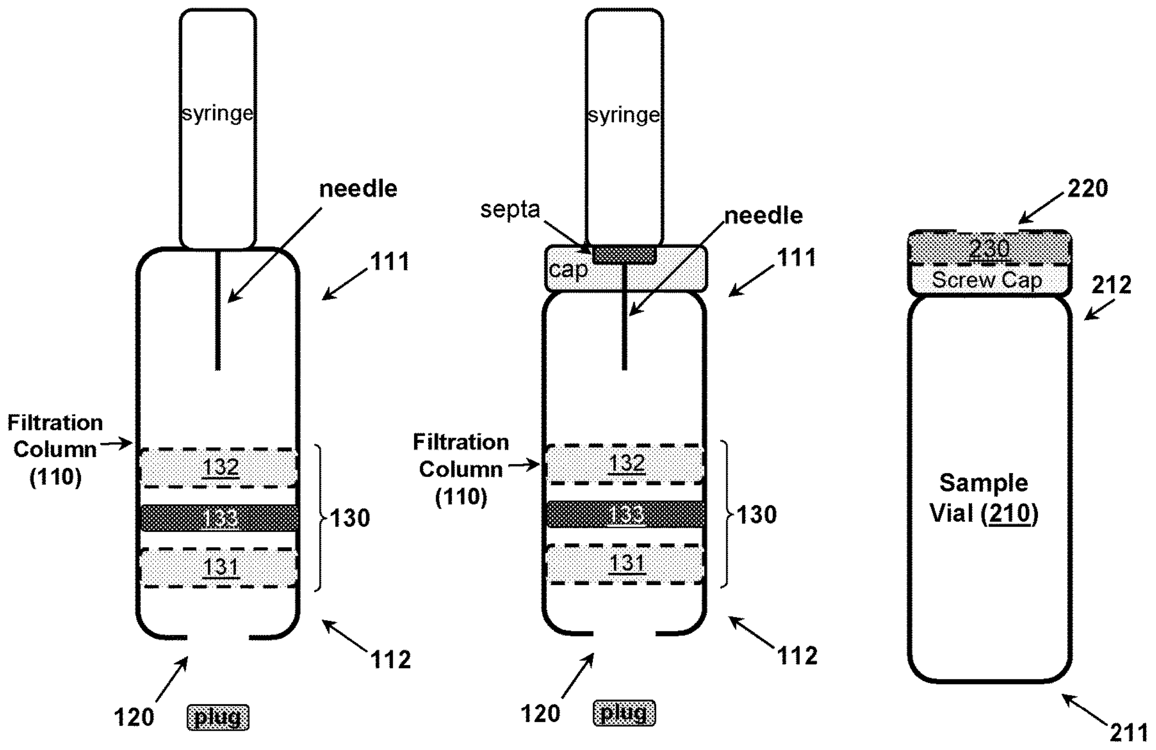
FIG. 1B shows, in accordance with other embodiments herein, the components (e.g., filtration columns and sample vial) of nucleic acid isolation and extraction system as described herein.
Figure 1C:
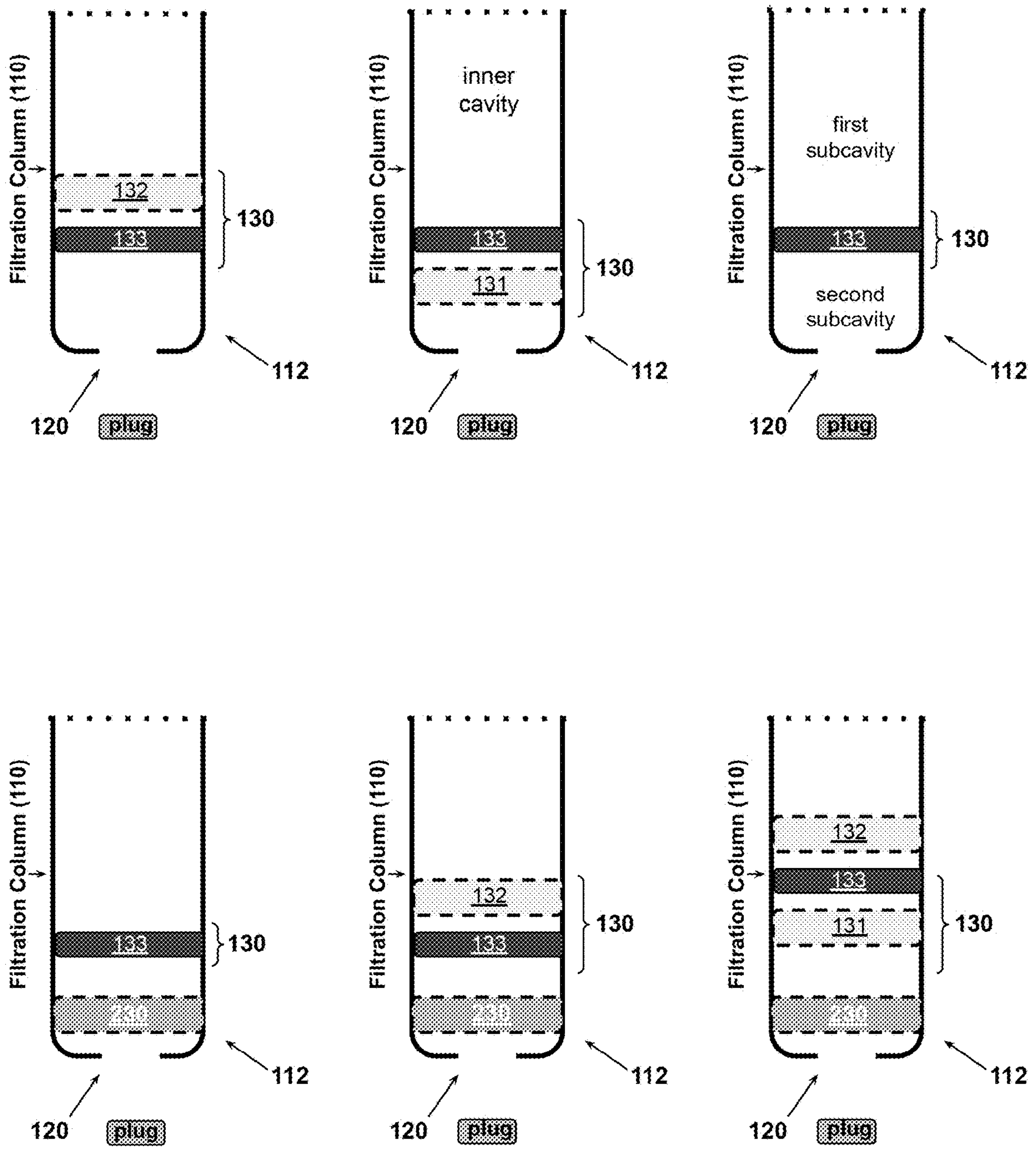
FIG. 1C shows, in accordance with certain embodiments herein, the various configurations of the components (e.g., filtration columns and filter components) of the nucleic acid isolation and extraction system as described herein.
Figure 2:
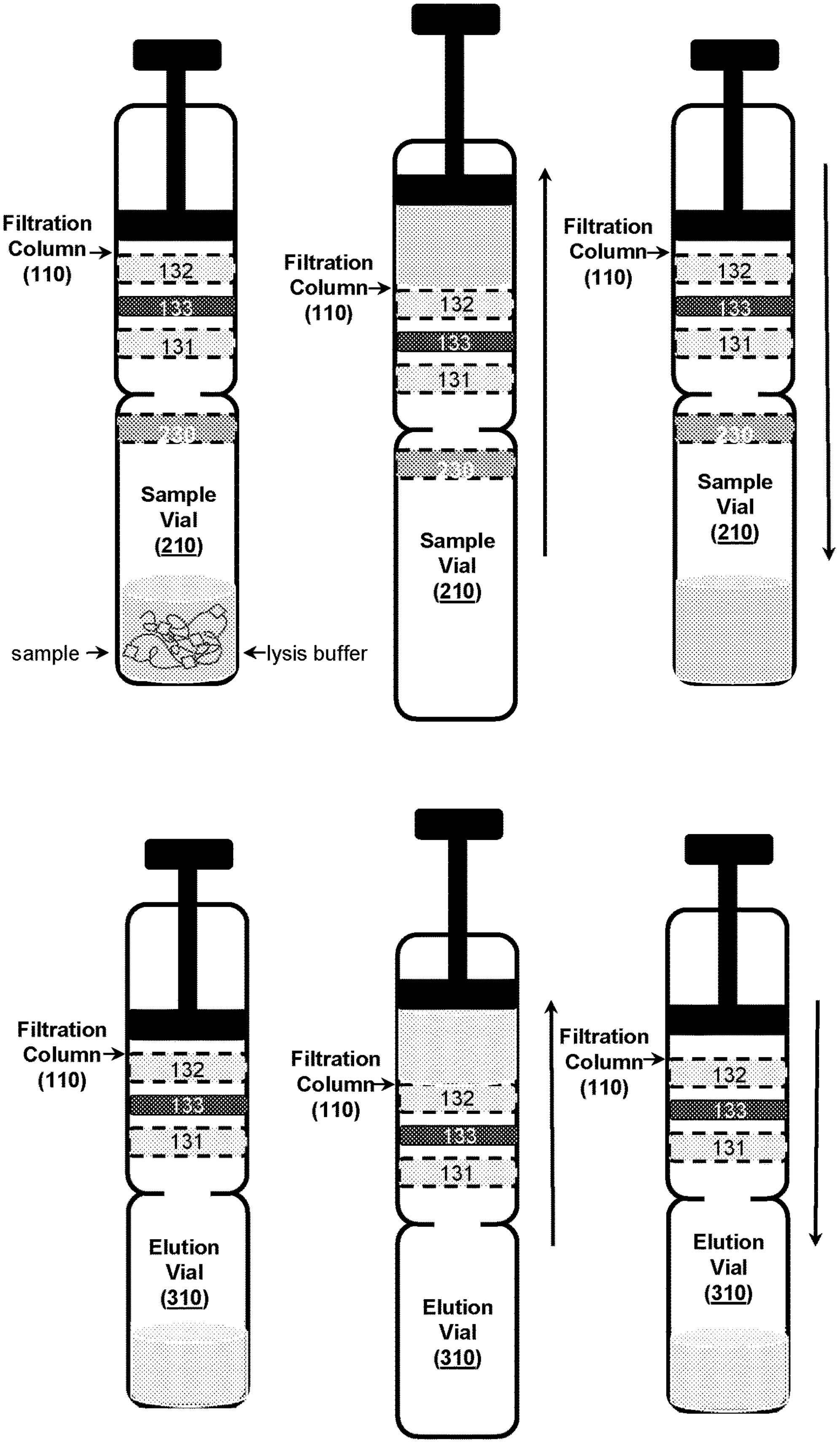
FIG. 2 shows an illustration of the method for isolating and extracting nucleic acids from a sample using a system as described herein.

Systems for Nucleic Acid Extractions:

Referring to FIGS. 1A, 1B, and 1C the present invention features a system for isolating and extracting nucleic acids from a biological sample. In some embodiments, the system comprises a filtration column (110). In some embodiments, the filtration column (110) comprises a first column end (111) and a second column end (112), e.g., opposite the first column end (111). In some embodiments, the first column end (111) comprises a means for providing positive and negative pressure disposed therein, or operably connected to, or a component for attaching a means for providing positive and negative pressure, and the second column end (112) comprises an opening (120), e.g., for insertion of the sample. The system comprises a filter component (130) disposed within the filtration column (110) in between the first column end (111) and the second column end (112).

Referring to FIG. 1C, in some embodiments, the filter component (130) comprises a first filter (131), a second filter (132), and a solid support (133) capable of reversibly binding nucleic acid sandwiched between the first filter (131) and the second filter (132). In some embodiments, the filter component comprises the first filter (131) and the solid support (133). In some embodiments, the first filter (131) is adjacent to or in contact with the solid support (133). In some embodiments, the filter component comprises the second filter (132) and the solid support (133) In some embodiments, the filter component comprises the solid support (133). The solid support (133) (or solid support and filters, depending on the configuration) may be mounted to the inner walls of the filtration column (110) so as to divide the inner cavity of the filtration column (110) into two or more separate and distinct subcavities (e.g., one in between the solid support (133) and the opening (120) and one in between the solid support (133) and the means for providing positive and negative pressure), limiting the flow of fluid between the two cavities through only the solid support (133) or solid support (133) and filters (e.g., (131) and (132)). The filters and solid support (133) are mounted so as to be immobile. In certain embodiments, the first filter (131) and/or second filter (132) help immobilize the solid support (133). In some embodiments, the filter component (130) divides the inner cavity into at least two subcavities wherein a first subcavity is between the filter component (130) and the first column end (111) and a second subcavity is between the filter component (130) and the second column end (112), and fluid passing from the first subcavity to the second subcavity necessarily passes through the filter component (130). In some embodiments, The system further comprises a means for sealing the opening (120). In some embodiments, the system further comprises a plug. In some embodiments, the plug attaches to the opening (120) of the filtration column (110), sealing the opening (120), to create an enclosed system. As used herein, an "enclosed system" refers to a system in which positive and negative pressures are able to build up and move fluid through said system. Additionally, an enclosed system refers to a system that sealed system which prevents leaking of the fluid. Furthermore, an enclosed system refers to a system that allows no air exchange between the system and the outside air (i.e., air will neither be released from the system nor allowed into the system).

In some embodiments, the means for providing positive and negative pressure is a syringe or a similar apparatus. In some embodiments, the syringe is attached to the first column end (111) of the filtration column (110). In other embodiments, the means for providing positive and negative pressure is a syringe comprising a needle. In some embodiments, the needle is inserted through the first column end (111) of the filtration column (110). In other embodiments, the means for providing positive and negative pressure is a plunger (140) slidably coupled to the filtration column (110). In some embodiments, the plunger (140) comprises a first plunger end (141). In some embodiments, the first plunger end (141) is disposed through the first column end (111) and within the filtration column (110).

In some embodiments, the first filter (131) comprises a polyethylene (PET) filter. In some embodiments, the second filter (132) comprises a polyethylene (PET) filter. In other embodiments, the first filter (131) comprises a polypropylene (PP) filter. In other embodiments, the second filter (132) comprises a polypropylene (PP) filter. In further embodiments, the first filter (131) and/or the second filter (132) may comprise other types of filters that are porous and that do not bind to nucleic acids (e.g, DNA).

In some embodiments, the first filter (131) and/or second filter (132) comprise filters having a pore size of 35 μm. In other embodiments, the first filter (131) and/or second filter (132) comprise filters having a pore size of 10 μm. In further embodiments, the first filter (131) and/or second filter (132) comprise filters having a pore size of 90 μm. In some embodiments, the first filter (131) and/or second filter (132) comprise filters having a pore size of about 10 μm to 25 μm, or about 10 μm to 35 μm, or about 10 μm to 45 μm, or about 10 μm to 55 μm, or about 10 μm to 65 μm, or about 10 μm to 75 μm, or about 10 μm to 90 μm, or about 10 μm to 100 μm, or about 10 μm to 150 μm, or about 10 μm to 200 μm, or about 25 μm to 35 μm, or about 25 μm to 45 μm, or about 25 μm to 55 μm, or about 25 μm to 65 μm, or about 25 μm to 75 μm, or about 25 μm to 90 μm, or about 25 μm to 100 μm, or about 25 μm to 150 μm, or about 25 μm to 200 μm, or about 35 μm to 45 μm, or about 35 μm to 55 μm, or about 35 μm to 65 μm, or about 35 μm to 75 μm, or about 35 μm to 90 μm, or about 35 μm to 100 μm, or about 35 μm to 150 μm, or about 35 μm to 200 μm, or about 45 μm to 55 μm, or about 45 μm to 65 μm, or about 45 μm to 75 μm, or about 45 μm to 90 μm, or about 45 μm to 100 μm, or about 45 μm to 150 μm, or about 45 μm to 200 μm, or about 55 μm to 65 μm, or about 55 μm to 75 μm, or about 55 μm to 90 μm, or about 55 μm to 100 μm, or about 55 μm to 150 μm, or about 55 μm to 200 μm, or about 65 μm to 75 μm, or about 65 μm to 90 μm, or about 65 μm to 100 μm, or about 65 μm to 150 μm, or about 65 μm to 200 μm, or about 75 μm to 90 μm, or about 75 μm to 100 μm, or about 75 μm to 150 μm, or about 75 μm to 200 μm, or about 90 μm to 100 μm, or about 90 μm to 150 μm, or about 90 μm to 200 μm, or about 100 μm to 150 μm, or about 100 μm to 200 μm, or about 150 μm to 200 μm. In other embodiments, the first filter (131) and/or second filter (132) comprise filters having a pore size smaller than 10 μm. In further embodiments, the first filter (131) and/or second filter (132) comprise filters having a pore size larger than 200 μm.

In some embodiments, the PET filter comprises a 35 μm PET filter. In other embodiments, the PET filter comprises a 10 μm PET filter. In further embodiments, the PET filter comprises a 90 μm PET filter. In some embodiments, the PP filter comprises a 35 μm PP filter. In other embodiments, the PP filter comprises a 10 μm PP filter. In further embodiments, the PP filter comprises a 90 μm PP filter.

In some embodiments, the solid supports (133) described herein are capable of reversibly binding nucleic acids. Non-limiting examples of solid supports include but are not limited to cellulose, nitrocellulose, modified cellulose, silica, a cotton pad, paper, the like, or combinations thereof. In other embodiments, the solid supports (133) described herein may comprise any material that can reversibly bind to nucleic acids (e.g., DNA). In preferred embodiments, the solid support (133) comprises cellulose or cellulose-based material.

In some embodiments, the filter component (130) comprises one solid support (133). In other embodiments, the filter component (130) comprises a plurality of solid supports (133). In further embodiments, the filter component (130) comprises two solid supports (133), or four solid supports (133), or six solid supports (133), or eight solid supports (133).

Without wishing to limit the present invention to any theory or mechanism, it is believed that nucleic acids (e.g., DNA) bind cellulose better than proteins do; therefore, proteins will be washed out with the rest of the lysis buffer and will not contaminate the sample. This helps provide a sample that has low amounts of protein, e.g., a sample with essentially no protein that would cause interference with downstream assays or analyses.

In some embodiments, the system further comprises a sample vial (210) for containing a biological sample. In certain embodiments, the biological sample is a lysed biological sample. In some embodiments, the biological sample comprises tissue from shrimp, including but not limited to shrimp muscle tissue, shrimp organs (e.g., intestines or liver), shrimp pleopods, or a combination thereof. In other embodiments, the biological sample may comprise aquatic animal tissue, non-aquatic animal tissue, saltwater animal tissue, freshwater animal tissue, animal waste (e.g., feces), plant tissue, bacteria, or yeast. In some embodiments, the biological sample comprises ecological water samples or soil. In further embodiments, the biological sample may include but is not limited to saliva, blood (e.g., whole blood and serum), urine, stool, respiratory samples (e.g., swabs or sputum), cerebrospinal fluid, or amniotic fluid. In some embodiments, the biological sample is obtained from an animal (e.g., a mammal).

The sample vial (210) may comprise an outlet (220) at a second sample vial end (212). In other embodiments, the sample vial (210) comprises a cap comprising an outlet (220). In some embodiments, the cap of the sample vial (210) is disposed at the second sample vial end (212). The outlet (220) and/or cap may be configured to attach to/engage with the opening (120) of the filtration column (110), e.g., for the flow of the sample in the sample vial (210) to the filtration column (110). The sample vial (210) and filtration column (110) may be connected (e.g., temporarily attached) to allow fluid flow between the two, wherein the connection between the two is configured (e.g., sealed) to prevent leaking. In some embodiments, an O-ring may be used to seal the connection between the sample vial (210) and filtration column (110) to prevent leaking. In some embodiments, the sample may be placed directly into the filtration column via the opening (120) without the use and/or connection of the sample vial (210).

The sample vial (210) may feature a prefilter (230) for filtering cell debris, including but not limited to a cell wall, biological contaminants, pieces of ground tissue, or a combination thereof. In some embodiments, the prefilter (230) is integrated into the cap of the sample vial. The prefilter (230) may be configured such that the flow of fluid from the sample vial (210) to outside the sample vial is through only the prefilter (230). In some embodiments, the prefilter (230) is mounted (and immobilized) to the inner walls of the sample vial (230), thereby dividing the inner cavity of the sample vial into two or more subcavities (e.g., one in between the first sample vial end (211) and the prefilter (230) and one in between the prefilter (230) and the sample vial outlet (220)). The prefilter (230) may be configured such that the flow of fluid from one subcavity to the other is through the prefilter (230) only.

The sample vial (210) may comprise a plurality of prefilters (230). In some embodiments, the sample vial (210) comprises one prefilter (230). In other embodiments, the sample vial (210) comprises two prefilters (230). In further embodiments, the sample vial (210) may comprise more than one prefilter (230). A plurality of prefilters (230) may be used in accordance with the present invention as long as the prefilters (230) do not obstruct the flow of fluid from the sample vial (210) to the filtration column (110).

In some embodiments, the prefilter (230) is comprised of any material that does not absorb and/or does not significantly absorb nucleic acids. In some embodiments, the prefilter (230) comprises a polypropylene (PP) mesh filter. In some embodiments, the prefilter (230) comprises a filter having a pore size selected from: 700 μm-200 μm filter. In other embodiments, the prefilter (230) comprises a filter having a pore size selected from: 700 μm-350 μm. In further embodiments, the prefilter (230) comprises a filter having a pore size selected from about 800 μm-50 μm, or about 800 μm-200 μm, or about 800 μm-350 μm, or about 800 μm-500 μm, or about 800 μm-650 μm, or about 650 μm-50 μm, or about 650 μm-200 μm, or about 650 μm-350 μm, or about 650 μm-500 μm, or about 500 μm-50 μm, or about 500 μm-200 μm, or about 500 μm-350 μm, or about 350 μm-50 μm, or about 350 μm-200 μm, or about 200 μm-50 μm. In some embodiments, the prefilter (230) is removable.

In certain embodiments, the filtration column (110) may feature a prefilter (230). In some embodiments, the prefilter (230) is mounted (and immobilized) to the inner walls of the filtration column (110), thereby dividing the inner cavity of the sample vial into two or more subcavities (e.g., one in between the first column end (111) of the filtration column (110) and the prefilter (230) and one in between the prefilter (230) and the opening (120)). In some embodiments, a filter component (130) is disposed within a subcavity of the filtration column (e.g., a filter component (130) may be disposed between the first column end (111) of the filtration column (110) and the prefilter). The prefilter (230) may be configured such that the flow of fluid from one subcavity to the other is through the prefilter (230) only.

In some embodiments, the system further comprises an elution vial (310) comprising an outlet (320) at a second elution vial end (312). In some embodiments, the opening (120) of the filtration column (110) attaches to or engages the outlet (320) of the elution vial (310) to create an enclosed system, wherein fluid from the elution vial (310) can flow to the filtration column (110). The elution vial (310) and filtration column (110) may be sealed together (e.g., temporarily attached, engaged) such that fluid can flow between the two and in a sealed manner so as to prevent leaking. In some embodiments, the elution vial (310) further comprises an elution buffer.

Referring to FIGS. 2, 3, 4, 5, and 6, the present invention features a method of isolating and extracting nucleic acids from a biological sample. In some embodiments, the method comprises attaching a sample vial as described herein comprising a lysed biological sample to a filter column as described herein to create an enclosed system. In some embodiments, the method comprises creating negative pressure within the filtration column (110) to pull the lysed biological sample from the sample vial (120), through the prefilter (230), and through the filter component (130), into the first column end (111) of the filtration column (110). In some embodiments, the method comprises creating a positive pressure with the filtration column (110) to push the lysed biological sample through the filter component (130) and back into the sample vial (210). In some embodiments, the method comprises removing the sample vial (210) and attaching an elution vial (310) as described herein comprising an elution buffer to the filter column to create an enclosed system. In some embodiments, the method comprises creating negative pressure within the filtration column (110) to pull the elution buffer through the filter component (120) and into the first column end (112) of the filtration column (110). In some embodiments, the method comprises creating positive pressure within the filtration column (110) to push the elution buffer through the filter component (130) and back into the elution vial (310).

The present invention is not limited to the steps in the methods described above. For example, in some embodiments, the sample vial (210) is removed after the sample solution from the sample vial (210) is drawn past the prefilter (230) and solid support (133), e.g., so as to remove the prefilter (230) that may be laden with cellular debris and possibly even clogged. In some embodiments, an empty vial (e.g., a vial similar to the sample vial but without the prefilter (230)) or a second empty sample vial (210) is connected to the filtration column (110) and the sample solution may be drawn back and forth between the empty vial and filtration column (110), e.g., allowing the sample solution additional passages through the solid support (133), e.g., to help increase nucleic acid yield.

In some embodiments, the method comprises pulling and pushing the elution buffer through the filter component (130) 1-20 times. In some embodiments, the method comprises pulling and pushing the elution buffer through the filter component (130) 2-10 times. In other embodiments, the method comprises pulling and pushing the elution buffer through the filter component (130) 3-5 times.

In some embodiments, the present invention features a system for isolating nucleic acids from a biological sample. In some embodiments, the system comprises a filtration column (110) comprising a first column end (111) and a second column end (112). In some embodiments, the first column end (111) comprises a means for providing positive and negative pressure disposed therein, and the second column end (112) comprises an opening (120). In some embodiments, the filtration column (110) comprises a filter component (130) disposed within the filtration column (110). In some embodiments, the filter component comprises a first filter (131), a second filter (132), and a solid support (133) capable of reversibly binding nucleic acid sandwiched between the first filter (131) and the second filter (132). In some embodiments, the system comprises a sample vial (210) comprising an outlet (220) at a second sample vial end (212). In some embodiments, the opening (120) of the filtration column (110) attaches to the outlet (220) of the sample vial (210) to create an enclosed system.

In some embodiments, the present invention features a method for isolating nucleic acids from a biological sample. In some embodiments, the method comprises obtaining a system comprising a filtration column (110) attached to a sample vial (210) to create an enclosed system as described herein (i.e., an opening (120) of a filtration column (110) attached to an outlet (220) of a sample vial (210) to create an enclosed system). In some embodiments, the method comprises creating negative pressure within the filtration column (110) to pull the lysed biological sample from the sample vial (210) through the prefilter (230) and through the filter component (130), into the first column end (111) of the filtration column (110). In some embodiments, the method comprises creating a positive pressure within the filtration column (110) to push the lysed biological sample through the filter component (130) and back into the sample vial (210). In some embodiments, the nucleic acids are isolated and reversibly bound to the solid support (133) of the filter component (120).

In other embodiments, the present invention features a system for the extraction of nucleic acids from a biological sample. In some embodiments, the system comprises a filtration column (110) comprising a first column end (111) and a second column end (112). In some embodiments, the first column end (111) comprises a means for providing positive and negative pressure disposed therein, and the second column end (112) comprises an opening (120). In some embodiments, the filtration column (110) comprises a filter component (130) disposed within the filtration column (110). In some embodiments, the filter component comprises a first filter (131), a second filter (132), and a solid support (133) capable of reversibly binding nucleic acid sandwiched between the first filter (131) and the second filter (132), an elution vial (310) comprising an outlet (320) at a second elution vial end (312). In some embodiments, the opening (120) of the filtration column (110) attaches to the outlet (320) of the elution vial (310) to create an enclosed system. In other embodiments, a blunt needle is attached to the opening (120) of the filtration column (110), and the needle is inserted into the second elution vial end (312) of the elution vial to create an enclosed system. In some embodiments, the blunt needle is removable.

In some embodiments, the present invention features a method for extracting nucleic acids from a biological sample. In some embodiments, the method comprises obtaining a system comprising a filtration column (110) attached to an elution vial (210) to create an enclosed system as described herein (e.g., an opening (120) of a filtration column (110) attached to an outlet (320) of an elution vial (310) to create an enclosed system). In some embodiments, the method comprises creating negative pressure within the filtration column (110) to pull the elution buffer from the elution vial (320) through the filter component (130), into the first column end (111) of the filtration column (110). In some embodiments, the method comprises creating a positive pressure within the filtration column (110) to push the elution buffer through the filter component (130) and back into the elution vial (310). In some embodiments, the method comprises pulling and pushing the elution buffer through the filter component (130) 1-20 times. In some embodiments, the elution buffer comprises the extracted nucleic acids.

The present invention provides sample processing methods for isolating and extracting genomic nucleic acids (e.g., gDNA) from a biological sample. In some embodiments, the method can collect genomic nucleic acids (e.g., gDNA) from the sample at a concentration of 270 ng/μl. In other embodiments, the method can collect genomic nucleic acids (e.g., gDNA) from a sample at a concentration of about 50-2000 ng/μl, or about 200-2000 ng/μl, or about 350-2000 ng/μl, or about 500-2000 ng/μl, or about 650-2000 ng/μl, or about 800-2000 ng/μl, or about 950-2000 ng/μl, or about 1100-2000 ng/μl, or about 1300-2000 ng/μl, or about 1500-2000 ng/μl, or about 50-1500 ng/μl, or about 200-1500 ng/μl, or about 350-1500 ng/μl, or about 500-1500 ng/μl, or about 650-1500 ng/μl, or about 800-1500 ng/μl, or about 950-1500 ng/μl, or about 1100-1500 ng/μl, or about 1300-1500 ng/μl, or about 50-1300 ng/μl, or about 200-1300 ng/μl, or about 350-1300 ng/μl, or about 500-1300 ng/μl, or about 650-1300 ng/μl, or about 800-1300 ng/μl, or about 950-1300 ng/μl, or about 1100-1300 ng/μl, or about 50-1100 ng/μl, or about 200-1100 ng/μl, or about 350-1100 ng/μl, or about 500-1100 ng/μl, or about 650-1100 ng/μl, or about 800-1100 ng/μl, or about 950-1100 ng/μl, or about 50-950 ng/μl, or about 200-950 ng/μl, or about 350-950 ng/μl, or about 500-950 ng/μl, or about 650-950 ng/μl, or about 800-950 ng/μl, or about 50-800 ng/μl, or about 200-800 ng/μl, or about 350-800 ng/μl, or about 500-800 ng/μl, or about 650-800 ng/μl, or about 50-650 ng/μl, or about 200-650 ng/μl, or about 350-650 ng/μl, or about 500-650 ng/μl, or about 50-500 ng/μl, or about 200-500 ng/μl, or about 350-500 ng/μl, or about 50-350 ng/μl, or about 200-350 ng/μl, or about 50-200 ng/μl. In further embodiments, the method can collect genomic nucleic acids (e.g., gDNA) from a sample at a concentration of greater than 2000 ng/μl.

In some embodiments, the method can collect 500-2500 ng of genomic nucleic acids (e.g., gDNA) per mg of a biological sample (e.g., tissue). In other embodiments, the method can collect about 500-2500 ng, or about 500-2000 ng, or about 500-1500 ng, or about 500-1000 ng, or about 1000-2500 ng, or about 1000-2000 ng, or about 1000-1500, or about 1500-2500 ng, or about 1500-2000 ng, or about 2000-2500 ng of genomic nucleic acids (e.g., gDNA) per mg of a biological sample (e.g., tissue).

In some embodiments, the genomic nucleic acids comprise genomic DNA or genomic RNA. The genomic RNA may comprise mRNA or RNA from an RNA-virus.

In some embodiments, the sample is a processed sample. In some embodiments, the processed sample comprises ground tissue in a lysis buffer. In other embodiments, the biological sample is a processed biological sample. In some embodiments, the processed biological sample comprises ground tissue in a lysis buffer.

In some embodiments, the method comprises introducing the sample to a sample vial (210). In other embodiments, the method comprises introducing the biological sample to a sample vial (210). In some embodiments, the sample is housed in a sample vial (210). In other embodiments, the biological sample is housed in a sample vial (210). In some embodiments, the sample vial (210) comprises a cap. In some embodiments, a prefilter (230) is disposed within the cap. In some embodiments, the prefilter (230) in the cap of the sample vial (210) is a mesh filter. In some embodiments, the cap of the sample vial (210) comprises two mesh filters therein. In some embodiments, the cap is an attachable cap. In some embodiments, the cap can be secured to the sample vial (210) to prevent leakage. In some embodiments, the cap can be welded or glued to the sample vial (210) to prevent leakage. In other embodiments, the cap attached to the sample vial (210) comprises an O-ring to prevent leakage. In some embodiments, the sample vial (210) is attachable to a filtration column (110), such that the opening (120) of the filtration column (110) attaches to the cap of the sample vial (210).

In some embodiments, the cap of the sample vial (210) may be a luer-lock cap. In some embodiments, the cap of the sample vial (210) may comprise a luer-lock fitting. In some embodiments, the luer lock fitting is a female Luer lock fitting. In other embodiments, luer lock fitting is a male Luer lock fitting. In this embodiment, the cap of the filtration column (110) may also be a luer-lock cap. In some embodiments, the cap of the filtration column (110) may comprise a luer-lock fitting. In some embodiments, the luer lock fitting is a female Luer lock fitting. In other embodiments, luer lock fitting is a male Luer lock fitting. In preferred embodiments, the luer-lock cap of the sample vial (210) is attachable to the luer-lock cap of the filtration column (110).

In some embodiments, the method comprises connecting a sample vial (210) with a sample therein to a filtration column (110). In other embodiments, the method comprises connecting a sample vial (210) with a biological sample therein to a filtration column (110).

In some embodiments, the filtration column (110) comprises a column and a filter component (130) therein. In some embodiments, the filter component (130) of the filtration column (110) comprises a polyethylene (PET) filter and a cellulose filter. In other embodiments, the filter component (130) of the filtration column (110) comprises a cellulose filter sandwiched between two PET filters. In some embodiments, the filtration column (110) further comprises a cap at a first column end (111) and an opening (120) at a second column end (112), wherein the filter component (130) is disposed in between the opening (120) and the cap. In other embodiments, the filtration column (110) further comprises a cap with a septa at a first column end (111) and an opening (120) at a second column end (112), wherein the filter component (130) is disposed in between the opening (120) and the cap with a septa.

In some embodiments, the cap is not removable. In other embodiments, the cap with septa is not removable. In some embodiments, the cap is removable. In other embodiments, the cap with septa is removable. In some embodiments, the cap is secured to the filtration column (110) to prevent leakage. In other embodiments, the cap with septa is secured to the filtration column (110) to prevent leakage. In some embodiments, the cap is secured to the filter column to maintain pressure. In other embodiments, the cap with septa is secured to the column to maintain pressure. In some embodiments, the septa allows a syringe needle therethrough. In some embodiments, the septa may be removed from the cap.

In some embodiments, methods described herein further comprise introducing a syringe through the septa and via the syringe pulling the sample from the sample vial (210) through at least the filter component (130) of the filtration column (110). In some embodiments, methods described herein further comprise pushing the sample through at least the filter component (110) of the filter column (130) via the syringe. In some embodiments, the aforementioned steps are repeated one or more times.

In some embodiments, the methods described herein further comprise eluting nucleic acids (e.g., DNA) collected by the filter component (130) of the filtration column (110). In some embodiments, the elution buffer is introduced to the filter component (130) of the filtration column (110). In some embodiments, a needle is attached to the opening (120) of the filtration column (110) and placed in an elution vial (310) comprising an elution buffer. In some embodiments, the elution buffer is introduced to the filtration column (110) via pulling the syringe. In some embodiments, the elution buffer is pushed from the filter column into an elution vial via the syringe. In some embodiments, the elution buffer comprises genomic DNA collected from the sample.

In some embodiments, the present invention features a filtration column (110) comprising a first column end (111), a second column end (112), and a filter component (130) disposed therein. In some embodiments, the first column end (111) comprises a means for providing positive and negative pressure disposed therein, and the second column end (112) comprises an opening (120).

In some embodiments, the filter component (130) comprises a first filter (131). In some embodiments, the filter component (130) comprises a first filter (131) and a solid support (133). In some embodiments, the filter component (130) comprises a solid support sandwiched between a first filter (131) and a second filter (132). In some embodiments, the solid support is capable of reversibly binding nucleic acids. In some embodiments, the solid support is cellulose. In some embodiments, the first filter and the second filter are polyethylene (PET) filters. In some embodiments, the PET is a 35 μm filter.

In some embodiments, the present invention features a method of isolating and extracting nucleic acids from a sample. In some embodiments, the method comprises obtaining a tissue sample. In some embodiments, the method comprises lysing the tissue sample, wherein the lysed sample is in an enclosed sample vial (210). In some embodiments, the method comprises attaching a filtration column (110) to the enclosed sample vial (210). In some embodiments, the filtration column (110) comprises a filter component (130). In some embodiments, the filtration column (110) is enclosed with a cap and a rubber septa. In some embodiments, the filtration column (110) attaches to a screw-on cap with a prefilter (230) on the enclosed sample vial (210). In some embodiments, the method comprises inserting a syringe through the rubber septa-connected cap of the filtration column (110) connected to the enclosed sample vial (210). In some embodiments, the method comprises creating a vacuum in the filtration column (110) using the syringe. In some embodiments, the method comprises pulling the lysed tissue sample from the enclosed sample vial (210) through the filter component (130) into the filtration column (110). In some embodiments, the method comprises pushing the lysate from the filtration column (110) through the filter component (130) and into the enclosed sample vial (210). In some embodiments, the method comprises detaching the sample vial (210) from the filtration column (110). In some embodiments, the method comprises attaching a blunt needle to a second column end (112) of the filtration column (110). In some embodiments, the method comprises inserting the blunt needle into an elution vial (310) comprising an elution buffer. In some embodiments, the method comprises pulling the elution buffer from the elution vial (310) through the filter component (130) into the filtration column (110). In some embodiments, the method comprises pushing the elution buffer from the filtration column (110) through the filter component (130) and into the elution vial (310).

In some embodiments, the elution buffer is pulled and pushed through the filter component (130) one or more times. In some embodiments, the elution buffer is pulled and pushed through the filter component (130) at least 1 to 20 times. In some embodiments, the elution buffer is pulled and pushed through the filter component (130) at least 3 to 10 times. In other embodiments, the elution buffer is pushed through the filter component (130) at least 3 to 8 times. In further embodiments, the elution buffer is pushed through the filter component (130) at least 3 to 5 times.

The present invention features various embodiments of devices and methods for use of said device in isolating and extracting nucleic acids from a biological sample. For example, referring to FIG. 3, the present invention may feature a sample vial (210) comprising one or more prefilters (230; e.g., steel mesh filters), a biological sample, and a lysis buffer (see (1.) of FIG. 3); and a filtration column (110) comprising a septa-connected cap and a filter component (130; e.g., two 35 um PET filters and 1 cellulose filter) (see (2.) of FIG. 3). The filtration column (110) may be fitted to the second sample vial end (212) and tightened with parafilm (see (3.) of FIG. 3). A 1 mL syringe made with polypropylene (PP) connected to a fixed 30-gauge sharp needle (see (4.) of FIG. 3) is inserted through the luer-lock cap on the filtration column (110). The syringe goes through the luer-lock cap on the first column end (111) of the filtration column (110) connected to the sample vial (210) (see (5.) of FIG. 3) and the lysate is pulled through the filter component (130) and then pushed out, the force of which removes the unbound protein from the cellulose filter (see (6.) of FIG. 3). The sample vial (220) is removed from the filtration column (110) and a disposable pipette tip is placed on the second column end (112) of the filtration column (110) (see (7.) of FIG. 3)). In the embodiment shown in FIG. 3, the elution vial (310) is a 1.5 mL centrifuge tube containing the elution buffer (see (8.) of FIG. 3)). The elution buffer is pulled up through the filter component (e.g., the cellulose) (see (9.) of FIG. 3) and then the elution buffer is pushed out through the filter component (130; e.g., the cellulose) back into the elution vial (310) (see (10.) of FIG. 3). The process of pulling and pushing out the elution buffer through the filter component (130; e.g., the cellulose) is repeated one or more times. The force helps to elute the gDNA into the elution vial (310) (see (11.) of FIG. 3).

Referring to FIG. 4, the present invention may features a sample vial (210) comprising one or more prefilters (230; e.g., two polypropylene (PP) mesh filters), a biological sample, and a lysis buffer (see (1.) of FIG. 4) and filtration column (110) comprising a septa-fused cap and a filter component (130; e.g., two 35 um PET filters and 2 cellulose filter) (see (2.) of FIG. 4). The filtration column (110) is fitted to the second sample vial end (212) and tightened with parafilm (see (3.) of FIG. 4). A 1 mL syringe made with polypropylene (PP) connected to a fixed 30-gauge sharp needle (see (4.) of FIG. 4). The syringe goes through the septa-fused cap on the first column end (111) of the filtration column (110) connected to the sample vial (210) (see (5.) of FIG. 4). The system is then flipped, e.g., such that the syringe is positioned downward and the syringe is pulled to create a vacuum in the filtration column (110). The lysate is pulled through the filter component (130) and then pushed out, the force of which removes the unbound protein from the cellulose filter (see (6.) of FIG. 4). The system is then flipped again and the lysate is pushed out of the filtration column (130), unclogging the debris if stuck on the first filter (131) or the second filter (132). As protein does not bind strongly to the solid support (133; e.g., cellulose), the force of the lysate moving through the filter component (130) removes the protein from the filter component (130), leaving the nucleic acids (e.g., gDNA) bound to the solid support (133; e.g., cellulose). This process may be repeated one or more times until the entire lysate is pulled through the filter component (130) and pushed back out (i.e., pushed back into the sample vial (210)). The sample vial (220) is removed from the filtration column (110) and an 18 gauge blunt needle is fitted on the filtration column (110) (see (7.) of FIG. 4). In this particular embodiment shown in FIG. 4, the elution vial (310) is made with polypropylene (PP) with a septa cap and contains an elution buffer (see (8.) of FIG. 4). The elution buffer is pulled up through the filter component (e.g., the cellulose) (see (9.) of FIG. 4) and the elution buffer is pushed out through the filter component (130; e.g., the cellulose) back into the elution vial (310) (see (10.) of FIG. 4). The process of pulling and pushing out the elution buffer through the filter component (130; e.g., the cellulose) is repeated one or more times. The force helps to elute the gDNA into the elution vial (310) (see (11.) of FIG. 4).

Referring to FIG. 5, the present invention may feature a conical sample vial (210) comprising one or more prefilters (230; e.g., a polypropylene (PP) mesh filter), a biological sample, a lysis buffer, and a luer-lock cap with an O-ring inside to help seal the system (see (1.) of FIG. 5) and a filtration column (110) comprising luer-lock cap with an O-ring to help with sealing and pressure and a filter component (130; e.g., two 35 um PET filters and 4 cellulose filters) (see (2.) of FIG. 5). The filtration column (110) is fitted to the second sample vial end (212) and tightened with parafilm (see (3.) of FIG. 5). A needleless syringe (varying in size; e.g., 5 mL) made with polypropylene (PP) and comprising luer-lock threading (see (4.) of FIG. 5) is locked into place with the luer-lock cap on the first column end (111) of the filtration column (110) connected to the sample vial (210). The system is then flipped, e.g., such that the syringe plunger is positioned downward, and the syringe is pulled to create a vacuum in the filtration column (110). The lysate (i.e., the lysed biological sample) is pulled from the sample vial (210) and through the filter component (130; e.g., the first filter (131) and the second filter (132), which separates the cell debris; and the solid surface (133; e.g., the cellulose filter, which binds the nucleic acid (e.g., gDNA)) (see (5.) of FIG. 5). The system is then flipped again and the lysate is pushed out of the filtration column (130), unclogging the debris if stuck on the first filter (131) or the second filter (132). As protein does not bind strongly to the solid support (133; e.g., cellulose), the force of the lysate moving through the filter component (130) removes the protein from the filter component (130), leaving the nucleic acids (e.g., gDNA) bound to the solid support (133; e.g., cellulose) (see (6.) of FIG. 5). This process may be repeated one or more times until the entire lysate is pulled through the filter component (130) and pushed back out (i.e., pushed back into the sample vial (210)). The sample vial (210) is removed from the filtration column (110) and a blunt needle is placed on the second column end (112) of the filtration column (110) (see (7.) of FIG. 5). In this particular embodiment, the elution vial (310) is made with polypropylene (PP) with a septa cap and contains an elution buffer (see (8.) of FIG. 5). The elution buffer is pulled up through the filter component (130; e.g., the cellulose)(see (9.) of FIG. 5) and the elution buffer is pushed out through the filter component (130; e.g., the cellulose) back into the elution vial (310) (see (10.) of FIG. 5). The process of pulling and pushing out the elution buffer through the filter component (130; e.g., the cellulose) is repeated one or more times. The force helps to elute the gDNA into the elution vial (310) (see (11.) of FIG. 5).

Referring to FIG. 6, the present invention may feature a conical sample vial (210) comprising one or more prefilters (230; e.g., a polypropylene (PP) mesh filter), a biological sample, a lysis buffer, and a luer-lock cap with parafilm or an O-ring inserted into the cap to help seal the system (see (1.) of FIG. 6). In the embodiment shown in FIG. 6 a needleless syringe is the filtration column (110) and comprises a filter component (130; e.g., two 35 um PET filters and 4 cellulose filters) (see (2.) of FIG. 6). In some embodiments, the needleless syringe (i.e., the filtration column (110)) comprises a filter component (130) disposed therein. The filter component (130) may comprise a first filter (131; e.g., 35 μm PET filter), a second filter (132; e.g., 35 μm PET filter), and four solid supports (133; e.g., four cellulose filter punches) capable of reversibly binding nucleic acid sandwiched between the first filter (131) and the second filter (132)). The needleless syringe is fitted to a conical sample vial (210) comprising one or more prefilters (230; e.g., a polypropylene mesh filter), a luer-lock cap with either parafilm or an O-ring inserted into the cap, a biological sample, and a lysis buffer (see (3.) of FIG. 6). The system is then flipped, e.g., such that the syringe plunger is positioned downward, and the syringe is pulled to create a vacuum in the filtration column (110). The lysate (i.e., the lysed biological sample) is pulled from the sample vial (210) and through the filter component (130; e.g., the first filter (131) and the second filter (132), which separates the cell debris; and the solid surface (133; e.g., the cellulose filter, which binds the nucleic acid (e.g., gDNA)). The system is then flipped again, and the lysate is pushed out of the filtration column (130), unclogging the debris if stuck on the first filter (131) or the second filter (132). As protein does not bind strongly to the solid support (133; e.g., cellulose), the force of the lysate moving through the filter component (130) removes the protein from the filter component (130), leaving the nucleic acids (e.g., gDNA) bound to the solid support (133; e.g., cellulose) (see (4.) of FIG. 6). This process may be repeated one or more times until the entire lysate is pulled through the filter component (130) and pushed back out (i.e., pushed back into the sample vial (210)). The sample vial (220) is removed from the filtration column (110) and a blunt needle is placed on the filtration column (110) (see (5.) of FIG. 6). In this particular embodiment, the elution vial (310) is made with polypropylene (PP) with a septa cap and contains an elution buffer (see (6.) of FIG. 6). The elution buffer is pulled (see (7.) of FIG. 6) and pushed (see (8.) of FIG. 6) through the filter component (130). This process of pulling and pushing the elution buffer through the filtration column (130) one or more times. The force may help to elute the nucleic acids (e.g., gDNA) into the elution vial (310) (see (9.) of FIG. 6).

Devices for Nucleic Acid Extractions:

The present invention features a device for isolating and extracting nucleic acids from a biological sample.

Referring to FIGS. 12, 14A, and 14B, the present invention features a device for isolating and extracting nucleic acids from a biological sample. The device may comprise a sample vial (1210), a first collection tube (1410), an elution vial (1310), an elution tube (1610), and a filter component (130). In some embodiments, the sample vial (1210) comprises a sample vial opening (1220) is disposed at second sample vial end (1212) and a sample vial outlet (1221) disposed at a first sample vial end (1211). In some embodiments, the first collection tube (1410) comprises an inlet (1421) at a first collection tube end (1411) and a second collection tube end (1412) comprising a means for providing positive and negative pressure disposed therein. The inlet (1421) of the first collection tube (1410) is fluidly connected to the sample vial outlet (1221). In some embodiments, the elution vial (1310) comprising an elution vial opening (1320) disposed at a second elution vial end (1312) and an first elution end (1311). In some embodiments, the elution tube (1610) comprising a inlet (1621) at a first elution tube end (1611) and a second elution tube end (1612) comprising a means for providing positive and negative pressure disposed therein. The inlet (1621) of the elution tube (1610) is fluidly connected to the elution vial opening (1320). In some embodiments, the filter component (1130) positioned between all of: the sample vial (1210), the sample tube (141), the elution vial (1310), and the elution tube (1610) such that fluid (e.g., a biological sample or elution buffer) moving between the sample vial and sample tube or between the sample tube and elution tube or between the elution tube and elution vial necessarily passes through the filter component (1130). In some embodiments, the devices (1000) described herein are an enclosed system.

Referring to FIG. 16, the present invention features a modular device (1000) for isolating and extracting nucleic acids from a biological sample. The device (1000) may comprise a sample vial (1210), a hub (1510), an elution vial (1310), and a filter component (1130). In some embodiments, the sample vial (1210) comprises a sample vial opening (1220) disposed at a second sample vial end (1212) and a sample vial outlet (1221) disposed at a first sample vial end (1211). In some embodiments, the hub (1510) comprises an opening (1520). In some embodiments, the elution vial (1310) comprises an elution vial opening (1320) disposed at a second elution vial end (1312) and an first elution end (1311). The hub (1510) may be and is fluidly connected to the sample vial outlet (1221) and fluidly connected to the elution vial opening (1320). In some embodiments, the filter component (1130) positioned between all of: the sample vial (1210), the hub (1510), and the elution vial such that fluid moving between the sample vial (1210) and hub (1510) or between the hub (1510) and elution vial (1310) necessarily passes through the filter component (1130).

The device (1000; e.g., the modular device) may further comprise a first collection tube (1410). The first collection tube (1410) may comprise an inlet (1421) at a first collection tube end (1411), a second collection tube end (1412) and a means for providing positive and negative pressure disposed therein. In some embodiments, the means for providing positive and negative pressure in the first collection tube (1410) is a plunger (1440) slidably coupled to the second collection tube end (1412). The plunger (1440) may comprise a first plunger end (1441); which may be disposed through the second collection tube end (1412) and within the collection tube (1410).

In some embodiments, the inlet (1421) at the first collection tube end (1411) may be reversibly attached to the opening (1520) of the hub (1510). In some embodiments, the inlet (1421) at the first collection tube end (1411) fluidly connects to the opening (1520) of the hub (1510). The inlet (1421) at the first collection tube end (1411) may comprise a Luer lock fitting. In some embodiments, the Luer lock fitting is a male Luer lock fitting. In other embodiments, the Luer lock fitting is a female Luer lock fitting.

The device (1000; e.g., the modular device) may further comprise an elution tube (1610). The elution tube (1610) may comprise a inlet (1621) at a first elution tube end (1611), a second elution tube end (1612) and a means for providing positive and negative pressure disposed therein. In some embodiments, the means for providing positive and negative pressure in the elution tube (1610) is a plunger (1640) slidably coupled to the second elution tube end (1612). The plunger (1640) may comprise a first plunger end (1641); which may be disposed through the second elution tube end (1612) and within the elution tube (1610).

In some embodiments, the inlet (1621) at the first elution tube end (1611) may be reversibly attached to the opening (1520) of the hub (1510). In some embodiments, the inlet (1621) at the first elution tube end (1611) fluidly connects to the opening (1520) of the hub (1510). The inlet (1621) at the first elution tube end (1611) may comprise a Luer lock fitting. In some embodiments, the Luer lock fitting is a male Luer lock fitting. In other embodiments, the Luer lock fitting is a female Luer lock fitting.

In some embodiments, the first collection tube (1410) and the elution tube (1610) are removable. In some embodiments, the first collection tube (1410) and the elution tube (1610) are interchangeable. The device (1000) described herein (e.g., the modular device) is configured such that only the sample tube (1410) or the elution tube (1610) is fluidly connected to the opening (1520) of the hub (1510) at a given time.

The filter component (1130) comprises a solid support (1133) adapted to reversibly bind nucleic acid. In some embodiments, the filter component (1130) comprises a first filter (1131), a second filter (1132), and a solid support (1133) capable of reversibly binding nucleic acid sandwiched between the first filter (1131) and the second filter (1132). In some embodiments, the filter component (1130) comprises the first filter (1131) and the solid support (1133). In some embodiments, the filter component (1130) comprises the second filter (1132) and the solid support (1133). The filter component (1130) comprising a solid support (1133) and a filter (e.g., a first filter (1131) or a second filter (1132)) may be configured such that the filter (e.g., a first filter (1131) or a second filter (1132)) is adjacent to or in contact with the solid support (1133).

In some embodiments, the filter component (1130) comprises one solid support (1133). In other embodiments, the filter component (1130) comprises a plurality of solid supports (1133). In further embodiments, the filter component (1130) comprises two solid supports (1133), or four solid supports (1133), or six solid supports (1133), or eight solid supports (1133).

In some embodiments, the solid supports (1133) described herein are capable of reversibly binding nucleic acids. Non-limiting examples of solid supports (1133) include but are not limited to cellulose, nitrocellulose, modified cellulose, silica, a cotton pad, paper, the like, or combinations thereof. In other embodiments, the solid supports (1133) described herein may comprise any material that can reversibly bind to nucleic acids (e.g., DNA). In preferred embodiments, the solid support (133) comprises cellulose or cellulose-based material.

In some embodiments, the first filter (1131) comprises a polyethylene (PET) filter. In some embodiments, the second filter (1132) comprises a polyethylene (PET) filter. In other embodiments, the first filter (1131) and/or the second filter (1132) comprise a polypropylene (PP) filter. In further embodiments, the first filter (131) and/or the second filter (132) may comprise other types of filters that are porous and that do not bind to nucleic acids (e.g., DNA).

In some embodiments, the PET filter comprises a 35 μm PET filter. In other embodiments, the PET filter comprises a 10 μm PET filter. In further embodiments, the PET filter comprises a 90 μm PET filter. In some embodiments, the PP filter comprises a 35 μm PP filter. In other embodiments, the PP filter comprises a 10 μm PP filter. In further embodiments, the PP filter comprises a 90 μm PP filter.

In some embodiments, the first filter (1131) and/or second filter (1132) comprise filters having a pore size of 35 μm. In other embodiments, the first filter (1131) and/or second filter (1132) comprise filters having a pore size of 10 μm. In further embodiments, the first filter (1131) and/or second filter (1132) comprise filters having a pore size of 90 μm. In some embodiments, the first filter (1131) and/or second filter (1132) comprise filters having a pore size of about 10 μm to 25 μm, or about 10 μm to 35 μm, or about 10 μm to 45 μm, or about 10 μm to 55 μm, or about 10 μm to 65 μm, or about 10 μm to 75 μm, or about 10 μm to 90 μm, or about 10 μm to 100 μm, or about 10 μm to 150 μm, or about 10 μm to 200 μm, or about 25 μm to 35 μm, or about 25 μm to 45 μm, or about 25 μm to 55 μm, or about 25 μm to 65 μm, or about 25 μm to 75 μm, or about 25 μm to 90 μm, or about 25 μm to 100 μm, or about 25 μm to 150 μm, or about 25 μm to 200 μm, or about 35 μm to 45 μm, or about 35 μm to 55 μm, or about 35 μm to 65 μm, or about 35 μm to 75 μm, or about 35 μm to 90 μm, or about 35 μm to 100 μm, or about 35 μm to 150 μm, or about 35 μm to 200 μm, or about 45 μm to 55 μm, or about 45 μm to 65 μm, or about 45 μm to 75 μm, or about 45 μm to 90 μm, or about 45 μm to 100 μm, or about 45 μm to 150 μm, or about 45 μm to 200 μm, or about 55 μm to 65 μm, or about 55 μm to 75 μm, or about 55 μm to 90 μm, or about 55 μm to 100 μm, or about 55 μm to 150 μm, or about 55 μm to 200 μm, or about 65 μm to 75 μm, or about 65 μm to 90 μm, or about 65 μm to 100 μm, or about 65 μm to 150 μm, or about 65 μm to 200 μm, or about 75 μm to 90 μm, or about 75 μm to 100 μm, or about 75 μm to 150 μm, or about 75 μm to 200 μm, or about 90 μm to 100 μm, or about 90 μm to 150 μm, or about 90 μm to 200 μm, or about 100 μm to 150 μm, or about 100 μm to 200 μm, or about 150 μm to 200 μm. In other embodiments, the first filter (1131) and/or second filter (1132) comprise filters having a pore size smaller than 10 μm. In further embodiments, the first filter (1131) and/or second filter (1132) comprise filters having a pore size larger than 200 μm.

The solid support (1133) (or solid support and filters, depending on the configuration) may be disposed within a valve. In some embodiments, the valve comprises a first valve position and a second valve position. In some embodiments, when the valve is in the first valve position the valve fluidly connects the sample tube (1210) to the first collection vial (1410). Additionally, when the valve is in the first valve position, the elution tube (1610) is not fluidly connected to the elution vial (1310). In some embodiment, when the valve is in the second valve position, the valve fluidly connects the elution tube (1610) to the elution vial (1310). And when the valve is in the second valve position, the sample tube (1210) is not fluidly connected to the sample vial (1410).

In alternative embodiments, e.g., in the modular device (1000) described herein, when the valve is in the first valve position, the valve fluidly connects the hub (1510) to the sample vial (1210), and neither the hub (1510) nor the sample vial (1210) is fluidly connected to the elution vial (1310). For example, when the valve is in the first valve position, the valve may fluidly connect the first collection tube (1410; attached to the hub (1510)) to the sample vial (1210), such that neither the collection tube (1410) nor the sample vial (1210) is fluidly connected to the elution vial (1310). In other embodiments, when the valve is in the second valve position, the valve fluidly connects the hub (1510) to the elution vial (1310), and neither the hub (1510) nor the elution vial (1310) is fluidly connected to the sample vial (1210). For example, when the valve is in the second valve position, the valve may fluidly connect the elution tube (1610; attached to the hub (1510)) to the elution vial (1310), such that neither the elution tube (1610) nor the elution vial (1310) is fluidly connected to the sample vial (1210).

In some embodiments, the sample vial (1210) further comprises a cover (1222). In some embodiments, the cover (1222) further comprises a pestle disposed therethrough. The cover (1222) may be configured to seal the sample vial (1210). In some embodiments, the sample vial (1210) further comprises a plug that attaches to the sample vial outlet (1221). In other embodiments, the sample vial (1210) further comprises a plug which reversibly attaches to the sample vial outlet (1221). The plug may be removable.

The sample vial (1210) described herein may further comprise a prefilter (1230), capable of filtering cellular debris. The prefilter (1230) may be configured such that the flow of fluid from the sample vial (1210) to outside the sample vial is through only the prefilter (1230). In some embodiments, the sample vial (1210) comprises a plurality of prefilters (1230). In some embodiments, the sample vial (1210) comprises one prefilter (1230). In other embodiments, the sample vial (1210) comprises two prefilters (1230). In further embodiments, the sample vial (1210) may comprise more than one prefilter (1230). A plurality of prefilters (1230) may be used in accordance with the present invention as long as the prefilters (1230) do not obstruct the flow of fluid from the sample vial (1210) to a first collection tube (1610). The prefilter (1230) may be disposed at the second sample vial end (1212). In some embodiments, the prefilter (1230) is disposed adjacent to the sample vial outlet (1221) and not within the sample vial (1210). In other embodiments, the prefilter (1230) is disposed adjacent to the sample vial outlet (1221), within the sample vial (1210). In some embodiments, the prefilter (1230) is positioned between the sample vial (1210) and the filter component (1130).

In some embodiments, the prefilter (1230) is comprised of any material that does not absorb and/or does not significantly absorb nucleic acids (e.g., DNA or RNA). In some embodiments, the prefilter (1230) comprises a polypropylene (PP) mesh filter. In some embodiments, the prefilter (1230) comprises a filter having a pore size selected from: 700 μm-200 μm filter. In other embodiments, the prefilter (1230) comprises a filter having a pore size selected from: 700 μm-350 μm. In further embodiments, the prefilter (1230) comprises a filter having a pore size selected from about 800 μm-50 μm, or about 800 μm-200 μm, or about 800 μm-350 μm, or about 800 μm-500 μm, or about 800 μm-650 μm, or about 650 μm-50 μm, or about 650 μm-200 μm, or about 650 μm-350 μm, or about 650 μm-500 μm, or about 500 μm-50 μm, or about 500 μm-200 μm, or about 500 μm-350 μm, or about 350 μm-50 μm, or about 350 μm-200 μm, or about 200 μm-50 μm.

In some embodiments, the means for providing positive and negative pressure in the first collection tube (1410) is a plunger (1440) slidably coupled to the second collection tube end (1412). In some embodiments, the plunger (1440) comprises a first plunger end (1441). The first plunger end (1441) may be disposed through the second sample tube end (1412) and within the sample tube (1410). In other embodiments, the means for providing positive and negative pressure in the first collection tube (1410) is a syringe or a similar device. In some embodiments, the first collection tube (1410) comprises a syringe. The syringe may be a needleless syringe. In some embodiments, the means for providing positive and negative pressure in the elution tube (1610) is a plunger (1640) slidably coupled to the second elution tube end (1612). In some embodiments, the plunger (1640) comprises a first plunger end (1641). The first plunger end (1641) may be disposed through the second elution tube end (1612) and within the elution tube (1610). In other embodiments, the means for providing positive and negative pressure in the elution tube (1610) is a syringe or a similar device. In some embodiments, the elution tube (1610) comprises a syringe (e.g., a needleless syringe).

The elution vial (1310) may further comprise a cap. In some embodiments, the cap is attached to the second elution vial end (1312). The cap may be configured to cover the elution vial opening (1320), to create a sealed elution vial (1310). In some embodiments, the cap further comprises a needle disposed therethrough. In some embodiments, the needle is fluidly connected to the first elution tube end (1611). In some embodiments, the needle is removable (i.e., the needle may be removed from the elution tube (1610). In further embodiments, the elution vial (1310) may be removed from the devices (1000) described herein. In some embodiments, the elution vial (1310) further comprises an elution buffer. In other embodiments, the elution tube (1610) further comprises an elution buffer.

The devices (1000) described herein are hand-held and/or enclosed. In some embodiments, the devices (1000) described herein are 3 inches wide and 5 inches tall. In some embodiments, the devices (1000) described herein are about 1 inch to 20 inches tall, or about 1 inch to 15 inches tall, or about 1 inch to 10 inches tall, or about 1 inch to 8 inches tall, or about 1 inch to 6 inches tall, or about 1 inch to 5 inches tall, or about 1 inch to 4 inches tall, or about 1 inch to 3 inches tall, or about 1 inch to 2 inches tall, or about 2 inches to 20 inches tall, or about 2 inches to 15 inches tall, or about 2 inches to 10 inches tall, or about 2 inches to 8 inches tall, or about 2 inches to 6 inches tall, or about 2 inches to 5 inches tall, or about 2 inches to 4 inches tall, or about 2 inches to 3 inches tall, or about 3 inches to 20 inches tall, or about 3 inches to 15 inches tall, or about 3 inches to 10 inches tall, or about 3 inches to 8 inches tall, or about 3 inches to 6 inches tall, or about 3 inches to 5 inches tall, or about 3 inches to 4 inches tall, or about 4 inches to 20 inches tall, or about 4 inches to 15 inches tall, or about 4 inches to 10 inches tall, or about 4 inches to 8 inches tall, or about 4 inches to 6 inches tall, or about 4 inches to 5 inches tall, or about 5 inches to 20 inches tall, or about 5 inches to 15 inches tall, or about 5 inches to 10 inches tall, or about 5 inches to 8 inches tall, or about 5 inches to 6 inches tall, or about 2 inches to 5 inches tall, or about 2 inches to 4 inches tall, or about 6 inches to 20 inches tall, or about 6 inches to 15 inches tall, or about 6 inches to 10 inches tall, or about 6 inches to 8 inches tall, or about 8 inches to 20 inches tall, or about 8 inches to 15 inches tall, or about 8 inches to 10 inches tall, or about 10 inches to 20 inches tall, or about 10 inches to 15 inches tall, or about 15 inches to 20 inches tall.

In some embodiments, the devices (1000) described herein are about 1 inch to 20 inches wide, or about 1 inch to 15 inches wide, or about 1 inch to 10 inches wide, or about 1 inch to 8 inches wide, or about 1 inch to 6 inches wide, or about 1 inch to 5 inches wide, or about 1 inch to 4 inches wide, or about 1 inch to 3 inches wide, or about 1 inch to 2 inches wide, or about 2 inches to 20 inches wide, or about 2 inches to 15 inches wide, or about 2 inches to 10 inches wide, or about 2 inches to 8 inches wide, or about 2 inches to 6 inches wide, or about 2 inches to 5 inches wide, or about 2 inches to 4 inches wide, or about 2 inches to 3 inches wide, or about 3 inches to 20 inches wide, or about 3 inches to 15 inches wide, or about 3 inches to 10 inches wide, or about 3 inches to 8 inches wide, or about 3 inches to 6 inches wide, or about 3 inches to 5 inches wide, or about 3 inches to 4 inches wide, or about 4 inches to 20 inches wide, or about 4 inches to 15 inches wide, or about 4 inches to 10 inches wide, or about 4 inches to 8 inches wide, or about 4 inches to 6 inches wide, or about 4 inches to 5 inches wide, or about 5 inches to 20 inches wide, or about 5 inches to 15 inches wide, or about 5 inches to 10 inches wide, or about 5 inches to 8 inches wide, or about 5 inches to 6 inches wide, or about 2 inches to 5 inches wide, or about 2 inches to 4 inches wide, or about 6 inches to 20 inches wide, or about 6 inches to 15 inches wide, or about 6 inches to 10 inches wide, or about 6 inches to 8 inches wide, or about 8 inches to 20 inches wide, or about 8 inches to 15 inches wide, or about 8 inches to 10 inches wide, or about 10 inches to 20 inches wide, or about 10 inches to 15 inches wide, or about 15 inches to 20 inches wide.

The size of the devices (1000) described herein may vary depending on the type of biological sample being processed. For example, a dilute urine sample may require a larger device to process the larger sample volume.

Referring to FIGS. 15 and 17, the present invention also features a method of isolating and extracting nucleic acids from a biological sample using devices (1000) as described herein. In some embodiments, the method comprises adding a sample to the biological sample vial (1210). In some embodiments, the sample vial (1210) comprises a lysis buffer as described herein.

In some embodiments, the biological sample comprises tissue sample. In some embodiments, the biological sample comprises tissue from shrimp including but not limited to shrimp muscle tissue, shrimp organs (e.g., intestines or liver), shrimp pleopods, or a combination thereof. In other embodiments, the biological sample may comprise aquatic animal tissue, non-aquatic animal tissue, saltwater animal tissue, freshwater animal tissue, animal waste (e.g., feces), plant tissue, bacteria, or yeast. In some embodiments, the biological sample comprises ecological water samples or soil. In further embodiments, the biological sample may include but is not limited to saliva, blood (e.g., whole blood and serum), urine, stool, respiratory samples (e.g., swabs or sputum), cerebrospinal fluid, or amniotic fluid. In some embodiments, the biological sample is obtained from an animal (e.g., a mammal).

In some embodiments, the method comprises enclosing the sample vial (1210) with a cover (1222). In certain embodiments, the biological sample is a lysed biological sample. In other embodiments, the method comprises enclosing the sample vial (1210) with a cover (1222) comprising a pestle disposed therethrough.

If needed, the method may comprise mechanically disrupting (e.g., grinding) the biological sample. In some embodiments, the method comprises grinding the biological sample. Grinding the biological sample may comprise axially rotating the pestle. In some embodiments, the pestle may be rotated bidirectionally.

In certain embodiments, e.g., when using the modular device (1000) as described herein, the method may comprise attaching the inlet (1421) at the first collection tube end (1411) to the opening (1520) of the hub (1510) such that the inlet (1421) at the first collection tube end (1411) fluidly connects to the opening (1520) of the hub (1510). The inlet (1421) may be configured to attach to/engage with the opening (1520) of the hub (1510), e.g., for flow of the biological sample in the sample vial (1210) to the first collection tube (1410). The sample vial (1210) and the first collection tube (1410) may be connected (e.g, temporarily attached) to allow fluid flow between the two, wherein the connection between the two is configured (e.g, sealed) to prevent leaking.

In some embodiments, the method comprises positioning the filter component (1130) such that the sample vial (1221) is connected to the first collection tube. For example, if the filter component (1130) is disposed within a valve, the valve may be turned into a first valve position such that the sample vial (1210) and the first collection tube (1410) are fluidly connected. In some embodiments, the method comprises removing the plug from the sample vial outlet (1221) disposed at a first sample vial end (1211). Next, the method may comprises creating negative pressure within the first collection tube (1410) to pull the biological sample from the sample vial (1210) through the filter component (1130), into the first collection tube (1410). The method may further comprise pulling the biological sample through a prefilter (1230). Once the biological sample has passed through the filter component (1130); the filter component (1130) comprises isolated nucleic acid (e.g., DNA e.g., genomic DNA, or RNA) reversibly bound to the solid support (1133).

In certain embodiments, e.g., when using the modular device (1000) as described herein, the method may comprise detaching the inlet (1421) at the first collection tube end (1411) from the opening (1520) of the hub (1510) (i.e., removing the first collection tube (1410) from the hub (1510) of the device). In some embodiments, the method comprises may comprise attaching the inlet (1621) at the first elution tube end (1611) to the opening (1520) of the hub (1510) such that the inlet (1621) at the first collection tube end (1611) fluidly connects to the opening (1520) of the hub (1510). The inlet (1621) may be configured to attach to/engage with the opening (1520) of the hub (1510), e.g., for the flow of the elution buffer in the elution vial (1310) to the elution tube (1610). The elution vial (1310) and the elution tube (1610) may be connected (e.g, temporarily attached) to allow fluid (e.g., elution buffer) to flow between the two wherein the connection between the two is configured (e.g, sealed) to prevent leaking.

In some embodiments, the method comprises positioning the filter component (1130) such that the elution vial (1310) is connected to the elution tube (1610). For example, if the filter component (1130) is disposed within a valve, the valve may be turned into a second valve position such that the elution tube (1610) to the elution vial (1310) are fluidly connected.

Depending on the configuration of the devices (1000) described herein; In some embodiments, the elution vial (1310) comprises an elution buffer and in other embodiments, the elution tube (1610) comprises the elution buffer. Therefore, in some embodiments, the method comprises creating a negative pressure within the elution tube (1610) to pull the elution buffer from the elution vial (1310) through the filter component (1130), into the elution tube (1610). Next, the method comprises creating a positive pressure within the elution tube (1610) to push the elution buffer from the elution tube (1610) through the filter component (1130), into the elution vial (1310). In other embodiments, the method comprises creating positive pressure within the elution tube (1610) to push the elution buffer from the elution tube (1610) through the filter component (1130), into the elution vial (1310).

In some embodiments, the method comprises pulling and pushing the elution buffer through the filter component (1130) (i.e., between the elution vial (1310) and the elution tube (1610)) one or more times. In other, the method comprises pulling and pushing the elution buffer through the filter component (1130) (i.e., between the elution vial (1310) and the elution tube (1610)) 1-20 times. In other, the method comprises pulling and pushing the elution buffer through the filter component (1130) (i.e., between the elution vial (1310) and the elution tube (1610)) 2-10 times. In other embodiments, the method comprises pulling and pushing the elution buffer through the filter component (1130) (i.e., between the elution vial (1310) and the elution tube (1610)) 3-5 times.

In some embodiments, the isolated nucleic acid (e.g., DNA e.g., genomic DNA, or RNA) is eluted from the filter component (1130). The isolated nucleic acid (e.g., DNA e.g., genomic DNA, or RNA) may be eluted from the solid support (1133) of the filter component (1130). In some embodiments, the elution buffer comprises genomic DNA extracted from the sample.

In some embodiments, the method may further comprise removing the elution vial (1310) from the device (1000). In other embodiments, the method may further comprise removing the elution tube (1610) from the device (1000). In some embodiments, the elution vial (1310) comprises an elution buffer comprising isolated nucleic acid (e.g., DNA e.g., genomic DNA, or RNA. In other embodiments, the elution tube (1610) comprises an elution buffer comprising isolated nucleic acid (e.g., DNA e.g., genomic DNA, or RNA).

The present invention provides sample processing methods for isolating and extracting genomic nucleic acids (e.g., gDNA) from a biological sample. In some embodiments, the method can collect genomic nucleic acids (e.g., gDNA) from the sample at a concentration of 270 ng/μl. In other embodiments, the method can collect genomic nucleic acids (e.g., gDNA) from a sample at a concentration of about 50-2000 ng/μl, or about 200-2000 ng/μl, or about 350-2000 ng/μl, or about 500-2000 ng/μl, or about 650-2000 ng/μl, or about 800-2000 ng/μl, or about 950-2000 ng/μl, or about 1100-2000 ng/μl, or about 1300-2000 ng/μl, or about 1500-2000 ng/μl, or about 50-1500 ng/μl, or about 200-1500 ng/μl, or about 350-1500 ng/μl, or about 500-1500 ng/μl, or about 650-1500 ng/μl, or about 800-1500 ng/μl, or about 950-1500 ng/μl, or about 1100-1500 ng/μl, or about 1300-1500 ng/μl, or about 50-1300 ng/μl, or about 200-1300 ng/μl, or about 350-1300 ng/μl, or about 500-1300 ng/μl, or about 650-1300 ng/μl, or about 800-1300 ng/μl, or about 950-1300 ng/μl, or about 1100-1300 ng/μl, or about 50-1100 ng/μl, or about 200-1100 ng/μl, or about 350-1100 ng/μl, or about 500-1100 ng/μl, or about 650-1100 ng/μl, or about 800-1100 ng/μl, or about 950-1100 ng/μl, or about 50-950 ng/μl, or about 200-950 ng/μl, or about 350-950 ng/μl, or about 500-950 ng/μl, or about 650-950 ng/μl, or about 800-950 ng/μl, or about 50-800 ng/μl, or about 200-800 ng/μl, or about 350-800 ng/μl, or about 500-800 ng/μl, or about 650-800 ng/μl, or about 50-650 ng/μl, or about 200-650 ng/μl, or about 350-650 ng/μl, or about 500-650 ng/μl, or about 50-500 ng/μl, or about 200-500 ng/μl, or about 350-500 ng/μl, or about 50-350 ng/μl, or about 200-350 ng/μl, or about 50-200 ng/μl. In furher embodiments, the method can collect genomic nucleic acids (e.g., gDNA) from a sample at a concentration of greater than 2000 ng/μl.

In some embodiments, the method can collect 500-2500 ng of genomic nucleic acids (e.g., gDNA) per mg of biological sample (e.g., tissue). In other embodiments, the method can collect about 500-2500 ng, or about 500-2000 ng, or about 500-1500 ng, or about 500-1000 ng, or about 1000-2500 ng, or about 1000-2000 ng, or about 1000-1500, or about 1500-2500 ng, or about 1500-2000 ng, or about 2000-2500 ng of genomic nucleic acids (e.g., gDNA) per mg of biological sample (e.g., tissue).

In some embodiments, the genomic nucleic acids comprise genomic DNA or genomic RNA. The genomic RNA may comprise mRNA or RNA from an RNA-virus.

Lysis Buffer for Nucleic Acid Extractions:

The present invention also features a lysis buffer composition to be used with the systems and devices described herein.

The present invention may feature a composition comprising a phosphate buffer, a metal chelator (e.g., EDTA) and a detergent (e.g., SDS). In some embodiments, the present invention features a composition comprising a phosphate buffer, a metal chelator (e.g., EDTA) and a detergent (e.g., SDS), essentially free of enzymes.

In some embodiments, the phosphate buffer comprises phosphate buffer saline (PBS). In some embodiments, the phosphate buffer (e.g., PBS) comprises $KH_2PO_4$, $K_2HPO_4$, $Na_2HPO_4$, $NaH_2HPO_4$, NaCl, KCl or a combination thereof. In some embodiments, the phosphate buffer (e.g., PBS) comprises or consists of $KH_2PO_4$, $Na_2HPO_4$, NaCl, and KCl. In other embodiments, the phosphate buffer (e.g., PBS) comprises or consists of $K_2HPO_4$, $Na_2HPO_4$, NaCl, and KCl. In some embodiments, the phosphate buffer (e.g., PBS) comprises or consists of $KH_2PO_4$, $NaH_2HPO_4$, NaCl, and KCl. In other embodiments, the phosphate buffer (e.g., PBS) comprises or consists of $K_2HPO_4$, $NaH_2HPO_4$, NaCl, and KCl.

In some embodiments, the phosphate buffer (e.g., PBS) comprises a final concentration of 10 mM to 80 mM. In other embodiment, the phosphate buffer (e.g., PBS) comprises a final concentration of about 0 mM to 100 mM, or about 0 mM to 90 mM, or about 0 mM to 80 mM, or about 0 mM to 70 mM, or about 0 mM to 60 mM, or about 0 mM to 50 mM, or about 0 mM to 40 mM, or about 0 mM to 30 mM, or about 0 mM to 20 mM, or about 0 mM to 10 mM, or about 0 mM to 1 mM, 1 mM to 100 mM, or about 1 mM to 90 mM, or about 1 mM to 80 mM, or about 1 mM to 70 mM, or about 1 mM to 60 mM, or about 1 mM to 50 mM, or about 1 mM to 40 mM, or about 1 mM to 30 mM, or about 1 mM to 20 mM, or about 1 mM to 10 mM, 10 mM to 100 mM, or about 10 mM to 90 mM, or about 10 mM to 80 mM, or about 10 mM to 70 mM, or about 10 mM to 60 mM, or about 10 mM to 50 mM, or about 10 mM to 40 mM, or about 10 mM to 30 mM, or about 10 mM to 20 mM, 20 mM to 100 mM, or about 20 mM to 90 mM, or about 20 mM to 80 mM, or about 20 mM to 70 mM, or about 20 mM to 60 mM, or about 20 mM to 50 mM, or about 20 mM to 40 mM, or about 20 mM to 30 mM, 30 mM to 100 mM, or about 30 mM to 90 mM, or about 30 mM to 80 mM, or about 30 mM to 70 mM, or about 30 mM to 60 mM, or about 30 mM to 50 mM, or about 30 mM to 40 mM, 40 mM to 100 mM, or about 40 mM to 90 mM, or about 40 mM to 80 mM, or about 40 mM to 70 mM, or about 40 mM to 60 mM, or about 40 mM to 50 mM, 50 mM to 100 mM, or about 50 mM to 90 mM, or about 50 mM to 80 mM, or about 50 mM to 70 mM, or about 50 mM to 60 mM, 60 mM to 100 mM, or about 60 mM to 90 mM, or about 60 mM to 80 mM, or about 60 mM to 70 mM, 70 mM to 100 mM, or about 70 mM to 90 mM, or about 70 mM to 80 mM, 80 mM to 100 mM, or about 80 mM to 90 mM, or about 90 mM to 100 mM. In further embodiments, the phosphate buffer (e.g., PBS) comprises a final concentration of about 0 mM, or about 1 mM, or about 10 mM, or about 20 mM, or about 30 mM, or about 40 mM, or about 50 mM, or about 60 mM, or about 70 mM, or about 80 mM, or about 90 mM, or about 100 mM.

In some embodiments, the metal chelator is ethylenediaminetetraacetic acid (EDTA). In other embodiments, the metal chelator is ethylene glycol tetraacetic acid (EGTA). Other metal chelators may be used in accordance with the compositions described herein. In some embodiments, the metal chelator (e.g., EDTA or EGTA) comprises a final concentration of 2.5 mM to 20 mM. In other embodiments, the metal chelator (e.g., EDTA or EGTA) comprises a final concentration of about 0 mM to 30 mM, or about 0 mM to 25 mM, or about 0 mM to 20 mM, or about 0 mM to 15 mM, or about 0 mM to 10 mM, or about 0 mM to 5 mM, or about 0 mM to 2.5 mM, or about 0 mM to 1 mM, or about 1 mM to 30 mM, or about 1 mM to 25 mM, or about 1 mM to 20 mM, or about 1 mM to 15 mM, or about 1 mM to 10 mM, or about 1 mM to 5 mM, or about 1 mM to 2.5 mM, or about 2.5 mM to 30 mM, or about 2.5 mM to 25 mM, or about 2.5 mM to 20 mM, or about 2.5 mM to 15 mM, or about 2.5 mM to 10 mM, or about 2.5 mM to 5 mM, or about 5 mM to 30 mM, or about 5 mM to 25 mM, or about 5 mM to 20 mM, or about 5 mM to 15 mM, or about 5 mM to 10 mM, or about 10 mM to 30 mM, or about 10 mM to 25 mM, or about 10 mM to 20 mM, or about 10 mM to 15 mM, or about 15 mM to 30 mM, or about 15 mM to 25 mM, or about 15 mM to 20 mM, or about 20 mM to 30 mM, or about 20 mM to 25 mM, or about 25 mM to 30 mM. In further embodiments, the metal chelator (e.g., EDTA or EGTA) comprises a final concentration of about 0 mM, about 1 mM, or about 2.5 mM, or about 5 mM, or about 10 mM, or about 15 mM, or about 20 mM, or about 25 mM, or about 30 mM.

In some embodiments, the detergent is sodium dodecyl sulfate (SDS). In other embodiments, the detergent is triton X-100. Other detergents may be used in accordance with the compositions described herein. In some embodiments, the detergent (e.g., SDS) comprises a final concentration of 0.001% to 5%. In other embodiments, the detergent (e.g., SDS comprises a final concentration of about 0% to 5%, or about 0% to 4%, or about 0% to 3%, or about 0% to 2%, or about 0% to 1%, or about 0% to 0.05%, or about 0% to 0.005% or about 0% to 0.001%, or about 0.001% to 5%, or about 0.001% to 4%, or about 0.001% to 3%, or about 0.001% to 2%, or about 0.001% to 1%, or about 0.001% to 0.05%, or about 0.001% to 0.005%, or about 0.005% to 5%, or about 0.005% to 4%, or about 0.005% to 3%, or about 0.005% to 2%, or about 0.005% to 1%, or about 0.005% to 0.05%, or about 0.05% to 5%, or about 0.05% to 4%, or about 0.05% to 3%, or about 0.05% to 2%, or about 0.05% to 1%, or about 1% to 5%, or about 1% to 4%, or about 1% to 3%, or about 1% to 2%, or about 2% to 5%, or about 2% to 4%, or about 2% to 3%, or about 3% to 5%, or about 3% to 4%, or about 4% to 5%. In further embodiments, the detergent (e.g., SDS) comprises a final concentration of about 0%, or about 0.001%, or about 0.005%, or about 0.01%, or about 0.05%, or about 0.1%, or about 0.5%, or about 1%, or about 2%, or about 3%, or about 4%, or about 5%.

In some embodiments, the composition described herein comprises a pH of 1 to 14. In other embodiments, the composition described herein comprises a pH of about 1.0 to 14, or about 1.0 to 13, or about 1.0 to 12, or about 1.0 to 11, or about 1.0 to 10, or about 1.0 to 9.0, or about 1.0 to 8.0 to about 1.0 to 7.0, or about 1.0 to 6.0, or about 1.0 to 5.0, or about 1.0 to 4.0, or about 1.0 to 3.0, or about 1.0 to 2.0, or about 1.0 to 1.5, or about 1.5 to 14, or about 1.5 to 13, or about 1.5 to 12, or about 1.5 to 11, or about 1.5 to 10, or about 1.5 to 9.0, or about 1.5 to 8.0 to about 1.5 to 7.0, or about 1.5 to 6.0, or about 1.5 to 5.0, or about 1.5 to 4.0, or about 1.5 to 3.0, or about 1.5 to 2.0, or about 2.0 to 14, or about 2.0 to 13, or about 2.0 to 12, or about 2.0 to 11, or about 2.0 to 10, or about 2.0 to 9.0, or about 2.0 to 8.0 to about 2.0 to 7.0, or about 2.0 to 6.0, or about 2.0 to 5.0, or about 2.0 to 4.0, or about 2.0 to 3.0, or about 3.0 to 14, or about 3.0 to 13, or about 3.0 to 12, or about 3.0 to 11, or about 3.0 to 10, or about 3.0 to 9.0, or about 3.0 to 8.0 to about 3.0 to 7.0, or about 3.0 to 6.0, or about 3.0 to 5.0, or about 3.0 to 4.0, or about 4.0 to 14, or about 4.0 to 13, or about 4.0 to 12, or about 4.0 to 11, or about 4.0 to 10, or about 4.0 to 9.0, or about 4.0 to 8.0 to about 4.0 to 7.0, or about 4.0 to 6.0, or about 4.0 to 5.0, or about 5.0 to 14, or about 5.0 to 13, or about 5.0 to 12, or about 5.0 to 11, or about 5.0 to 10, or about 5.0 to 9.0, or about 5.0 to 8.0 to about 5.0 to 7.0, or about 5.0 to 6.0, or about 6.0 to 14, or about 6.0 to 13, or about 6.0 to 12, or about 6.0 to 11, or about 6.0 to 10, or about 6.0 to 9.0, or about 6.0 to 8.0 to about 6.0 to 7.0, or about 7.0 to 14, or about 7.0 to 13, or about 7.0 to 12, or about 7.0 to 11, or about 7.0 to 10, or about 7.0 to 9.0, or about 7.0 to 8.0, or about 8.0 to 14, or about 8.0 to 13, or about 8.0 to 12, or about 8.0 to 11, or about 8.0 to 10, or about 8.0 to 9.0, or about 9.0 to 14, or about 9.0 to 13, or about 9.0 to 12, or about 9.0 to 11, or about 9.0 to 10, or about 10 to 14, or about 10 to 13, or about 10 to 12, or about 10 to 11, or about 11 to 14, or about 11 to 13, or about 11 to 12, or about 12 to 14, or about 12 to 13, or about 13 to 14. In further embodiment, the composition described herein comprises a pH of about 1.0, or about 1.5, or about 2.0, or about 3.0, or about 4.0, or about 5.0, or about 6.0, or about 7.0, or about 8.0, or about 9.0, or about 10, or about 11, or about 12, or about 13, or about 14.

In some embodiments, the pH of the compositions described herein is adjusted to an aforementioned pH. In other embodiments, the pH of the compositions described herein are not adjusted. The pH of a composition with no pH adjustment may be about a pH of 9.0.

In some embodiments, the compositions described herein are essentially free of enzymes. In other embodiments, the compositions described herein are free of an effective amount of enzymes. Non-limiting examples of enzymes include but are not limited to proteinase, lysozyme, RNAse, DNAse or a combination thereof. Additionally, the compositions described herein may be essentially free of or free of an effective amount of any chaotropic agents (e.g., urea or guanidinium chloride).

One of the unique and inventive technical features of the present invention is the use of a composition (e.g., lysis buffer) essentially free of enzymes in combination with the systems and devices described herein. Without wishing to limit the invention to any theory or mechanism, it is believed that the technical feature of the present invention advantageously provides for a rapid and cost-effective nucleic acid extraction method that gives high quality nucleic acid in high concentration in a short amount of time. Moreover, the use of the lysis buffer essentially free of enzymes avoids storage restrictions (e.g., cold storage) and avoids incubation times, which ultimately decreases the amount of time needed to isolate and extract nucleic acids. Thus, the systems and devices described herein can be readily used in point-of-care (POC) locations.

Example 1: Lysis Buffer

The following is a non-limiting example of lysis buffers that may be used in accordance with the present invention. It is to be understood that said example is not intended to limit the present invention in any way. Equivalents or substitutes are within the scope of the present invention

TABLE 1

Lysis Buffer 1 Composition.

| Stock: | Volume | Concentration |
|---|---|---|
| 10X PBS | 10 mL | 20 mM |
| 1% SDS | 250 μM | 0.00005% |
| 0.5M EDTA | 250 μM | 0.0025M |
| Water | 39.90 mL | |
| Total (mL) | 50 | |

TABLE 2

Lysis Buffer 2 Composition.

| Stock: | Volume | Concentration |
|---|---|---|
| 10X PBS | 10 mL | 20 mM |
| 1% SDS | 2.5 mL | 0.05% |
| 0.5M EDTA | 250 μM | 0.0025M |
| Water | 37.25 mL | |
| Total (mL) | 50 | |

TABLE 3

Lysis Buffer 3 Composition.

| Stock: | Volume | Concentration |
|---|---|---|
| 10X PBS | 10 mL | 20 mM |
| 1% SDS | 250 μM | 0.00005% |
| 0.5M EDTA | 2.5 mL | 0.025M |
| Water | 37.25 | |
| Total (mL) | 50 | |

TABLE 4

Lysis Buffer 4 Composition.

| Stock: | Volume | Concentration |
|---|---|---|
| 10X PBS | 10 mL | 20 mM |
| 1% SDS | 2.5 mL | 0.05% |
| 0.5M EDTA | 2.5 mL | 0.025M |
| Water | 35 mL | |
| Total (mL) | 50 | |

Example 2: Kit

The following is a non-limiting of an alternative embodiment of the present invention, which may be packaged as a kit. It is to be understood that said example is not intended to limit the present invention in any way. Equivalents or substitutes are within the scope of the present invention.

FIG. 18 shows a group of components that may be used in the present invention. For example, the system or methods may feature one or more tubes, e.g., a sample vial (500), for holding the sample, a buffer, etc. in its tube housing (510), and a first cap (520). In some embodiments, the first cap (520) is directly connected to the tube (500), e.g., as shown. In some embodiments, the first cap (520) is separate. The first cap (520) can be attached to the first end (511) of the sample tube (500) and snugly engage the first end (511) of the sample tube (500) via a seal (525). The first cap (520) comprises a port (522) that allows the passage of fluid from the inner cavity of the tube out via the cap (520). The size of the port (522) is appropriate for engaging and snugly fitting into a port of a cartridge, as described below. The first cap (520) further comprises a filter (530) for filtering cellular debris.

The system further comprises a sample tube (500) and a second cap (550). In some embodiments, the second cap (550) is directly connected to the tube (500), e.g., as shown. In some embodiments, the second cap (550) is separate. The second cap (550) can be attached to the first end (511) of the sample tube (500) and snugly engage the top end of the tube via a seal (555). The second cap (550) comprises a port (552) that allows passage of fluid from the inner cavity of the tube out via the cap (550). The size of the port (552) is appropriate for engaging and snugly fitting into a port of a filter cartridge (600), as described below.

The system further comprises a filter cartridge (600). The filter cartridge (600) features a housing (610) with a first end (611) and a second end (612), and a filter component (e.g., cellulose) (630) sandwiched (e.g., directly or indirectly) between the ends. The cartridge further comprises a first port (620) at the first end and a second port (622) at the second end that allows the passage of fluid through the cartridge housing (610) via the filter component (630). The sizes of the ports are appropriate for engaging and snugly fitting the ports (522, 552) of the tubes (500).

The system further comprises one or more syringes (700). The syringe may feature a syringe housing (710) and a plunger (730) that provides positive and negative pressure, e.g., to the contents of the syringe housing (710) thereby pushing or pulling liquid in and out of the syringe via the open port (720) at its first end. The size of the port (720) is appropriate for engaging and snugly fitting the ports (620, 622) of the cartridge.

Referring to FIG. 19, the aforementioned components may be combined to create a kit. For example, the kit may comprise a cartridge, two syringes, two tubes, one first cap, and one second cap. In some embodiments, the kit further comprises one or more buffers, e.g., a lysis buffer (501), an elution buffer (502), etc.

Referring to FIG. 20, the methods of nucleic acid extraction and isolation may feature one or more steps as described below: (1) Add lysis buffer (501) and sample to a tube; optionally mix and/or grind; (2) Cap the tube with the first cap; (3) Insert the port of the first cap of the tube into a port of the cartridge, and insert the port of a first syringe into the opposite port of the filter cartridge; (5) Draw lysis buffer through filter cartridge to syringe (nucleic acids (e.g., DNA; 101) should temporarily bind to filter); (6) Detach tube and syringe and discard; (7) Add elution buffer (502) to a second tube and cap with a second cap; (8) Insert the port of the second cap of the tube into a port of the filter cartridge and insert the port of a second syringe into the opposite port of the filter cartridge; (9) Draw elution buffer through filter cartridge to syringe (optionally repeat several times so elution buffer passes through the filter multiple times); (10) Detach syringe from cartridge/second tube and discard cartridge/second tube; and (11) Retain elution buffer containing nucleic acids (e.g., DNA; 101) in syringe.

EMBODIMENTS

The following embodiments are intended to be illustrative only and not to be limiting in any way.

Embodiment Set A

Embodiment 1A: A system for isolating and extracting nucleic acids from a biological sample, the system comprising: a filtration column (110) having a first column end (111), a second column end (112), and an inner cavity, the filtration column (110) comprising: (a) a means for providing positive and negative pressure disposed at the first column end (111); an opening (120) disposed in the second column end (112); (c) a filter component (130) immobilized in the inner cavity of the filtration column (110), the filter component (130) divides the inner cavity into at least two subcavities wherein a first subcavity is between the filter component (130) and the first column end (111) and a second subcavity is between the filter component (130) and the second column end (112), and fluid passing from the first subcavity to the second subcavity necessarily passes through the filter component (130), wherein the filter component (130) comprises a solid support (133) adapted to reversibly bind nucleic acid.

Embodiment 2A: The system of embodiment 1A, wherein the filter component (130) further comprises a first filter (131) adjacent to or in contact with the solid support (133).

Embodiment 3A: The system of embodiment 1A, wherein the filter component (130) further comprises a first filter (131) and a second filter (132) wherein the solid support (133) is sandwiched between the first filter (131) and second filter (132).

Embodiment 4A: The system of any one of embodiments 1A-3A, further comprising a removable plug for sealing the opening (120) in the second column end (112).

Embodiment 5A: A system for isolating and extracting nucleic acids from a biological sample, the system comprising a filtration column (110) according to any one of embodiment 1A-4A, and a sample vial (210) having a first sample vial end (211), a second sample vial end (212), and an inner cavity, wherein a sample vial outlet (220) is disposed in the second sample vial end (212).

Embodiment 6A: The system of embodiment 5A, wherein the sample vial (210) further comprises a prefilter (230) immobilized in the inner cavity of the of the sample vial (210).

Embodiment 7A: The system of embodiment 6A, wherein the prefilter (230) divides the inner cavity into at least two subcavities wherein a first subcavity is between the prefilter (230) and the first sample vial end (211) and a second subcavity is between the prefilter (230) and the second sample vial end (212), and fluid passing from the first subcavity to the second subcavity necessarily passes through the prefilter (230).

Embodiment 8A: The system of embodiment 6A or embodiment 7A, wherein the prefilter (230) is for filter cellular debris.

Embodiment 9A: The system of any one of embodiments 5A-8A, wherein the opening (120) in the second column end (112) of the filtration column (110) engages the sample vial outlet (220) of the sample vial (210) in a manner that fluidly connects the filtration column (110) with the sample vial (210).

Embodiment 10A: A system for isolating and extracting nucleic acids from a biological sample comprising a filtration column (110) according to any one of embodiments 1A-4A, a sample vial (210) according to any one of embodiments 5A-9A, and an elution vial having a first elution vial end (311), a second elution vial end (312), and an inner cavity, wherein an elution vial outlet (320) is disposed in the second elution vial end (312).

Embodiment 11A: The system of embodiment 10A, wherein the opening (120) in the second column end (112) of the filtration column (110) engages the elution vial outlet (320) of the elution vial (310) in a manner that fluidly connects the filtration column (110) with the elution vial (310).

Embodiment 12A: A system for isolating and extracting nucleic acids from a biological sample, the system comprising: a filtration column (110) comprising: (a) a first column end (111) and a second column end (112), wherein the first column end (111) comprises a means for providing positive and negative pressure disposed therein, and the second column end (112) comprises an opening (120); (b) a filter component (130) disposed within the filtration column (110), wherein the filter component comprises a first filter (131), a second filter (132), and a solid support (133) capable of reversibly binding nucleic acid sandwiched between the first filter (131) and the second filter (132);

Embodiment 13A: The system of embodiment 12A, further comprising a plug; wherein the plug attaches to the opening (120) of the filtration column (110) to create an enclosed system.

Embodiment 14A: The system of embodiment 12A, wherein the means for providing positive and negative pressure is a syringe comprising a needle; wherein the needle is inserted through the first column end (111) of the filtration column (110).

Embodiment 15A: The system of embodiment 12A, wherein the means for providing positive and negative pressure is a plunger (140) slidably coupled to the filtration column (110).

Embodiment 16A: The system of embodiment 15A, wherein the plunger (140) comprises a first plunger end (141); wherein the first plunger end (141) is disposed through the first column end (111) and within the filtration column (110).

Embodiment 17A: The system of any one of embodiments 12A-16A, wherein the first filter (131) comprises a polyethylene (PET) filter.

Embodiment 18A: The system of any one of embodiments 12A-17A, wherein the second filter (132) comprises a polyethylene (PET) filter.

Embodiment 19A: The system of embodiment 17A or embodiment 18A, wherein the PET filter is 35p PET filter.

Embodiment 20A: The system of any one of embodiments 12A-19A, wherein the solid support (133) comprises cellulose.

Embodiment 21A: The system of any one of embodiments 12A-19A, wherein the solid support (133) comprises nitrocellulose.

Embodiment 22A: The system of any one of embodiments 12A-19A, wherein the solid support (133) comprises a cotton pad.

Embodiment 23A: The system of any one of embodiments 12A-19A, wherein the solid support (133) comprises paper.

Embodiment 24A: The system of any one of embodiments 12A-23A, further comprising a sample vial (210) comprising an outlet (220) at a second sample vial end (212).

Embodiment 25A: The system of embodiment 24A, wherein the opening (120) of the filtration column (110) attaches to the outlet (220) of the sample vial (210) to create an enclosed system.

Embodiment 26A: The system of embodiment 24A or embodiment 25A, wherein the sample vial (210) further comprises a prefilter (230) disposed at the second sample end (212).

Embodiment 27A: The system of embodiment 26A, wherein the prefilter (230) comprises a polypropylene (PP) mesh filter.

Embodiment 28A: The system of embodiment 27A, wherein the PP mesh filter comprises a 700 μm-200 μm PP mesh filter.

Embodiment 29A: The system of embodiment 27A or embodiment 28A, wherein the PP mesh filter comprises a 700 μm-350 μm PP mesh filter.

Embodiment 30A: The system of any one of embodiments 26A-29A, wherein the prefilter (230) is removable.

Embodiment 31A: The system of any one of embodiments 26A-30A, wherein the sample vial (210) further comprises a lysed biological sample.

Embodiment 32A: The system of any one of embodiments 12A-23A, further comprising an elution vial (310) comprising an outlet (320) at a second elution vial end (312).

Embodiment 33A: The system of embodiment 32A, wherein the opening (120) of the filtration column (110) attaches to the outlet (320) of the elution vial (310) to create an enclosed system.

Embodiment 34A: The system of embodiment 32A, wherein a blunt needle attaches to the opening (120) of the filtration column (110); wherein the needle is inserted into the second elution vial end (312) to create an enclosed system.

Embodiment 35A: The system of any one of embodiments 32A-34A, wherein the elution vial (310) further comprises an elution buffer.

Embodiment 36A: A method of isolating and extracting nucleic acids from a biological sample; the method comprising, (a) attaching a sample vial according to any one of embodiments 24A-31A to a filter column according to any one of embodiments 12A-23A, to create an enclosed system, (b) creating negative pressure within the filtration column (110) to pull the lysed biological sample from the sample vial (120) through the filter component (130), into the first column end (111) of the filtration column (110); (c) creating a positive pressure within the filtration column (110) to push the lysed biological sample through the filter column (130) and back into the sample vial; (d) removing the sample vial (210) and attaching an elution vial (310) according to any one of embodiments 32A-35A to the filter column, to create an enclosed system; (e) creating negative pressure within the filtration column (110) to pull the elution buffer through the filter component (130) and into the first column end (111) of the filtration column (110); (f) creating positive pressure within the filtration column (110) to push the elution buffer through the filter component (130) and back into the elution vial (310).

Embodiment 37A: The method of embodiment 36A, wherein steps (e) and (f) are repeated 2-10 times.

Embodiment 38A: The method of embodiment 36A or 37A, wherein steps (e) and (f) are repeated 3-5 times.

Embodiment 39A: A system for isolating nucleic acids from a biological sample; the system comprising: (a) filtration column (110) comprising: (i) a first column end (111) and a second column end (112), wherein the first column end (111) comprises a means for providing positive and negative pressure disposed therein, and the second column end (112) comprises an opening (120); and (ii) a filter component (130) disposed within the filtration column (110), wherein the filter component comprises a first filter (131), a second filter (132), and a solid support (133) capable of reversibly binding nucleic acid sandwiched between the first filter (131) and the second filter (132); and (b) a sample vial (210) comprising an outlet (220) at a vial second end (222); wherein the opening (120) of the filtration column (110) attaches to the outlet (220) of the sample vial (210) to create an enclosed system.

Embodiment 40A: The system of embodiment 39A, wherein the means for providing positive and negative pressure is a syringe comprising a needle; wherein the needle is inserted through the first column end (111) of the filtration column.

Embodiment 41A: The system of embodiment 39A, wherein the means for providing positive and negative pressure is a plunger (140) slidably coupled to the filtration column (110).

Embodiment 42A: The system of embodiment 41A, wherein the plunger (140) comprises a first plunger end (141); wherein the first plunger end (141) is disposed through the first column end (111) and within the filtration column (110).

Embodiment 43A: The system of any one of embodiments 39A-42A, wherein the first filter (131) comprises a polyethylene (PET) filter.

Embodiment 44A: The system of any one of embodiments 39A-43A, wherein the second filter (132) comprises a polyethylene (PET) filter Embodiment 45A: The system of embodiment 43A or embodiment 44A, wherein the PET filter is 35p PET filter.

Embodiment 46A: The system of any one of embodiments 39A-45A, wherein the solid support (133) comprises cellulose.

Embodiment 47A: The system of any one of embodiments 39A-45A, wherein the solid support (133) comprises nitrocellulose.

Embodiment 48A: The system of any one of embodiments 39A-45A, wherein the solid support (133) comprises a cotton pad.

Embodiment 49A: The system of any one of embodiments 39A-45A, wherein the solid support (133) comprises paper.

Embodiment 50A: The system of any one of embodiments 39A-49A, further comprises a prefilter (230) disposed at the second sample vial end (212).

Embodiment 51A: The system of embodiment 50A, wherein the prefilter (230) comprises a polypropylene (PP) mesh filter.

Embodiment 52A: The system of embodiment 51A, wherein the PP mesh filter comprises a 700 μm-200 μm PP mesh filter.

Embodiment 53A: The system of embodiment 51A or embodiment 52A, wherein the PP mesh filter comprises a 700 μm-350 μm PP mesh filter.

Embodiment 54A: The system of any one of embodiments 50A-53A, wherein the prefilter (230) is removable.

Embodiment 55A: A method for isolating nucleic acids from a biological sample, the method comprising: (a) obtaining a system according to any one of embodiments 39A-54A, (b) creating negative pressure within the filtration column (110) to pull the lysed biological sample from the sample vial (120) through the prefilter (230) and through the filter component (130), into the first column end (111) of the filtration column (110); and (c) creating a positive pressure within the filtration column (110) to push the lysed biological sample through the filter component (130) and back into the sample vial (210), wherein the nucleic acids are isolated and reversibly bound the solid support (133) of the filter component (120).

Embodiment 56A: A sample processing method for isolating and extracting genomic nucleic acids from a biological sample.

Embodiment 57A: The method of embodiment 56A, wherein the genomic nucleic acids comprise genomic DNA or genomic RNA.

Embodiment 58A: The method of embodiment 57A, wherein the genomic RNA comprises mRNA or RNA from an RNA-virus.

Embodiment 59A: The method of embodiment 56A, wherein the method can collect genomic DNA from the sample at a minimum concentration of 270 ng/ul.

Embodiment 60A: The method of embodiment 59A, wherein the processed sample comprises ground tissue in a lysis buffer.

Embodiment 61A: The method of embodiment 56A, wherein the method comprises introducing the sample to a sample vial (210).

Embodiment 62A: The method of embodiment 61A, wherein the sample is housed in a sample vial (210).

Embodiment 63A: The method of embodiment 61A or embodiment 62A, wherein the sample vial (210) comprises a cap, wherein a prefilter (230) is disposed therein.

Embodiment 64A: The method of embodiment 63A, wherein the prefilter (230) in the cap of the sample vial (210) is a mesh filter.

Embodiment 65A: The method of embodiment 63A, wherein the prefilter (230) in the cap of the sample vial (210) comprises two mesh filters.

Embodiment 66A: The method of embodiment 63A, wherein the cap is an attachable cap.

Embodiment 67A: The method of embodiment 63A, wherein the cap can be secured to the vial to prevent leakage.

Embodiment 68A: The method of embodiment 63A, wherein the cap can be welded or glued to the vial to prevent leakage.

Embodiment 69A: The method of embodiment 63A, wherein the sample vial (210) is attachable to a filtration column (110), wherein an opening (120) of the filtration column (110) attaches to the cap of the sample vial (210).

Embodiment 70A: The method of embodiment 69A, wherein the method comprises connecting a sample vial (210) with the sample to a filtration column (110).

Embodiment 71A: The method of embodiment 70A, wherein the filtration column (110) comprises a filter component (130) therein.

Embodiment 72A: The method of embodiment 71A, wherein the filter component (130) of the filtration column (110) comprises a polyethylene (PET) filter and a cellulose filter.

Embodiment 73A: The method of embodiment 71A, wherein the filter component (130) of the filtration column (110) comprises a cellulose filter sandwiched between two PET filters.

Embodiment 74A: The method of embodiment 71A, wherein the filtration column (110) further comprises a cap with a septa at a first column end (111) and an opening (120) at a second column end (112), wherein the filter component (130) is disposed in between the outlet and septa.

Embodiment 75A: The method of embodiment 74A, wherein the cap with septa is not removable.

Embodiment 76A: The method of embodiment 74A, wherein the cap with septa is removable.

Embodiment 77A: The method of embodiment 74A, wherein the cap with septa is secured to the filtration column (110) to prevent leakage.

Embodiment 78A: The method of embodiment 74A, wherein the cap with septa is secured to the filtration column (110) to maintain pressure.

Embodiment 79A: The method of embodiment 74A, wherein the septa allows a syringe needle therethrough.

Embodiment 80A: The method of embodiment 69A further comprising introducing a syringe through the septa and via the syringe pulling the sample from the sample vial (210) through at least the filter component (130) of the filtration column (110).

Embodiment 81A: The method of embodiment 80A further comprising pushing the sample through at least the filter component (130) of the filtration column (110) via the syringe.

Embodiment 82A: The method of embodiment 80A or embodiment 81A further comprising repeating said steps one or more times.

Embodiment 83A: The method of embodiment 82A further comprising eluting nucleic acids collected by the filter component (130) of the filtration column (110).

Embodiment 84A: The method of embodiment 83A, wherein elution buffer is introduced to the filter component (130) of the filtration column (110).

Embodiment 85A: The method of embodiment 84A, wherein a needle is attached to the opening (120) of the filtration column (110) and inserted into a second elution vial end (312) of the elution vial (310) comprising elution buffer, wherein the elution buffer is introduced to the filtration column (110) via pulling the syringe.

Embodiment 86A: The method of embodiment 85A, wherein the elution buffer is pushed from the filtration column (110) into the elution vial (310) via the syringe.

Embodiment 87A: The method of embodiment 86A, wherein the elution buffer comprises genomic DNA extracted from the sample.

Embodiment 88A: A method of extracting nucleic acids from a sample, the method comprising (a) lysing a tissue sample, wherein the lysed sample is in an enclosed sample vial (210); (b) attaching a filtration column (110) to the enclosed sample vial (210), wherein the filtration column (110) comprises at least two polyethylene (PET) filters and cellulose filter paper sandwiched between the PET filters, wherein the filtration column (110) enclosed with a cap and a rubber septa, wherein the filter column attaches to a screw-on cap with a prefilter (230) on the enclosed sample vial (210); (c) inserting a syringe through the rubber septa-connected cap of the filtration column (110) connected to the enclosed sample vial (210); (d) creating a vacuum in the filter column using the syringe; (e) pulling the lysed tissue sample from the enclosed sample vial (210) through the filters into the filtration column (110); (f) pushing the lysed tissue sample back through the filters in the filtration column (110) into the enclosed sample vial (210); (g) detaching the sample vial (210) form the filtration column (110); (h) attaching a blunt needle to the filtration column (110); (i) inserting the blunt needle into a elute vial (310) comprising an elution buffer; co pulling the elution buffer through the the filters in the filtration column (110) and (k) pushing the elution buffer back through the filters in the filtration column (110) into the elution vial (310); wherein step (j) and (k) are repeated at least 1-10 times.

Embodiment Set B

Embodiment 1B: A device (1000) for isolating and extracting nucleic acids from a biological sample, the device comprising: (a) a sample vial (1210) comprising a sample vial opening (1220) is disposed at second sample vial end (1212) and a sample vial outlet (1221) disposed at a first sample vial end (1211); (b) a first collection tube (1410) comprising a inlet (1421) at a first collection tube end (1411) and a second collection tube end (1412) comprising a means for providing positive and negative pressure disposed therein; wherein the inlet (1421) of the first collection tube (1410) is fluidly connected to the sample vial outlet (1221); (c) an elution vial (1310) comprising an elution vial opening (1320) disposed at a second elution vial end (1312) and an first elution end (1311), (d) a elution tube (1610) comprising a inlet (1621) at a first elution tube end (1611) and a second elution tube end (1612) comprising a means for providing positive and negative pressure disposed therein; wherein the inlet (1621) of the elution tube (1610) is fluidly connected to the elution vial opening (1320); and (e) a filter component (1130) positioned between all of: the sample vial (1210), the sample tube (141), the elution vial (1310), and the elution tube (1610) such that fluid moving between the sample vial and sample tube or between the sample tube and elution tube or between the elution tube and elution vial necessarily passes through the filter component, the filter component (1130) is capable of temporarily binding nucleic acid.

Embodiment 2B: The device (1000) of embodiment 1B, wherein the sample vial (1210) further comprises a cover (1222).

Embodiment 3B: The device (1000) of embodiment 1B, wherein the cover (1222) further comprises a pestle disposed therethrough.

Embodiment 4B: The device (1000) of embodiment 2B or embodiment 3B, wherein the cover (1222) is configured to seal the sample vial (1210).

Embodiment 5B: The device (1000) of embodiment 1B, wherein the sample vial (1210) further comprises a plug; wherein the plug attaches to the sample vial outlet (1221).

Embodiment 6B: The device (1000) of embodiment 5B, wherein the plug is removable.

Embodiment 7B: The device (1000) of any one of embodiments 1B-6B, wherein the sample vial (1210) further comprises a prefilter (1230).

Embodiment 8B: The device (1000) of any one of embodiments 1B-6B, wherein the sample vial (1210) further comprises a plurality of prefilters (1230).

Embodiment 9B: The device (1000) of embodiment 7B or embodiment 8B, wherein the prefilter (1230) is positioned between the sample vial (1210) and the filter component (1130), wherein the prefilter is capable of filtering cellular debris.

Embodiment 10B: The device (1000) of embodiment 9B, wherein the prefilter (1230) is disposed adjacent to the sample vial outlet (1221) and not within the sample vial (1210).

Embodiment 11B: The device (1000) of embodiment 1B, wherein means for providing positive and negative pressure in the first collection tube (1410) is a plunger (1440) slidably coupled to the second sample tube end (1412).

Embodiment 12B: The device (1000) of embodiment 11B, wherein the plunger (1440) comprises a first plunger end (1441); wherein the first plunger end (1441) is disposed through the second sample tube end (1412) and within the first collection tube (1410).

Embodiment 13B: The device (1000) of embodiment 11B or embodiment 12B, wherein the first collection tube (1410) comprises a syringe.

Embodiment 14B: The device (1000) of embodiment 13B, wherein the syringe comprises a needleless syringe.

Embodiment 15B: The device (1000) of embodiment 1B, wherein means for providing positive and negative pressure in the elution tube (1610) is a plunger (1640) slidably coupled to the second elution tube end (1612).

Embodiment 16B: The device (1000) of embodiment 15B, wherein the plunger (1640) comprises a first plunger end (1641); wherein the first plunger end (1641) is disposed through the second elution tube end (1612) and within the elution tube (1610).

Embodiment 17B: The device (1000) of embodiment 15B or embodiment 16B, wherein the elution tube (1610) comprises a syringe.

Embodiment 18B: The device (1000) of embodiment 17B, wherein the syringe comprises a needleless syringe.

Embodiment 19B: The device (1000) of embodiment 1B, wherein the elution vial (1310) comprises a cap; wherein the cap is attached to the second elution vial end (1312).

Embodiment 20B: The device (1000) of embodiment 19B, wherein the cap is configured to cover the elution vial opening (1320), to create a sealed elution vial (1310).

Embodiment 21B: The device (1000) of embodiment 20B, wherein the cap further comprises a needle disposed therethrough.

Embodiment 22B: The device (1000) of embodiment 23B, wherein the needle is fluidly connected to the first elution tube end (1611).

Embodiment 23B: The device (1000) of any one of embodiments 1B-22B, wherein the elution vial is removable.

Embodiment 24B: The device (1000) of any one of embodiments 1B-22B, wherein the elution vial is removable.

Embodiment 25B: The device (1000) of embodiment 24B, wherein the filter component (1130) comprises a plurality of solid supports (1133)

Embodiment 26B: The device (1000) of embodiment 25B, wherein the filter component (1130) comprises two solid supports (1133).

Embodiment 27B: The device (1000) of embodiment 26B, wherein the filer component (1130) comprises four solid supports (1133).

Embodiment 28B: The device (1000) of embodiments 24B-27B, wherein the solid support (1133) comprises cellulose, nitrocellulose, a cotton pad, paper, or a combination thereof.

Embodiment 29B: The device (1000) of embodiment 1B or embodiment 24B, wherein the filter component (1130) further a first filter (1131) adjacent to or in contact with the solid support (1133).

Embodiment 30B: The device (1000) of embodiment 1B or embodiment 24B, wherein the filter component (1130) further comprises a first filter (1131) and a second filter (1132) wherein the solid support (1133) is sandwiched between the first filter (1131) and second filter (1132).

Embodiment 31B: The device (1000) of any one of embodiments 1B-30B, wherein the filter component (1130) is disposed within a valve.

Embodiment 32B: The device (1000) of embodiment 31B, wherein the valve comprises a first valve position and a second valve position.

Embodiment 33B: The device (1000) of embodiment 32B, wherein when the valve is in the first valve position the valve fluidly connects the sample tube (1210) to the sample vial (1210).

Embodiment 34B: The device (1000) of embodiment 33B, wherein when the valve is in the first valve position the elution tube (1610) is not fluidly connected to the elution vial (1310).

Embodiment 35B: The device (1000) of embodiment 32B, wherein when the valve is in the second valve position the valve fluidly connects the elution tube (1610) to the elution vial (1310).

Embodiment 36B: The device (1000) of embodiment 35B, wherein when the valve is in the second valve position the first collection tube (1410) is not fluidly connected to the sample vial (1210)

Embodiment 37B: The device (1000) on any one of embodiments 1B-36B, wherein the device (1000) is handheld.

Embodiment 38B: The device (1000) on any one of embodiments 1B-37B, wherein the device is 3 inches wide and 5 inches tall.

Embodiment 39B: The device (1000) on any one of embodiments 1B-38B, wherein the device (1000) is enclosed.

Embodiment 40B: A method of isolating and extracting nucleic acids from a biological sample using a device according to any one of embodiments 1B-39B.

Embodiment 41B: The method of embodiment 40B, wherein the method comprises adding a biological sample to the sample vial (1210).

Embodiment 42B: The method of embodiment 41B, wherein the sample vial (1210) comprises a lysis buffer.

Embodiment 43B: The method of any one of embodiments 40B-42B, wherein the biological sample is a saliva, blood, or urine.

Embodiment 44B: The method of any one of embodiments 40B-43B, wherein the method comprises enclosing the sample vial (1210) with a cover (1222).

Embodiment 45B: The method of any one of embodiments 40B-44B, wherein the biological sample is a tissue sample.

Embodiment 46B: The method of embodiment 45B, wherein the biological sample is a shrimp tissue sample.

Embodiment 47B: The method of any one of embodiments 40B-46B, wherein the method comprises enclosing the sample vial (1210) with a cover (1222) comprising a pestle disposed therethrough.

Embodiment 48B: The method of embodiment 47B, wherein the method comprises grinding the sample, wherein grinding the sample comprises axially rotating the pestle.

Embodiment 49B: The method of embodiment 48B, wherein the pestle is rotated bidirectionally.

Embodiment 50B: The method of any one of embodiments 40B-49B, wherein the method comprises removing a plug from the sample vial outlet (1221) disposed at a first sample vial end (1211).

Embodiment 51B: The method of embodiment 40B-50B, wherein the method comprises creating negative pressure within the first collection tube (1410) to pull the biological sample from the sample vial (1210) through the filter component (1130), into the first collection tube (1410).

Embodiment 52B: The method of embodiment 51B, wherein the biological sample is further pulled through a prefilter (1230).

Embodiment 53B: The method of embodiment 51B, wherein the filter component (1130) is disposed within a valve.

Embodiment 54B: The method of embodiment 53B, wherein the valve is in a first valve position such that the sample vial (1210) and first collection tube (1410) are fluidly connected.

Embodiment 55B: The method of any one of embodiments 40B-54B, wherein the filter component (1130) comprises isolated nucleic acid Embodiment 56B: The method of embodiment 55B, wherein the isolated nucleic acids comprise genomic DNA or genomic RNA.

Embodiment 57B: The method of embodiment 56B, wherein the genomic RNA comprises mRNA or RNA from an RNA-virus.

Embodiment 58B: The method of embodiment 55B, wherein the isolated nucleic acid is reversibly bound to the solid support (1133) of the filter component (1130).

Embodiment 59B: The method of embodiment 53B, wherein the filter component (1130) comprises a plurality of solid supports (1133).

Embodiment 60B: The method of embodiment 59B, wherein the filter component (1130) comprises two solid supports (1133).

Embodiment 61B: The method of embodiment 59B, wherein the filer component (1130) comprises four solid supports (1133).

Embodiment 62B: The method of embodiments 59B-61B, wherein the solid support (1133) comprises cellulose, nitrocellulose, a cotton pad, paper, or a combination thereof.

Embodiment 63B: The method of any one of embodiments 40B-62B, further comprising turning the valve comprising the filter component (1130) to a second position, such that the elution tube (1610) to the elution vial (1310) are fluidly connected.

Embodiment 64B: The method of embodiment 63B, wherein the elution tube (1610) comprises an elution buffer.

Embodiment 65B: The method of any one of embodiments 40B-63B, wherein the method comprises creating positive pressure within the elution tube (1610) to push the elution buffer from the elution tube (1610) through the filter component (1130), into the elution vial (1310).

Embodiment 66B: The method of any one of embodiments 40B-65B, wherein the method comprises creating a negative pressure within the elution tube (1610) to pull the elution buffer from the elution vial (1310) through the filter component (1130), into the elution tube (1610).

Embodiment 67B: The method of any one of embodiments 40B-66B, further comprising repeating the steps of embodiments 65B and 66B one or more times.

Embodiment 68B: The method of embodiments 55B-58B, wherein the isolated nucleic acid is eluted from the filter component (1130).

Embodiment 69B: The method of embodiments 55B-58B, wherein the isolated nucleic acid is eluted from the solid support (1133) of the filter component (1130).

Embodiment 70B: The method of any one of embodiments 65B-67B, wherein the elution buffer comprises nucleic acids extracted from the biological sample.

Embodiment 71B: The method of any one of embodiments 40B-70B, further comprising removing the elution vial (1310).

Embodiment 72B: The method of embodiment 71B, wherein the elution vial comprises an elution buffer comprising genomic DNA.

Embodiment Set C

Embodiment 1C: A device (1000) for isolating and extracting nucleic acids from a biological sample, the device comprising: (a) a sample vial (1210) comprising a sample vial opening (1220) disposed at second sample vial end (1212) and a sample vial outlet (1221) disposed at a first sample vial end (1211); (b) a hub (1510) comprising an opening (1520); wherein the hub (1510) is fluidly connected to the sample vial outlet (1221); (c) an elution vial (1310) comprising an elution vial opening (1320) disposed at a second elution vial end (1312) and an first elution end (1311); wherein the hub (1510) is fluidly connected to the elution vial opening (1320); (d) a filter component (1130) positioned between all of: the sample vial (1210), the hub (1510), and the elution vial such that fluid moving between the sample vial and hub or between the hub and elution vial necessarily passes through the filter component.

Embodiment 2C: The device (1000) of embodiment 1C, wherein the hub (1510) comprises a Luer lock fitting.

Embodiment 3C: The device (1000) of embodiment 2C, wherein the Luer lock fitting is a female Luer lock fitting.

Embodiment 4C: The device (1000) of embodiment 2C, wherein the Luer lock fitting is a male Luer lock fitting.

Embodiment 5C: The device (1000) of embodiment 1C, wherein the sample vial (1210) further comprises a cover (1222).

Embodiment 6C: The device (1000) of embodiment 5C, wherein the cover (1222) further comprises a pestle disposed therethrough.

Embodiment 7C: The device (1000) of embodiment 5C or embodiment 6C, wherein the cover (1222) is configured to seal the sample vial (1210).

Embodiment 8C: The device (1000) of embodiment 1C, wherein the sample vial (1210) further comprises a plug; wherein the plug attaches to the sample vial outlet (1221).

Embodiment 9C: The device (1000) of embodiment 8C, wherein the plug is removable.

Embodiment 10C: The device (1000) of any one of embodiments 1C-9C, wherein the sample vial (1210) further comprises a prefilter (1230).

Embodiment 11C: The device (1000) of any one of embodiments 1C-10C, wherein the sample vial (1210) further comprises a plurality of prefilters (1230).

Embodiment 12C: The device (1000) of embodiment 10C or embodiment 11C, wherein the prefilter is positioned between the sample vial (1210) and the filter component (1130), wherein the prefilter is capable of filtering cellular debris.

Embodiment 13C: The device (1000) of embodiment 12C, wherein the prefilter (1230) is disposed adjacent to the sample vial outlet (1221) and not within the sample vial (1210).

Embodiment 14C: The device (1000) of any one of embodiments 1C-13C, wherein the filter component (1130) comprises a solid support (1133) adapted to reversibly bind nucleic acid.

Embodiment 15C: The device (1000) of embodiment 15C, wherein the filter component (1130) comprises a plurality of solid supports (1133).

Embodiment 16C: The device (1000) of embodiment 15C, wherein the filter component (1130) comprises two solid supports (1133).

Embodiment 17C: The device (1000) of embodiment 15C, wherein the filer component (1130) comprises four solid supports (1133).

Embodiment 18C: The device (1000) of embodiments 14C-17C, wherein the solid support (1133) comprises cellulose, nitrocellulose, a cotton pad, paper, or a combination thereof.

Embodiment 19C: The device (1000) of any one of embodiments 14C-18C, wherein the filter component (1130) further a first filter (1131) adjacent to or in contact with the solid support (1133).

Embodiment 20C: The device (1000) of any one of embodiments 14C-19C, wherein the filter component (1130) further comprises a first filter (1131) and a second filter (1132) wherein the solid support (1133) is sandwiched between the first filter (1131) and second filter (1132).

Embodiment 21C: The device (1000) of any one of embodiments 1C-20C, wherein the filter component (1130) is disposed within a valve.

Embodiment 22C: The device (1000) of embodiment 21C, wherein the valve comprises a first valve position and a second valve position.

Embodiment 23C: The device (1000) of any one of embodiments 1C-22C, further comprising a first collection tube (1410) comprising a inlet (1421) at a first sample tube end (1411) and a second collection tube end (1412) comprising a means for providing positive and negative pressure disposed therein.

Embodiment 24C: The device (1000) of embodiment 23C, wherein the inlet (1421) at the first collection tube end (1411) fluidly connects to the opening (1520) of the hub (1510).

Embodiment 25C: The device (1000) of embodiment 23C, wherein means for providing positive and negative pressure in the first collection tube (1410) is a plunger (1440) slidably coupled to the second sample tube end (1412).

Embodiment 26C: The device (1000) of embodiment 25C, wherein the plunger (1440) comprises a first plunger end (1441); wherein the first plunger end (1441) is disposed through the second sample tube end (1412) and within the first collection tube (1410).

Embodiment 27C: The device (1000) of embodiment 23C or embodiment 24C, wherein the inlet (1421) at the first sample tube end (1411) comprises a Luer lock fitting.

Embodiment 28C: The device (1000) of embodiment 27C, wherein the Luer lock fitting is a male Luer lock fitting.

Embodiment 29C: The device (1000) of embodiment 27C, wherein the Luer lock fitting is a female Luer lock fitting.

Embodiment 30C: The device (1000) of any one of embodiments 21C-29C, wherein when the valve is in the first valve position the valve fluidly connects the collection tube (1410) to the sample vial (1210).

Embodiment 31C: The device (1000) of embodiment 30C, wherein when the valve is in the first valve position neither the collection tube (1410) nor the sample vial (1210) is fluidly connected to the elution vial (1310).

Embodiment 32C: The device (1000) of any one of embodiments 1C-31C, further comprising an elution tube (1610) comprising a inlet (1621) at a first elution tube end (1611) and a second elution tube end (1612) comprising a means for providing positive and negative pressure disposed therein.

Embodiment 33C: The device (1000) of embodiment 31C, wherein the inlet (1621) at the first elution tube end (1611) fluidly connects to the opening (1520) of the hub (1510).

Embodiment 34C: The device (1000) of embodiment 32C, wherein means for providing positive and negative pressure in the elution tube (1610) is a plunger (1640) slidably coupled to the second elution tube end (1612).

Embodiment 35C: The device (1000) of embodiment 34C, wherein the plunger (1640) comprises a first plunger end (1641); wherein the first plunger end (1641) is disposed through the second elution tube end (1612) and within the elution tube (1610).

Embodiment 36C: The device (1000) of embodiment 32C or embodiment 33C, wherein the inlet (1621) at the first elution tube end (1611) comprises a Luer lock fitting.

Embodiment 37C: The device (1000) of embodiment 36C, wherein the Luer lock fitting is a male Luer lock fitting.

Embodiment 38C: The device (1000) of embodiment 36C, wherein the Luer lock fitting is a female Luer lock fitting.

Embodiment 39C: The device (1000) of any one of embodiments 21C-38C, wherein when the valve is in the second valve position the valve fluidly connects the elution tube (1610) to the elution vial (1310).

Embodiment 40C: The device (1000) of embodiment 39C, wherein when the valve is in the second valve position neither the elution tube (1610) nor the elution vial (1310) is fluidly connected to the sample vial (1210).

Embodiment 41C: The device (1000) of any one of embodiments 23C-41C, wherein the first collection tube (1410) and the elution tube (1610) are removable.

Embodiment 42C: The device (1000) of any one of embodiments 23C-41C, wherein the first collection tube (1410) and the elution tube (1610) are interchangeable.

Embodiment 43C: The device (1000) of any one of embodiments 23C-42C, wherein only the first collection tube (1410) or the elution tube (1610) is fluidly connected to the opening (1520) of the hub (1510) at a given time.

Embodiment 44C: The device (1000) of any one of embodiments 1C-43C, wherein the elution vial (1310) is removable.

Embodiment 45C: The device (1000) on any one of embodiments 1C-44C, wherein the device (1000) is hand-held.

Embodiment 46C: The device (1000) on any one of embodiments 1C-45C, wherein the device (1000) is enclosed.

Embodiment 47C: A method of isolating and extracting nucleic acids from a biological sample using a device according to any one of embodiments 1C-46C.

Embodiment 48C: The method of embodiment 47C, wherein the method comprises adding a biological sample to the sample vial (1210).

Embodiment 49C: The method of embodiments 47C or 48C, wherein the biological sample is a saliva, blood, or urine.

Embodiment 50C: The method of embodiments 47C or 48C, wherein the biological sample is a tissue sample.

Embodiment 51C: The method of embodiment 50C, wherein the biological sample is a shrimp tissue sample.

Embodiment 52C: The method of embodiment 48C, wherein the sample vial (1210) comprises a lysis buffer.

Embodiment 53C: The method of any one of embodiments 47C-52C, wherein the method comprises enclosing the sample vial (1210) with a cover (1222).

Embodiment 54C: The method of any one of embodiments 47C-52C, wherein the method comprises enclosing the sample vial (1210) with a cover (1222) comprising a pestle disposed therethrough.

Embodiment 55C: The method of embodiment 54C, wherein the method comprises grinding the sample, wherein grinding the sample comprises axially rotating the pestle.

Embodiment 56C: The method of embodiment 55C, wherein the pestle is rotated bidirectionally.

Embodiment 57C: The method of any one of embodiments 47C-56C, wherein the method further comprises attaching the inlet (1421) at the first collection tube end (1411) to the hub (1510), such that the inlet (1421) is fluidly connected to the opening (1520) of the hub (1510).

Embodiment 58C: The method of any one of embodiment 47C-57C, wherein the method further comprising positioning the valve, comprising the filter component (1130), to the first position such that the collection tube (1410) is fluidly connected to the sample vial (1210).

Embodiment 59C: The method of any one of embodiments 47C-58C, wherein the method comprises removing the plug from the sample vial outlet (1221) disposed at a first sample vial end (1211).

Embodiment 60C: The method of embodiment 47C-58C, wherein the method comprises creating negative pressure within the first collection tube (1410) to pull the biological sample from the sample vial (1210) through the filter component (1130), into the first collection tube (1410).

Embodiment 61C: The method of embodiment 60C, wherein the biological sample is further pulled through a prefilter (1230).

Embodiment 62C: The method of any one of embodiments 47C-61C, wherein the filter component (1130) comprises isolated nucleic acid.

Embodiment 63C: The method of embodiment 62C, wherein the isolated nucleic acids comprise genomic DNA or genomic RNA.

Embodiment 64C: The method of embodiment 63C, wherein the genomic RNA comprises mRNA or RNA from an RNA-virus.

Embodiment 65C: The method of any one of embodiments 47C-64C further comprising removing the first collection tube (1410) from the hub (1510).

Embodiment 66C: The method of any one of embodiments 47C-65C further comprising attaching the inlet (1621) at the first elution tube end (1611) to the hub (1510), such that the inlet (1621) is fluidly connected to the opening (1520) of the hub (1510).

Embodiment 67C: The method of any one of embodiments 40C-62C, further comprising positioning the valve comprising the filter component (1130) to a second position, such that the elution tube (1610) to the elution vial (1310) are fluidly connected.

Embodiment 68C: The method of embodiment 67C, wherein the elution vial (1310) comprises an elution buffer.

Embodiment 69C: The method of any one of embodiments 66C-68C, further comprising creating negative pressure within the elution tube (1610) to pull the elution buffer from the elution vial (1310) through the filter component (1130), into the elution tube (1610).

Embodiment 70C: The method of any one of embodiments 66C-69C, further comprising creating positive pressure within the elution tube (1610) to push the elution buffer from the elution tube (1610) through the filter component (1130), into the elution vial (1310). The method of any one of embodiments 66-69, further comprising creating positive pressure within the elution tube (1610) to push the elution buffer from the elution tube (1610) through the filter component (1130), into the elution vial (1310).

Embodiment 71C: The method of any one of embodiments 66C-70C, further comprising repeating the steps of embodiments 69 and 70 one or more times.

Embodiment 72C: The method of any one of embodiments 66C-71C, wherein the isolated nucleic acid is eluted from the filter component (1130).

Embodiment 73C: The method of any one of embodiments 66C-72C, wherein the isolated nucleic acid is eluted from the solid support (1133) of the filter component (1130).

Embodiment 74C: The method of any one of embodiments 66C-73C, wherein the elution buffer comprises nucleic acids extracted from the biological sample.

Embodiment 75C: The method of any one of embodiments 47C-74C, further comprising removing the elution vial (1310).

Embodiment 76C: The method of embodiment 75C, wherein the elution vial comprises an elution buffer comprising genomic DNA.

Embodiment Set D

Embodiment 1D: A system for isolating and extracting nucleic acids from a biological sample, the device comprising: (a) a filter cartridge (600) comprising a cartridge housing (610) with a first end (611) and a second end (612) and a filter component (630) sandwiched between said ends, wherein the first end (611) comprises a first port (620) and the second end (612) comprises a second port (622), the ports are open to allow insertion and removal of fluid wherein the filter component (630) reversibly binds nucleic acids; (b) a sample tube (500) comprising a sample tube housing (510) for holding a fluid; a first cap (520) removably attachable to a first end (511) of the sample tube (500); wherein the first cap (520) comprises a cap port (522) adapted to snugly engage the first port (620) or second port (622) of the filter cartridge (600), the cap port (520) is open to allow passage of fluid from the sample tube housing (510) to the filter cartridge (600); and (c) a first means for providing positive and negative pressure for moving the fluid from the sample tube (500) and through the filter cartridge (600) from the first end (611) to the second end (612) or from the second end (612) to the first end (611) via the filter component.

Embodiment 2D: The system of embodiment 1D; wherein the filter component (630) comprises a solid support.

Embodiment 3D: The system of embodiment 2D wherein the solid support comprises cellulose, nitrocellulose, a cotton pad, paper, or a combination thereof.

Embodiment 4D: The system of embodiment 1D, wherein the cap (520) is directly connected to the sample tube (500).

Embodiment 5D: The system of embodiment 1D, wherein the cap (520) is separate from the sample tube (500).

Embodiment 6D: The system of embodiment 4D or claim 5D, wherein the cap (620) can be attached to the first end (511) of the sample tube (500).

Embodiment 7D: The system (1000) of embodiment 6D, wherein the cap (520) snugly engages to the first end (511) of the sample tube (500) via a seal (525).

Embodiment 8D: The device (1000) of any one of embodiments 1D-7D, wherein the first cap (520) further comprising a prefilter (530) positioned between the sample tube housing (510) and cap port (522) or within the cap port (522), wherein the prefilter (530) is adapted to filter cellular debris.

Embodiment 9D: The system of embodiment 1D, wherein the means for providing positive and negative pressure comprises a first syringe (700).

Embodiment 10D: The system of embodiment 9D, wherein the syringe (700) comprises a syringe housing (710), a plunger (730), and a syringe port (720), wherein the syringe port (720) is disposed at a first end of the syringe (700) and open to allow passage of fluid.

Embodiment 11D: The system of embodiment 10D, wherein the syringe port (720) snugly engages the first port (620) or second port (622) of the filter cartridge (600).

Embodiment 12D: The device of embodiment 10D, wherein the syringe housing (710) is capable of housing at least a portion of the fluid from the sample tube (500) having moved through the filter cartridge (600).

Embodiment 13D: The system of any one of embodiments 1D-12D, wherein the fluid is a biological sample.

Embodiment 14D: The system of embodiment 1D further comprising: (a) a second sample tube (500) comprising a sample tube housing (510) for holding a fluid; (b) a second cap (550) removably attachable to the first end (511) of the second sample tube (500), wherein the second cap (550) comprises a cap port (520) adapted to sungly engage the first port (620) or second port (622) of the filter cartridge (600), the cap port (520) is open to allow passage of fluid from the second sample tube housing (510) to the filter cartridge (600); and (c) a second means for providing positive and negative pressure for moving the fluid from the second sample tube (500) and through to the filter cartridge (600) from the first end (611) to the second end (612) or from the second end (612) to the first end (611) via the filter component.

Embodiment 15D: The system of embodiment 14D, wherein the second cap (550) is directly connected to the second sample tube (500).

Embodiment 16D: The system (1000) of embodiment 14D, wherein the second cap (550) is separate from the second sample tube (500).

Embodiment 17D: The system of embodiment 15D or embodiment 16D, wherein the cap (820) snugly engages the first end (511) of the second sample tube (550) via a seal (525).

Embodiment 18D: The system of embodiment 14D, wherein the means for providing positive and negative pressure comprises a second syringe (700).

Embodiment 19D: The system of embodiment 19D, wherein the second syringe (700) comprises a syringe housing (710), a plunger (730), and a syringe port (720), wherein the syringe port (720) is disposed at a first end of the second syringe (700) and open to allow passage of fluid.

Embodiment 20D: The system of embodiment 20D, wherein the syringe port (720) snugly engages the first port (620) or second port (622) of the filter cartridge (600).

Embodiment 21D: The system of any one of embodiments 20D, wherein the fluid is an elution buffer.

Embodiment 22D: A kit comprising two sample tubes (500), a first cap (520), a second cap (550), two syringes (700), and a filter cartridge (600).

Embodiment 23D: A kit comprising a first sample tube (500) having a first cap (520), a second sample tube (500) having a second cap (550), two syringes (700), and a filter cartridge (600).

Embodiment 24D: The kit of embodiment 22D or embodiment 23D further comprising a lysis buffer (501), an elution buffer (502), or both a lysis buffer (501) and an elution buffer (502).

The present invention also features a lysis buffer comprising 20 mM PBS, 2.5 mM EDTA, and 0.05% SDS.

As used herein, the term "about" refers to plus or minus 10% of the referenced number.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting essentially of" or "consisting of", and as such the written description requirement for claiming one or more embodiments of the present invention using the phrase "consisting essentially of" or "consisting of" is met.

The reference numbers recited in the below claims are solely for ease of examination of this patent application, and are exemplary, and are not intended in any way to limit the scope of the claims to the particular features having the corresponding reference numbers in the drawings.

What is claimed is:

1. A system for isolating and extracting one or more nucleic acids from a biological sample, the system comprising:

a filter cartridge; and a first sample tube, wherein:

the filter cartridge comprises a cartridge housing and a filter component;

the cartridge housing includes a first housing end and a second housing end;

the filter component is disposed between the first housing end and the second housing end;

the first housing end comprises a fluid opening port configured to allow one or more fluids to enter and to exit the filter cartridge;

the filter component comprises a solid support comprising a cellulose filter punch configured to reversibly bind one or more nucleic acids;

the first sample tube comprises a first tube end, a first tube housing and a first cap;

the first tube housing is configured to hold a first fluid;

the first cap is removably attachable to the first tube end;

the first cap comprises a first cap port adapted to snugly engage the fluid opening port; and the first cap port is configured to fluidly communicate the first sample tube and the filter cartridge.

2. The system of claim 1, wherein the first cap further comprises a prefilter positioned between the first tube housing and the first cap port or within the first cap, wherein the prefilter is adapted to filter cellular debris.

3. The system of claim 1, wherein the first sample tube is configured to hold the biological sample comprising saliva, blood, urine or biological tissue.

4. The system of claim 1, wherein the first sample tube is configured to hold a lysis buffer.

5. The system of claim 1, wherein the first sample tube is configured to hold a lysed biological sample comprising genomic DNA or genomic RNA comprising mRNA or RNA from an RNA-virus.

6. The system of claim 1, wherein the cellulose filter punch includes pores having has a pore size of about 10 μm.

7. The system of claim 1, wherein the first cap is directly connected to the first sample tube.

8. The system of claim 1, wherein the first cap is separate from the first sample tube.

9. The system of claim 1, wherein the filter cartridge is configured to attach the sample tube via a screw-on cap on the sample tube.

10. The system of claim 1, wherein the filter cartridge is enclosed by a cap and a rubber septum.

11. The system of claim 1, further comprising a second sample tube comprising a second tube housing configured to hold a second fluid.

12. The system of claim 11, wherein the second tube includes a second tube end and the system further comprises a second cap removably attachable to the second tube end.

13. The system of claim 12, wherein the second cap comprises a second cap port adapted to engage the fluid opening port, the second cap port is configured to allow the second fluid from the second tube housing through the second cap port to the filter cartridge.

14. The system of claim 1, wherein the one or more fluids is an elution buffer.

15. The system of claim 14, wherein the elution buffer comprises genomic DNA extracted from the biological sample.

16. The system of claim 1, further comprising a syringe configured to move the biological sample through said system.

17. The system of claim 1, wherein the fluid opening port is configured to allow insertion of a lysed biological sample fluid.

18. The system of claim 1, wherein the fluid opening port is configured to allow removal of a third fluid comprising one or more isolated and extracted nucleic acids.

19. The system of claim 1, wherein the system is an enclosed system.

* * * * *